＊

US008318760B2

(12) United States Patent
Stelmach et al.

(10) Patent No.: US 8,318,760 B2
(45) Date of Patent: Nov. 27, 2012

(54) SUBSTITUTED ARYL AND HETEROARYL DERIVATIVES, COMPOSITIONS CONTAINING SUCH COMPOUNDS AND METHODS OF USE

(75) Inventors: John E. Stelmach, Westfield, NJ (US); Keith G. Rosauer, Laurence Harbor, NJ (US); Emma R. Parmee, Scotch Plains, NJ (US); James R. Tata, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1388 days.

(21) Appl. No.: 11/886,136

(22) PCT Filed: Mar. 17, 2006

(86) PCT No.: PCT/US2006/009694
§ 371 (c)(1),
(2), (4) Date: Sep. 11, 2007

(87) PCT Pub. No.: WO2006/102067
PCT Pub. Date: Sep. 28, 2006

(65) Prior Publication Data
US 2008/0161347 A1   Jul. 3, 2008

Related U.S. Application Data

(60) Provisional application No. 60/663,846, filed on Mar. 21, 2005.

(51) Int. Cl.
*A01N 43/40* (2006.01)
*A01N 43/64* (2006.01)
*A01N 37/44* (2006.01)
*A61K 31/41* (2006.01)
*C07D 213/00* (2006.01)
*C07D 293/00* (2006.01)
*C07D 207/00* (2006.01)
*C07C 61/00* (2006.01)
*C07C 63/00* (2006.01)
*C07C 321/00* (2006.01)
*C07C 323/00* (2006.01)

(52) U.S. Cl. ........ 514/277; 514/359; 514/381; 514/563; 546/1; 548/100; 548/400; 562/400; 562/405; 562/427

(58) Field of Classification Search .......... None
See application file for complete search history.

(56) References Cited

U.S. PATENT DOCUMENTS

| | | | |
|---|---|---|---|
| 5,776,954 A | 7/1998 | deLaszlo et al. | |
| 5,965,741 A | 10/1999 | Breault et al. | |
| 6,881,746 B2 * | 4/2005 | Lau et al. | 514/365 |
| 7,625,938 B2 * | 12/2009 | Brockunier et al. | 514/406 |
| 7,816,557 B2 * | 10/2010 | Conner et al. | 562/450 |
| 7,989,457 B2 * | 8/2011 | Chappell et al. | 514/256 |
| 2008/0125468 A1 * | 5/2008 | Chappell et al. | 514/357 |

FOREIGN PATENT DOCUMENTS

| | | |
|---|---|---|
| CA | 2 569 459 A1 | 12/2005 |
| JP | 2003146972 * | 5/2003 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 99/01423 | 1/1999 |
| WO | WO 99/32448 | 7/1999 |
| WO | WO 00/39088 | 7/2000 |
| WO | WO 00/69810 | 11/2000 |
| WO | WO 02/00612 | 1/2002 |
| WO | WO 02/40444 | 5/2002 |
| WO | WO 03/048109 | 6/2003 |
| WO | WO 03/051357 | 6/2003 |
| WO | WO 03/053938 | 7/2003 |
| WO | WO 03/064404 | 8/2003 |
| WO | WO 03/087619 | 11/2003 |
| WO | WO 2004/002480 | 1/2004 |
| WO | WO 2004/050039 | 6/2004 |
| WO | WO 2004/056763 | 7/2004 |
| WO | WO 2004/062663 | 7/2004 |
| WO | WO 2004/069158 | 8/2004 |

OTHER PUBLICATIONS

Anthony L. Handlon et al., "Glucagon Receptor Antagonists for the Treatment of Type 2 Diabetes", MEDI-164, 226th ACS National Meeting, New York, Sep. 7-11, 2003.

R. Kurukulasuriya et al., "Biaryl amide glucagon receptor antagonists", Bioorganic & Medicinal Chemistry Letters, vol. 14, pp. 2047-2050 (2004).

* cited by examiner

*Primary Examiner* — Alton Pryor
(74) *Attorney, Agent, or Firm* — Anna L. Cocuzzo; Richard C. Billups; John C. Todaro

(57) ABSTRACT

Substituted aryl and heteroaryl derivatives are disclosed. The compounds are useful for treating type 2 diabetes and related conditions. Pharmaceutical compositions and methods of treatment are also included.

15 Claims, No Drawings

SUBSTITUTED ARYL AND HETEROARYL DERIVATIVES, COMPOSITIONS CONTAINING SUCH COMPOUNDS AND METHODS OF USE

CROSS-REFERENCE TO RELATED APPLICATIONS

This application is a U.S. National Phase application under 35 U.S.C. §371 of PCT Application No. PCT/US2006/009694, filed Mar. 17, 2006, which claims priority under 35 U.S.C. §119 from U.S. provisional application No. 60/663,846, filed Mar. 21, 2005.

BACKGROUND OF THE INVENTION

The present invention relates to substituted aryl and heteroaryl derivatives, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level >126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure >130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by (alpha cells in pancreatic islets in response to failing blood glucose levels, The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of glucagon are useful in improving insulin responsiveness in the liver, decreasing the rate of gluconeogenesis and lowering the rate of hepatic glucose output resulting in a decrease in the levels of plasma glucose.

SUMMARY OF THE INVENTION

The present invention is directed to a compound represented by formula I:

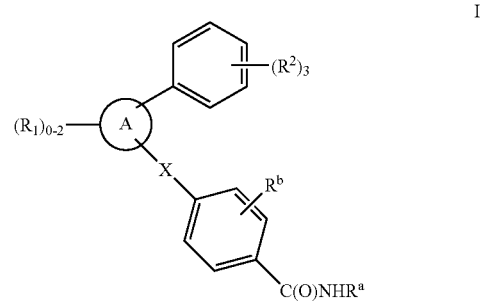

or a pharmaceutically acceptable salt or solvate thereof, wherein:

Ring A represents a 6-10 membered Aryl or heteroaryl group containing 1-2 N atoms, or a 6 membered Aryl group fused to a 5-6 membered carbocyclic ring;

zero to two $R^1$ groups are present and when present are selected from the group consisting of:
(a) halo, OH, $CO_2R^4$, $SO_pR^5$, CN, $NO_2C(O)NR^6R^7$ or $NR^6R^7$;
(b) $C_{1-6}$alkyl, $C(O)C_{1-6}$alkyl or $OC_{1-6}$alkyl, the alkyl portions being optionally substituted with: (1) 1-5 halo groups, up to perhalo, and 1-2 groups selected from OH, $CO_2R^4$, $SO_pR^5$, CN, $NO_2C(O)NR^6R^7$ and $NR^6R^7$
(c) a 6-10 membered aryl, aryloxy or arylthio group, or a 5-10 membered heteroaryl, heteroaryloxy or heteroarylthio group containing 1-2 nitrogen and 0-1 O or S atoms, said aryl and heteroaryl group, and the aryl and heteroaryl portions of aryloxy, arylthio, heteroaryloxy and heteroarylthio being optionally substituted with 1-3 groups selected from (a) and (b) above, said group (c) being further optionally substituted with a member selected from the group consisting of pyrazole, imidazole, tetrazole, pyrrole, triazole, thiazole, furan, thiophene, thiadiazole and oxazole, said group being further optionally substituted with 1-2 group selected from (a) and (b) above;

each $R^2$ is H or is selected from (a) and (b) as defined above;

X is selected from the group consisting of: —O—, —S—, —$(C(R^3)_2)_{1-2}$—, —$OC(R^3)_2$—$C(R^3)_2O$—;

$R^3$ is H, $C_{1-10}$alkyl, $C_{2-4}$alkenyl, Aryl or heteroaryl, said Aryl and heteroaryl being optionally substituted with 1-2 of (a) and (b) above, with no more than one $R^3$ group being other than H and $C_{1-10}$alkyl, $R^4$ is H or $C_{1-6}$alkyl, and $R^5$ represents a member selected from the group consisting of: $C_{1-10}$alkyl, Aryl or Ar—$C_{1-10}$alkyl;

$R^6$ and $R^7$ each independently represent H or $C_{1-3}$alkyl;

p is 0, 1 or 2.

$R^a$ represents $CH_2CH_2CO_2R^4$, $CH_2CH(OH)CO_2R^4$ or 5-tetrazolyl; and $R^b$ is H or is selected from (a) and (b) above.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, unless otherwise specified, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2, 3-b)pyridyl, benzoxazinyl, tetrahydrohydroquinolinyl, tetrahydroisoquinolinyl, dihydroindolyl, and the like The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine.

In one aspect, the invention described herein relates to a compound represented by formula I:

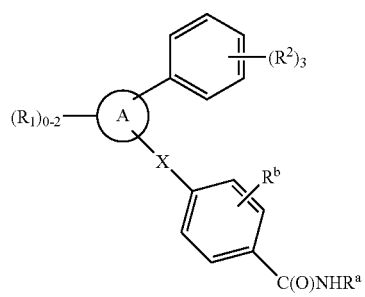

or a pharmaceutically acceptable salt or solvate thereof, wherein:

Ring A represents a 6-10 membered Aryl or heteroaryl group containing 1-2 N atoms, or a 6 membered Aryl group fused to a 5-6 membered carbocyclic ring;

zero to two $R^1$ groups are present and when present are selected from the group consisting of:

(a) halo, OH, $CO_2R^4$, $SO_pR^5$, CN, $NO_2C(O)NR^6R^7$ or $NR^6R^7$;

(b) $C_{1-6}$alkyl, $C(O)C_{1-6}$alkyl or $OC_{1-6}$alkyl, the alkyl portions being optionally substituted with: (1) 1-5 halo groups, up to perhalo, and 1-2 groups selected from OH, $CO_2R^4$, $SO_pR^5$, CN, $NO_2C(O)NR^6R^7$ and $NR^6R^7$ (c) a 6-10 membered aryl, aryloxy or arylthio group, or a 5-10 membered heteroaryl, heteroaryloxy or heteroarylthio group containing 1-2 nitrogen and 0-1 O or S atoms, said aryl and heteroaryl group, and the aryl and heteroaryl portions of aryloxy, arylthio, heteroaryloxy and heteroarylthio being optionally substituted with 1-3 groups selected from (a) and (b) above, said group (c) being further optionally substituted with a member selected from the group consisting of pyrazole, imidazole, tetrazole, pyrrole, triazole, thiazole, furan, thiophene, thiadiazole and oxazole, said group being further optionally substituted with 1-2 group selected from (a) and (b) above;

each $R^2$ is H or is selected from (a) and (b) as defined above;

X is selected from the group consisting of: —O—, —S—, —$(C(R^3)_2)_{1-2}$—, —$OC(R^3)_2$—$C(R^3)_2O$—;

$R^3$ is H, $C_{1-10}$alkyl, $C_{2-4}$alkenyl, Aryl or heteroaryl, said Aryl and heteroaryl being optionally substituted with 1-2 of (a) and (b) above, with no more than one $R^3$ group being other than H and $C_{1-10}$alkyl, $R^4$ is H or $C_{1-6}$alkyl, and $R^5$ represents a member selected from the group consisting of: $C_{1-10}$alkyl, Aryl or Ar—$C_{1-10}$alkyl;

$R^6$ and $R^7$ each independently represent H or $C_{1-3}$alkyl;

p is 0, 1 or 2.

$R^a$ represents $CH_2CH_2CO_2R^4$, $CH_2CH(OH)CO_2R^4$ or 5-tetrazolyl; and $R^b$ is H or is selected from (a) and (b) above.

Another aspect of the invention that is of interest relates to a compound of formula I or a pharmaceutically acceptable salt or solvate thereof wherein ring A is selected from the group consisting of: phenyl, naphthyl, dihydroindenyl, tetrahydronaphthyl, indolyl, isoindolyl and pyridyl. Within this subset of the invention, all other variables are as previously defined.

Another aspect of the invention that is of more interest relates to a compound of formula I or a pharmaceutically acceptable salt or solvate thereof wherein ring A is selected from the group consisting of phenyl, naphthyl, pyridyl and tetrahydronaphthyl. Within this subset of the invention, all other variables are as previously defined.

Another aspect of the invention that is of even more interest relates to a compound of formula I or a pharmaceutically acceptable salt or solvate thereof wherein ring A is selected from the group consisting of phenyl, naphthyl and pyridyl. Within this subset of the invention, all other variables are as previously defined.

Another aspect of the invention that is of interest relates to a compound of formula I or a pharmaceutically acceptable salt or solvate thereof wherein 1-2 $R^1$ groups are present and are selected from the group consisting of: halo, $C_{1-6}$alkyl, CN, halo$C_{1-6}$alkyl, OH, O—$C_{1-6}$alkyl, phenyl, naphthyl, indolyl, imidazolyl, pyrazolyl, pyrimidinyl and O-phenyl, said phenyl, naphthyl, indolyl, imidazolyl, pyrazolyl, pyrimidinyl and O-phenyl being optionally substituted with 1-3 groups selected from: halo, CN, O$C_{1-6}$alkyl, Ohalo$C_{1-6}$alkyl, $CO_2C_{1-6}$alkyl, $CO_2H$, C(O)$C_{1-6}$alkyl, $SO_2C_{1-6}$alkyl, $NO_2$, C(O)$NR^6R^7$ and pyrazolyl. Within this subset of the invention, all other variables are as previously defined.

Another aspect of the invention that is of interest relates to a compound of formula I or a pharmaceutically acceptable salt or solvate thereof wherein each $R^2$ is selected from the group consisting of: H, halo, $C_{1-6}$alkyl, halo$C_{1-6}$alkyl, O$C_{1-6}$alkyl and Ohalo$C_{1-6}$alkyl. Within this subset of the invention, all other variables are as previously defined.

Another aspect of the invention that is of interest relates to a compound of formula I or a pharmaceutically acceptable salt or solvate thereof wherein each $R^2$ is selected from the group consisting of: H, Cl, F, OMe, OEt, O-n-propyl, O-i-propyl, O-n-butyl, O-t-butyl, $CF_3$ and $OCF_3$. Within this subset of the invention, all other variables are as previously defined.

Another aspect of the invention that is of interest relates to a compound of formula I or a pharmaceutically acceptable salt or solvate thereof wherein X represents —$C(R^3)_2)_{1-2}$—, —O$C(R^3)_2$—, or —$C(R^3)_2$O—, wherein $R^3$ is independently selected from H, $C_{1-10}$alkyl, Aryl and HAR, said Aryl and HAR being optionally substituted with 1-2 halo, CN, $C_{1-6}$alkyl, O$C_{1-6}$alkyl, halo$C_{1-6}$alkyl and O-halo$C_{1-6}$alkyl groups. Within this subset of the invention, all other variables are as previously defined.

Another aspect of the invention that is of interest relates to a compound of formula I or a pharmaceutically acceptable salt or solvate thereof wherein $R^a$ represents —$CH_2CH_2CO_2R^4$. Within this subset of the invention, all other variables are as previously defined.

Another aspect of the invention that is of interest relates to a compound of formula I or a pharmaceutically acceptable salt or solvate thereof wherein $R^a$ represents —$CH_2CH_2CO_2R^4$ and $R^4$ represents H. Within this subset of the invention, all other variables are as previously defined.

Another aspect of the invention that is of interest relates to a compound of formula I or a pharmaceutically acceptable salt or solvate thereof wherein $R^b$ represents H. Within this subset of the invention, all other variables are as previously defined.

Another aspect of the invention that is of interest relates to a compound of formula I or a pharmaceutically acceptable salt or solvate thereof wherein:

ring A is selected from the group consisting of: phenyl, naphthyl, dihydroindenyl, tetrahydronaphthyl, indolyl, isoindolyl and pyridyl;

1-2 $R^1$ groups are present and are selected from the group consisting of: halo, $C_{1-6}$alkyl, CN, halo$C_{1-6}$alkyl, OH, O—$C_{1-6}$alkyl, phenyl, naphthyl, indolyl, imidazolyl, pyrazolyl, pyrimidinyl and O-phenyl, said phenyl, naphthyl, indolyl, imidazolyl, pyrazolyl, pyrimidinyl and O-phenyl being optionally substituted with 1-3 groups selected from: halo, CN, O$C_{1-6}$alkyl, Ohalo$C_{1-6}$alkyl, $CO_2C_{1-6}$alkyl, $CO_2H$, C(O)$C_{1-6}$alkyl, $SO_2C_{1-6}$alkyl, $NO_2$, C(O)$NR^6R^7$ and pyrazolyl;

each $R^2$ is selected from the group consisting of: H, halo, $C_{1-6}$alkyl, O$C_{1-6}$alkyl and Ohalo$C_{1-6}$alkyl;

X represents —$(C(R^3)_2)_{1-2}$—, —O$(C(R^3)_2)$—, or —$C(R^3)_2$O—, wherein $R^3$ is independently selected from H, $C_{1-10}$alkyl, Aryl and HAR, said Aryl and HAR being optionally substituted with 1-2 halo, CN, $C_{1-6}$alkyl, O$C_{1-6}$alkyl, halo$C_{1-6}$alkyl and O-halo$C_{1-6}$alkyl groups;

$R^a$ represents —$CH_2CH_2CO_2R^4$ and $R^4$ represents H, and $R^b$ represents H. Within this subset of the invention, all other variables are as previously defined.

Another aspect of the invention that is of particular interest relates to the compounds of formula I shown in the examples and tables contained herein.

Another aspect of the invention that is of interest relates to a pharmaceutical composition comprising a compound as described above with respect to formula I in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I in an amount that is effective to treat type 2 diabetes mellitus.

Another aspect of the invention that is of interest relates to a method of delaying the onset of type 2 diabetes mellitus in a mammalian patient in need thereof, comprising administering to the patient a compound as described above in accordance with formula I in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I as described above.

Another aspect of the invention that is of interest relates to a method of treating obesity in a mammalian patient in need of such treatment comprising administering to said patient a compound in accordance with formula I as described above in an amount that is effective to treat obesity.

Another aspect of the invention that is of interest relates to a method of treating Syndrome X in a mammalian patient in need of such treatment, comprising administering to said patient a compound in accordance with formula I as described above in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I in an amount that is effective to treat said lipid disorder.

Another aspect of the invention that is of interest relates to a method of treating atherosclerosis in a mammalian patient in need of such treatment, comprising administering to said patient a compound in accordance with formula I as described above in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above in an amount that is effective to treat said condition.

Another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above in an amount that is effective to delay the onset of said condition.

Another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, and a compound selected from the group consisting of:

(a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ideal bile acid transporter inhibitor; (n) anti-inflammatory agents excluding glucocorticoids; and (O) protein tyrosine phosphatase-1B (PTP-IB) inhibitors, said compounds being administered to the patient in amounts that are effective to treat said condition.

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of lovastatin, simvastatin, pravastatin, fluvastatin, atorvastatin, itavastatin, ZD-4522 and rivastatin.

Another aspect of the invention that is of interest relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment therapeutically effective amounts of a compound of formula I as described above and an HMG-CoA reductase inhibitor.

Another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin.

Even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin selected from the group consisting of: lovastatin, simvastatin, pravastatin, fluvastatin, atorvastatin, itavastatin, ZD-4522 and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin.

Another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a pharmaceutical composition comprising (1) a compound of formula I as described above; (2) a compound selected from the group consisting of: (a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics and GLP-1 receptor agonists; (h) GIP, GIP mimetics and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA: cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; and (3) a pharmaceutically acceptable carrier.

Optical Isomers-Geometric Isomers-Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

This invention relates to a method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 2.0 g per day, preferably about 1 mg to about 500 mg, in single or divided doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet contains from about 1 mg to about 1.0 g of the active ingredient and each cachet or capsule contains from about 1 to about 500 mg of the active ingredient.

The following are examples of pharmaceutical dosage forms containing a compound of Formula I:

| Injectable Suspension (im.) | mg/mL | Tablet | Mg/tablet |
|---|---|---|---|
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.35 |
| Benzalkonium chloride | 1.0 | Magnesium Stearate | 2.5 |
| Water for injection | t.d. 1.0 mL | Total | 500 mg |

| Capsule | mg/capsule | Aerosol | Per Canister |
|---|---|---|---|
| Compound of Formula 1 | 25.0 | Compound of Formula 1 | 250 mg |

| Capsule | mg/capsule | Aerosol | Per Canister |
|---|---|---|---|
| Lactose | 735 | Lecithin, NF Liq. Conc. | 1.2 mg |
| Mg Stearate | 1.5 | Trichloromethane, NF | 4.025 g |
| Total | 600 mg | Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, (g) LXR modulators and (h) insulin secretagogues (e.g., acetohexamide, carbutamide, chlorpropamide, glibornuride, gliclazide, glimepiride, glipizide, gliquidone, glisoxepide, glyburide, glyhexamide, glycinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include: (1) a compound according to formula I, (2) a compound selected from the group consisting of: (a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) a glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (O) protein tyrosine phosphatase-1B (PTP-1B) inhibitors; and (3) a pharmaceutically acceptable carrier.

The compounds of formula I can be synthesized in accordance with the general schemes provided below, taking into account the specific examples that are provided. Throughout the synthesis schemes, abbreviations are used with the following meanings unless otherwise indicated:

| | |
|---|---|
| AcOH = acetic acid | BOP = benzotriazol-1-yloxy-tris(dimethylamino)-phosphonium hexafluorophosphate |
| Bu = butyl, t-Bu = t-butyl | Bn and Bnzl = benzyl |
| BOC, Boc = t-butyloxycarbonyl | CBZ, Cbz = Benzyloxycarbonyl |
| DCC = Dicyclohexylcarbodiimide | DCM = dichloromethane |
| DIEA = diisopropylethylamine | DIAD = diisopropylazodicarboxylate |
| DMAP = 4-Dimethylaminopyridine | DME = Dimethoxyethane |
| EtOAc = ethyl acetate | DMF = N,N-dimethylformamide |
| eq. = equivalent(s) | EtOH = ethanol |
| Py, Pyr = pyridyl | THF = Tetrahydrofuran |
| HMPA = Hexamethylphosphoramide | FAB-mass spectrum = Fast atom bombardment- mass spectroscopy |
| HOAc = acetic acid | HPLC = High pressure liquid chromatography |
| HOBT, HOBt = Hydroxybenztriazole | IPA = isopropyl alcohol |
| Me = methyl | LAH = Lithium aluminum hydride |
| LDA = lithium diisopropylamide | LHMDS = lithium hexamethyl disilazide |
| PBS = phosphate buffer saline | MeOH = methanol |
| Ph = phenyl | TFA = Trifluoroacetic acid |
| $C_6H_{11}$ = cyclohexyl | $NMe_2$ = dimethylamino |
| iPr = isopropyl | 2ClPh = 2-chlorophenyl |
| 2,4-diClPh = 2,4-dichlorophenyl | |

Compounds of the present invention may be prepared according to the methodology outlined in the following general synthetic schemes.

In one embodiment of the present invention, the compound I may be prepared from the ester 1a by the sequence depicted in Scheme 1. Saponification of ester 1a is achieved with a base such as aqueous lithium hydroxide (LiOH) or sodium hydroxide in a polar solvent such as tetrahydrofuran, methanol (MeOH), ethanol or a mixture of similar solvents. The carboxylic acid product is coupled with an amine, generally a beta alanine derivative 3 or a 5-aminotetrazole 2, using benzotriazol-1-yloxy-tris(dimethylamino)-phosphonium hexafluorophosphate (BOP) and a base, generally diisopropylethylamine (DIEA), in a solvent such as N,N-dimethylformamide or dichloromethane for 1 to 48 hours at ambient temperature to yield compound I. Other peptide coupling conditions may also be used. The beta alanine ester may be converted to a beta alanine acid using aqueous base (v.s.). Compounds containing a t-butyl beta alanine ester are converted to beta alanine acids using an acid such as trifluoroacetic acid in a solvent such as dichloromethane. The product is purified from unwanted side products by recrystallization, trituration, preparative thin layer chromatography, flash chromatography on silica gel as described by W. C. Still et al, *J. Org. Chem.* 1978 43, 2923, or HPLC. Compounds purified by HPLC may be isolated as the corresponding salt. Purification of intermediates is achieved in the same manner.

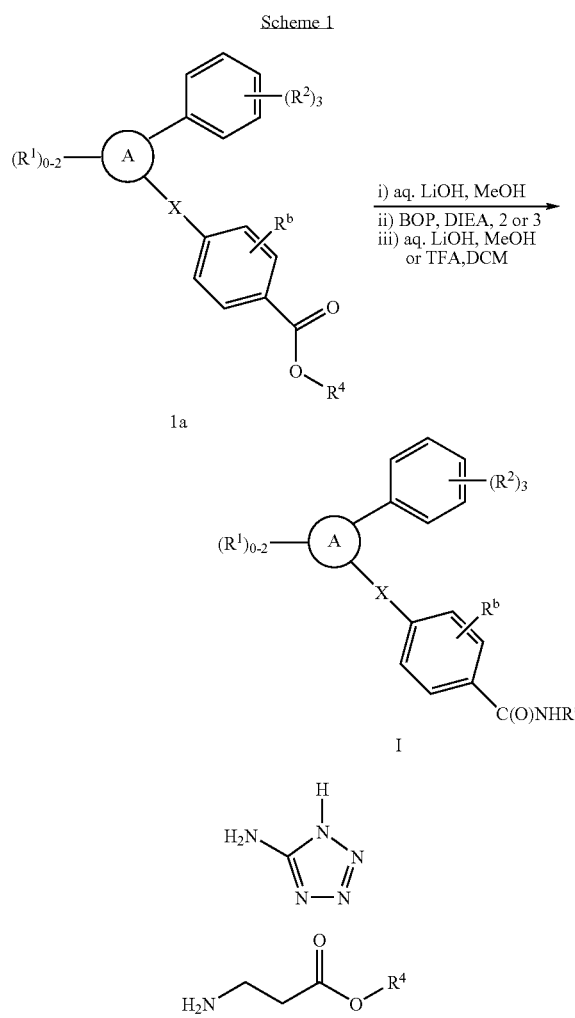

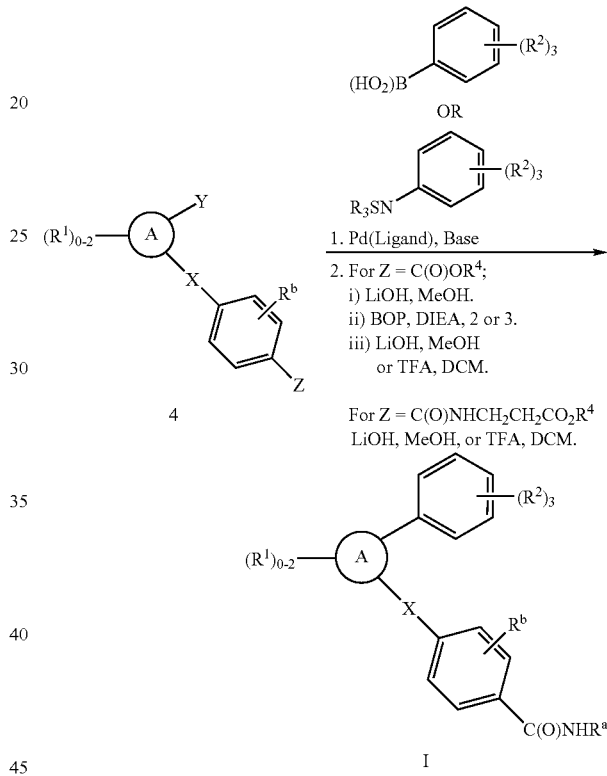

Y = Cl, Br, I, OTf
Z = C(O)OR⁴, C(O)NHRᵃ

In another embodiment of the present invention, compound I may be prepared by the Suzuki coupling of compound 4 with aryl boronic acids as depicted in Scheme 2. Aryl boronic acids are commercially available or may be prepared as described in *J. Org. Chem.* 1995, 60, 7508 and references therein. The Suzuki coupling may be achieved using a variety of conditions (see *Chem. Rev.* 1995, 95, 2457). Typically, the reaction is carried out using tetrakis(triphenylphosphonium) palladium(0) catalyst and a base such as aqueous sodium carbonate or potassium carbonate in a solvent such as dimethoxyethane, tetrahydrofuran or toluene at 50° C. to 100° C. The Suzuki coupling with the less reactive aryl chlorides may also be achieved using a variety of conditions (see *J. Am. Chem. Soc.* 2000, 122, 4020 and references therein). The reaction is usually done using palladium acetate and 2-(dicyclohexylphosphino)biphenyl catalyst and a base such as anhydrous potassium phosphate in toluene at 100° C. as described in *J. Am. Chem. Soc.* 1999, 121, 9550. Alternatively, the preparation of compound I from compound 4 can be achieved by Stille coupling with an aryl stannane (see *J. Am. Chem. Soc.* 1987, 109, 5478 and references therein). Additional steps are required for the conversion of 4 to compound I in cases where the starting material 4 does not possess a Z=CONH(5-tetrazolyl) or a Z=CONHCH$_2$CH$_2$CO$_2$H. For compound 4 where Z=C(O)OR⁴ the Suzuki products are converted to I by base hydrolysis followed by BOP coupling with 2 or 3 as described previously. For compound 4 where Z=CONHCH$_2$CH$_2$CO$_2$R⁴ the Suzuki products are converted to I by either acid or base hydrolysis (v. s.). Intermediates possessing a Y=Cl, Br, and which are not commercially available, may be prepared from the corresponding aniline by a Sandmeyer reaction. The aniline precursors may be prepared by reduction of the corresponding nitro compounds. Intermediates possessing a Y=OTf (triflate) are typically prepared from the corresponding Y=OMe in two steps: cleavage of the methyl ether with boron tribromide followed by treatment with a triflating agent such as trifluoromethanesulfonic anhydride.

The following schemes describe the preparation of intermediates which may be converted to compound I as described in Schemes 1 and 2. The substituent Y' in Scheme 3 and all subsequent schemes may represent a Ph(R²)$_3$ as shown in formula I or a suitable precursor (e.g. Br, Cl, I, NH$_2$, OTf, OMe, OH).

Compound 8, which is an intermediate of compound I wherein X is —CH(R³)CH$_2$—, may be prepared from carbonyl 5, Scheme 3. Carbonyl 5 may be commercially available or may be prepared by a variety of methods familiar to those skilled in the art. One such method is the oxidation of the corresponding alcohol. The preparation of olefin 7 is achieved by Wittig coupling of carbonyl 5 and the commercially available phosphonium chloride (or bromide) 6 in an aprotic solvent such as tetrahydrofuran, dimethylformamide, dimethylacetamide or dimethylsulfoxide at ambient temperature to 100° C. The in-situ generated phosphorous ylide is generated from 6 using a base such as sodium t-butoxide. Other bases may also be used. The olefin 7 is reduced to compound 8 using hydrogen, typically at atmospheric pressure or up to 50 psi, and a catalyst such as platinum (IV) oxide in a solvent such as dichloromethane or ethyl acetate. Other catalysts such as palladium on carbon may also be used for the reduction provided that the functional groups present are compatible with the conditions. For example, the presence of a bromide would preclude the use of palladium.

Scheme 3

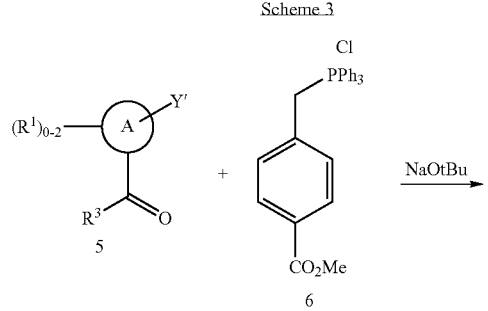

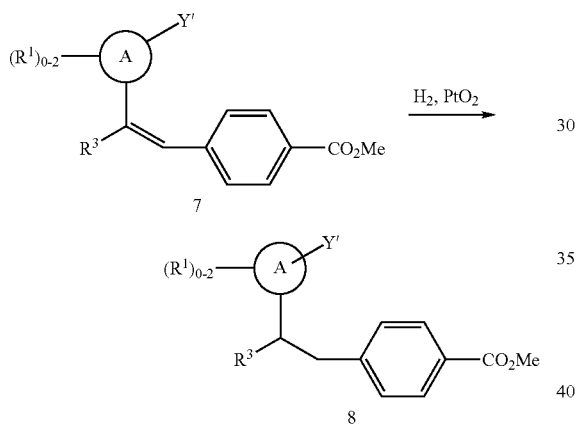

Compound 11, which is an intermediate of compound I wherein X is —CH$_2$CH(R$^3$)—, may be prepared from benzoic acid 9, Scheme 4. The starting materials 9 and 10 are commercially available or may be prepared by a variety of methods familiar to those skilled in the art. Bis-deprotonation of 9 with LDA in a solvent such as tetrahydrofuran and hexamethylphosphoramide at −15° C. to 5° C. followed by treatment with the benzyl halide 10 affords the racemic acid 11 (see Syn. Comm. 1995, 25, 667).

Scheme 4

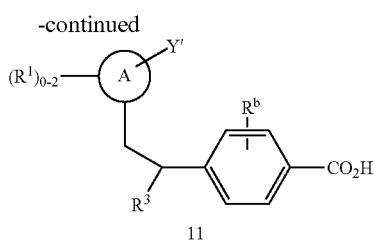

Compound 16, which is an intermediate of compound I wherein X is —CH(R$^3$)CH$_2$— and R$^3$ is indole, may be prepared as depicted in Scheme 5. The preparation of 13 is achieved by the Suzuki coupling of 12 and 3-bromo-3-butene-1-ol (v.s.). Heck coupling (and subsequent double bond migration) of 13 and 14 using palladium acetate catalyst provides the aldehyde 15 (see Tet. Lett. 1989, 30, 6629). Heating aldehyde 15 with phenyl hydrazine and zinc chloride in glacial acetic acid at 80° C. gives the racemic indole 16.

Scheme 5

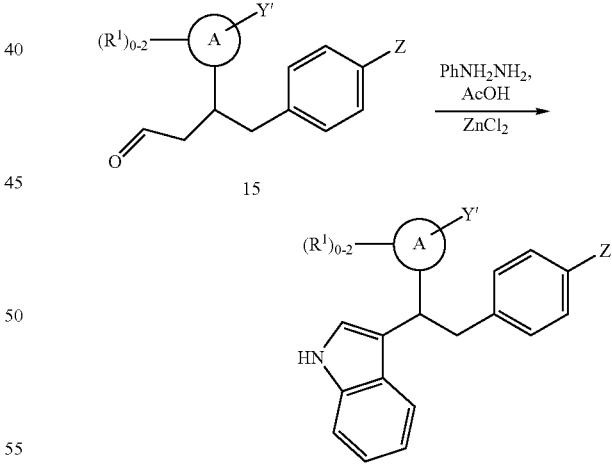

Compound 19a, which is an intermediate of compound I wherein X is —CH(R$^{3'}$)CH(R$^3$)—, wherein R$^{3'}$ is the same as or different than R$^3$, may be prepared from carbonyl 17, Scheme 6. The starting material 17 may be commercially available or may be prepared by a variety of methods familiar to those skilled in the art. One such method involves the palladium catalyzed arylation of ketones as described in J. Am. Chem. Soc. 2000, 122, 1360. Deprotonation of 17 with a base such as LDA, LHMDS or NaOtBu at −78° C. to 0° C.

followed by treatment with benzyl halide 18 affords the alkylated product 19. In the case where R' is CH₃, NaOtBu is preferred for the formation of the internal enolate. It will be recognized by those skilled in the art that this preparation will give racemic products. Additionally, in the case where R³ is not hydrogen, four stereoisomers will be produced. The —COR'— group serves has a precursor for R³' and may be converted to a variety of substituents using methods familiar to those skilled in the art. One such example, where R' is CH₃, is the conversion to a pyrazole by treatment with dimethylformamide dimethyl acetal followed by condensation with hydrazine (see *Synthesis* 2001, 1, 55). In another example, where R' is a 2-F phenyl, is conversion to an indazole by condensation with hydrazine (see *J. Heterocyclic chem.* 1991, 28, 1121).

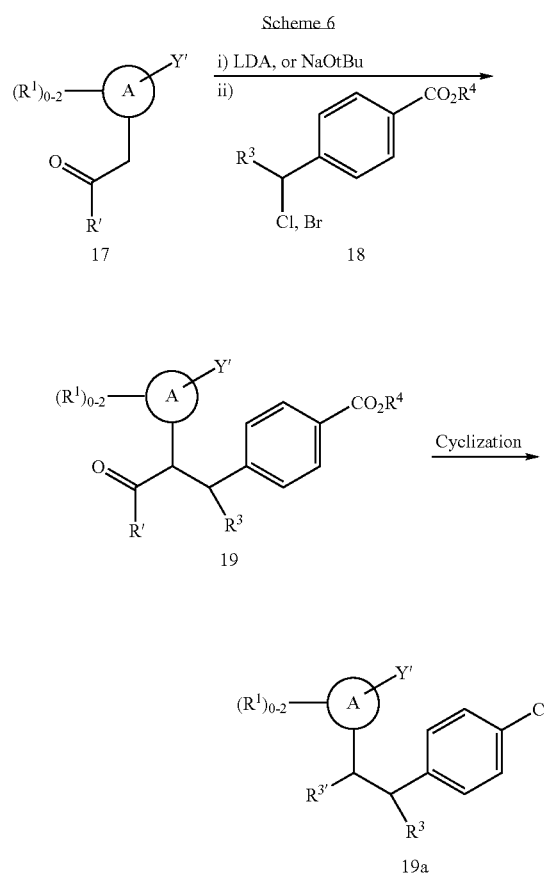

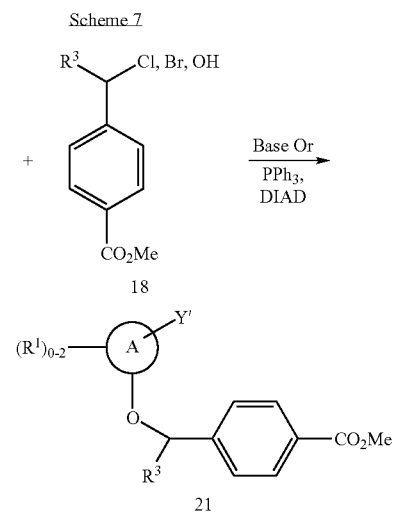

An alternative preparation of intermediate 21 involves the palladium catalyzed coupling of aryl bromides, or chlorides 22 and benzyl alcohol 18 using the procedure described in *J. Am. Chem. Soc.* 2001, 123, 10770. The reaction is achieved by heating 22 and 18 in the presence of palladium acetate and racemic 2-(di-t-butylphosphino)-1,1'-binaphthyl catalyst and cesium carbonate in toluene solvent at 70° C. to 100° C., Scheme 8. In cases where A represents an electron deficient aromatic or heteroaromatic, the preparation of 21 can be achieved by aromatic nucleophilic substitution. This is done by heating 22 and 18 in the presence of a base such as cesium carbonate, potassium carbonate or sodium hydride in an aprotic solvent such as DMF at 50° C. to 150° C.

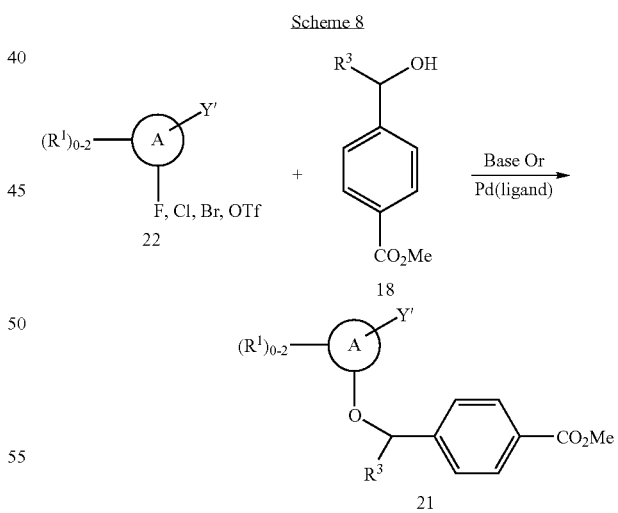

Compound 21, which is an intermediate of compound I wherein X is —OCH(R³)—, may be prepared from phenol 20 and benzoate 18, Scheme 7. The starting materials are commercially available or may be prepared using methods familiar to those skilled in the art. In the case where 18 is a benzyl halide, the preparation of 21 can be achieved by combining 20 and 18 in the presence of a base such as Na₂CO₃, K₂CO₃ or Cs₂CO₃ in a solvent such as DMF, THF, acetone at ambient temperature to 100° C. A wide assortment of conditions is suitable. In the case where 18 is a benzyl alcohol the preparation of 21 can be achieved by Mitsunobu coupling (See Synthesis 1981, 1, 1). This is typically done using triphenyl phosphine and diisopropyl azodicarboxylate in a solvent such as 1,4-dioxane at ambient temperature to 75° C.

Compound 25 which is an intermediate of compound I wherein X is —CH(R³)O—, may be prepared from 23 and methyl 4-hydroxybenzoate 24, Scheme 9. The preparation of 25 from methyl 4-hydroxybenzoate and benzyl alcohol 23 can be achieved using Mitsunobu coupling conditions (v.s.). In the case where 23 is a benzyl halide the preparation of 25 can be achieved using standard alkylation conditions (see compound 21, Scheme 7).

Scheme 9

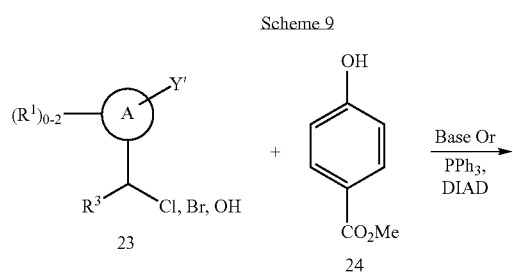

Compound 26, which is an intermediate of compound I wherein X is oxygen, may be prepared by the nucleophilic displacement of aryl halide 22 with methyl 4-hydroxybenzoate 24. The reaction is typically carried out on electron deficient aromatic or heteroaromatic starting materials. The formation of 26 can be achieved by heating 22 and 24 in the presence of a base such as cesium carbonate, potassium carbonate or sodium hydride in an aprotic solvent such as DMF at 50° C. to 150° C.

Scheme 10

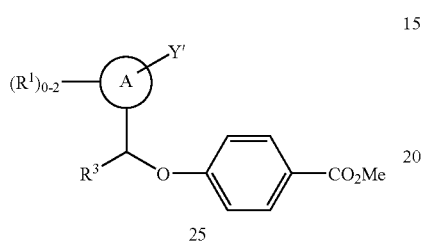

An alternative preparation of intermediate 26 involves the copper mediated coupling of phenol 20 and boronic acid 27. The preparation of 26 is achieved by treatment of phenol 20 and commercially available 27 with copper (II) acetate and triethylamine or pyridine in dichloromethane at ambient temperature as described in *Tet. Lett.* 1998, 39, 2933.

Scheme 11

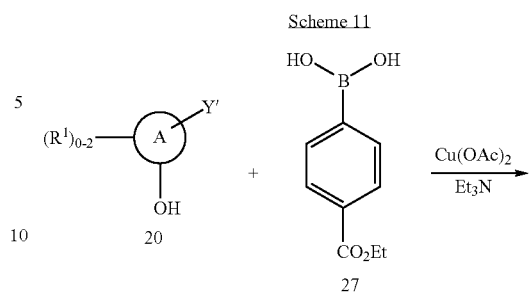

Compound 30, which is an intermediate of compound I wherein X is sulfur, may be prepared from thiophenol 28 and 4-iodobenzoate 29, Scheme 12. The reaction is achieved by heating 28, 29, copper iodide, neocuprine and potassium phosphate in refluxing toluene as described in *Org. Lett.* 2002, 4, 2803.

Scheme 12

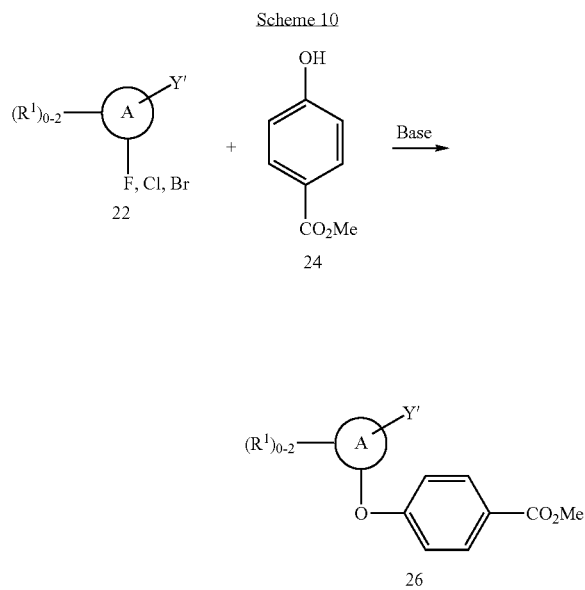

Compounds of formula I, wherein X is CHR$^3$, may be prepared from carbonyl 5, Scheme 13. The aryl Grignard 31 is prepared from the corresponding aryl iodide by treatment with isopropyl magnesium chloride as described in *Synlett* 2001, 12, 1901. Treatment of aryl Grignard 31 with carbonyl 5 in a solvent such as tetrahydrofuran at 0° C. gives the benzyl alcohol 32. Reduction of 32 is achieved with triethylsilane and trifluoroacetic acid in a solvent such as dichloromethane heated at 75° C. to 100° C. in closed vessel. In the case where R$^3$ is alkyl (e.g. methyl, ethyl) a mixture of reduced and dehydrated products will be formed. In these cases the mixture is then reduced with hydrogen at atmospheric pressure and PtO$_2$ catalyst in a solvent such as dichloromethane or ethyl acetate.

Scheme 13

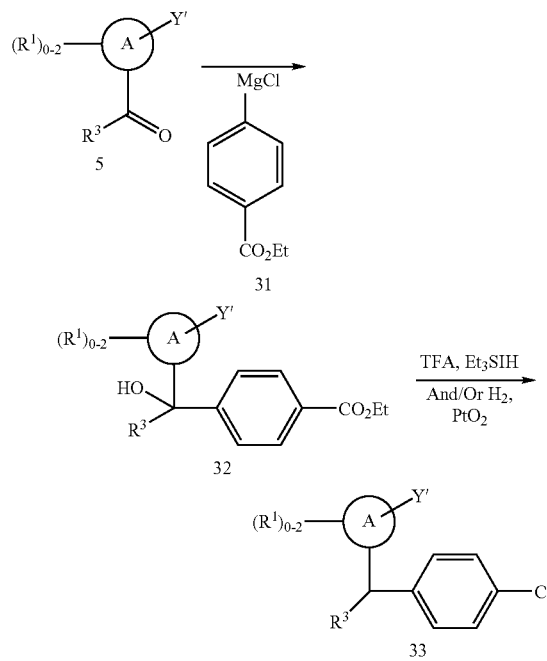

Alternatively, the intermediate 33 may be prepared from 32 ($R^3$=H) by trapping the in-situ generated benzyl cation with a nucleophile ($R^3$) as depicted in Scheme 14. Treatment of 32 with an electron rich aromatic (e.g. indole, anisole, methoxynaphthalene) and an acid such as trifluoracetic acid in dichloromethane solvent at 75° C. to 100° C. gives 33. The reaction can also be achieved using a Lewis acid, such as boron trifluoride, and non-aromatic nucleophiles such allyl trimethyltin or allyl trimethylsilane.

Another preparation of the intermediate 33 ($R^3$=H) is depicted in Scheme 15. Heck coupling of 4-iodo benzoate and olefin 34 using a catalyst such as $Pd(OAc)_2$ and a base such as diisopropylethylamine followed by reduction with hydrogen and platinum oxide catalyst affords 33.

In some cases, the intermediates or products from the reactions described in the previous schemes are further modified; especially with regard to manipulation of the $R^1$ substitutent. These manipulations may include, but are not limited to substitution, reduction, oxidation, alkylation, acylation, and hydrolysis reactions. Compounds possessing an $R^1$ aromatic or heteroaromatic substituent are typically prepared by Suzuki coupling (35, Cl, Br, I, OTf to 36) using the conditions described previously, Scheme 16. The substituent X' represents X-Ph-Z as shown in formula 4 or a suitable precursor to X-Ph-Z as discussed in the previous schemes. Compounds possessing a $R^1$ alkyl ether substituent are typically prepared by Mitsunobu coupling (35 HO to 37 RO) using the conditions described in Scheme 7. Aryl ethers are usually prepared from the phenol 35 HO using the copper mediated coupling described in Scheme 11.

Analytical HPLC mass spectrometry conditions:
LCMS1:
  Column: Waters Xterra MS C-18, 3.5μ, 3.0×50 mm
  Temperature: 40° C.
  Eluent: 10:90 to 98:2 v/v acetonitrile/water+0.05% TFA over 3.75 min.
  Flow Rate: 1.0 mL/min, Injection 10 μL
  Detection: PDA, 200-600 nm
  MS: mass range 150-750 amu; positive ion electrospray ionization
LCMS2:
  Column: Dionex Acclaim C8, 5μ, 4.6×50 mm
  Temperature: 50° C.
  Eluent: 5:95 to 95:5 v/v acetonitrile/water+0.05% TFA over 2.5 min.
  Flow Rate: 2.5 mL/min, Injection 10 μL
  UV: PDA, 200-600 nm
  MS: mass range 150-750 amu; positive ion electrospray ionization
LCMS3:
  Column: Waters Xterra MS-C18, 2.5μ, 4.6×20 mm
  Temperature: 40° C.
  Eluent: 10:90 to 100:0 v/v acetonitrile/water+0.05% TFA over 1.75 min.
  Flow Rate 3 mL/min, Injection 10 μL
  Detection: PDA, 200-600 nm
  MS: mass Range 150-750 amu; positive ion electrospray ionization
Analytical and semi preparative chiral HPLC conditions:
Chiral LC1:
  Column: ChiraCel OJ, 4.6×250 mm
  Temperature: 40° C.
  Eluent: 40% MeOH/CO2+0.1% TFA, 1500 psi outlet pressure
  Flow Rate: 2.11 mL/min
  Detection: PDA, 254 nm
Chiral LC2:
  Column: ChiraCel OD, 4.6×250 mm
  Temperature: 40° C.
  Eluent: 40% MeOH/CO2+0.1% TFA, 1500 psi outlet pressure
  Flow Rate: 2.11 mL/min
  Detection: PDA, 254 nm
Chiral LC3:
  Column: ChiralPak AD, 10μ, 4.6×250 mm
  Temperature: ambient
  Flow Rate: 0.5 mL/min
  Detection: PDA, 254 nm
Chiral LC4:
  Column: ChiralCel OJ, 5μ, 4.6×250 mm
  Temperature: ambient
  Flow Rate: 0.75 mL/min
  Detection: PDA, 254 nm
Preparative reverse phase HPLC(RP-HPLC) conditions:
  Column: Kromasil KR-10C8, 30×100 mm
  Temperature: ambient
  Eluent: 10:90 to 100:0 v/v acetonitrile/water+0.1% TFA over 8.0 min.
  Flow Rate: 50.0 mL/min
  Detection: PDA, 254 nm
Preparative thin layer chromatography (PTLC) was performed on 20×20 cm plates (500 am thick silica gel) using a hexanes/ethyl acetate eluent. Silica gel chromatography was done on a Biotage Horizon flash chromatography system using a hexanes/ethyl acetate gradient.

The following examples are provided so that the invention might be more fully understood. They should not be construed as limiting the invention in any way.

EXAMPLE 1

N-(4-{2-[3-CYANO-4"-(TRIFLUOROMETHOXY)-1,1':4',1"-TERPHENYL-2-YL]ETHYL}BENZOYL)-β-ALANINE

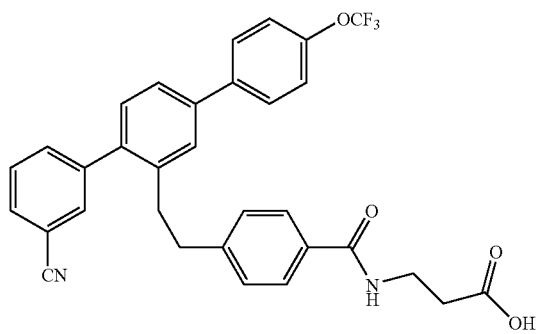

Step A. Methyl 4-amino-4'-(trifluoromethoxy)biphenyl-3-carboxylate

A DME/water solution (40 mL, 3/1) containing methyl 2-amino-5-bromobenzoate (2.5 g, 12.3 mmol), $K_2CO_3$ (4.0 g, 24.6 mmol), 4-(trifluoromethoxy)phenyl boronic acid (3.8 g, 18.5 mmol) and $Pd(PPh_3)_4$ (0.712 g, 0.62 mmol) was heated at 90° C. under an argon atmosphere. After approximately 1 hour the solution was cooled to room temperature and partitioned between water and ethyl acetate. The organic phase was washed with water, brine and dried over $Na_2SO_4$. The solution was filtered, concentrated and the residue purified by silica gel chromatography using a hexanes/ethyl acetate gradient to give the title compound. $^1H$ NMR (500 MHz, $CDCl_3$): δ 8.12 (d, J=2.2 Hz, 1H); 7.57 (d, J=8.5 Hz, 2H); 7.52 (dd, J=2.2, 8.5 Hz, 1H); 7.28 (d, J=8.5 Hz, 2H); 6.77 (d, J=8.5 Hz, 1H); 5.84 (broad s, 2H); 3.94 (s, 3H). LCMS1 3.91 min. (M+H)=312

Step B. Methyl 4-bromo-4'-(trifluoromethoxy)biphenyl-3-carboxylate t-Butyl nitrite (0.976 mL, 8.22 mmol) was added dropwise to solid copper (II) bromide (1.23 g, 5.48 mmol) cooled in an ice bath and under an argon atmosphere. After 5 minutes an acetonitrile solution (25 mL) containing the intermediate from Step A (1.55 g, 4.98 mmol) was added dropwise. The solution was stirred for 2 hours in an ice bath and then allowed to warm to room temperature. The solution was concentrated to a small volume and partitioned between water and ethyl acetate. The organic phase was washed with 15% aqueous $NH_4OH$ (3×), brine and dried over $Na_2SO_4$. The solution was filtered, concentrated and the residue purified by silica gel chromatography using a hexanes/ethyl acetate gradient to give the title compound. LCMS1 4.13 min. (M+H)=375

Step C. [4-Bromo-4'-(trifluoromethoxy)biphenyl-3-yl]methanol

A solution of lithium triethylborohydride (1.0M THF, 10.6 mL) was added dropwise to a THF solution (12 mL) of the intermediate from Step B (2.0 g, 5.33 mmol) cooled in an acetone/ice bath (–10° C.). The solution was stirred at –10° C. until no starting material remained by HPLC (approximately 3 hours). The reaction was quenched with methanol (ca. 10 mL) and concentrated. The residue was partitioned between water and ethyl acetate. The organic phase was washed with water (2×), brine, dried over Na$_2$SO$_4$, filtered and concentrated. The residue was purified by silica gel chromatography using a hexanes/ethyl acetate gradient to give the title compound. $^1$H NMR (500 MHz, CDCl$_3$): δ 7.71 (d, J=2.0 Hz, 1H); 7.64-7.60 (m, 3H); 7.37 (dd, J=2.3, 8.2 Hz, 1H); 7.28-7.33 (m, 2H); 4.84 (s, 2H); 2.09 (s, 1H). LCMS1 3.77 min. (M–H2O)=329

Step D. 4-Bromo-4'-(trifluoromethoxy)biphenyl-3-carbaldehyde

DMSO (0.69 mL, 9.72 mmol) was added dropwise to oxalyl chloride (0.42 mL, 4.86 mmol) in 4 mL DCM at –78° C. After 20 minutes a DCM solution (6 mL) of the intermediate from Step C (1.2 g, 3.47 mmol) was added dropwise. After stirring for 15 minutes at –78° C. triethylamine (2.42 mL, 17.35 mmol) was added. The reaction mixture was then allowed to warm to room temperature. The solution was partitioned between aqueous saturated NH$_4$Cl and DCM. The organic phase was washed with water, brine, dried over Na$_2$SO$_4$, filtered and concentrated. The residue was purified by silica gel chromatography using a hexanes/ethyl acetate gradient to give the title compound. $^1$H NMR (500 MHz, CDCl$_3$): δ 10.43 (s, 1H); 8.12 (d, J=2.4 Hz, 1H); 7.75 (d, J=8.6 Hz, 1H); 7.67-7.65 (m, 1H); 7.63 (d, J=8.5 Hz, 2H); 7.34 (d, J=8.5 Hz, 2H). LCMS1 4.09 min. (M+H)=345

Step E. Methyl 4-{(E,Z)-2-[4-bromo-4'-(trifluoromethoxy)biphenyl-3-yl]vinyl}benzoate A solution of NaOMe (25 wt % in MeOH, 0.63 mL, 2.90 mmol) was added dropwise to a DMF solution (10 mL) of [4-(methoxycarbonyl)benzyl](triphenyl)phosphonium bromide (1.43 g, 2.90 mmol). After stirring at room temperature for 1 hour a DMF solution (ca. 4 mL) of the intermediate from Step D (0.5 g, 1.45 mmol) was added. After 10 minutes the reaction solution was partitioned between water and ethyl acetate. The organic phase was washed with water (5×), brine and dried over Na$_2$SO$_4$. The solution was filtered, concentrated and the residue purified by silica gel chromatography using a hexanes/ethyl acetate gradient to give the title compound as a mixture of E/Z olefin isomers. $^1$H NMR (500 MHz, CDCl$_3$): major isomer δ7.92 (d, J=8.3 Hz, 2H); 7.71 (d, J=8.9 Hz, 1H); 7.34-7.30 (m, 6H); 7.19 (d, J=8.6 Hz, 2H); 6.81 (s, 2H); 3.92 (s, 3H). LCMS1 4.68 min. (M+H)=477

Step F. Methyl 4-{2-[4-bromo-4'-(trifluoromethoxy)biphenyl-3-yl]ethyl}benzoate A DCM solution (40 mL) containing PtO$_2$ (0.810 g, 3.57 mmol) and the intermediate from Step E (8.49 g, 17.84 mmol) was stirred overnight under a hydrogen atmosphere (balloon). The flask was purged with nitrogen and the solution filtered through Celite. The filter cake was washed with DCM (3×) and the filtered solution was concentrated to give the title compound. The crude material was used in the next step without purification. $^1$H NMR (500 MHz, CDCl$_3$): δ 8.01 (d, J=8.1 Hz, 2H); 7.65 (d, J=8.9 Hz, 1H); 7.49 (d, J=8.6 Hz, 2H); 7.31-7.29 (m, 6H); 3.94 (s, 3H); 3.16-3.11 (m, 2H); 3.07-3.02 (m, J=2H). LCMS1 4.72 min. (M+H)=479

Step G. 4-{2-[4-Bromo-4'-(trifluoromethoxy)biphenyl-3-yl]ethyl}benzoic acid

To a THF/MeOH/water solution (ca. 40 mL/40 mL/10 mL) of the intermediate from Step F (8.53 g, 17.84 mmol) was added LiOH (3.66 g, 89.2 mmol). The solution was stirred at 45° C. until no starting material remained by HPLC (ca. 2 hrs). The solution was concentrated to remove the majority of MeOH/THF and then partitioned between aqueous 1N HCl and ethyl acetate. The organic phase was washed with water (2×), brine and dried over Na$_2$SO$_4$. The solution was filtered and concentrated to give the title compound. The crude material was use in the next step without purification.

Step H. Tert-butyl N-(4-{2-[4-bromo-4-(trifluoromethoxy)biphenyl-3-yl]ethyl}benzoyl)-β-alaninate A DMF solution (8 mL) containing the intermediate from Step G (00.921 g, 1.98 mmol), DIEA (1.72 mL, 9.9 mmol), tert-butyl β-alaninate hydrochloride (0.437 g, 2.4 mmol) and BOP (1.32 g, 2.97 mmol) was heated at 45° C. for 1 hour. The solution was partitioned between water and ethyl acetate. The organic phase was washed with water (4×) and brine. The solution was then dried over Na$_2$SO$_4$, filtered and concentrated. The residue was purified by silica gel chromatography using a hexanes/ethyl acetate gradient to give the title compound. $^1$H NMR (500 MHz, CDCl$_3$): δ 7.73 (d, J=8.1 Hz, 2H); 7.65 (d, J=7.8 Hz, 1H); 7.50 (d, J=8.5 Hz, 2H); 7.33-7.26 (m, 6H); 6.99 (t, J=5.8 Hz, 1H); 3.73-3.71 (m, 2H); 3.14-3.09 (m, 2H); 3.07-3.01 (m, 2H); 2.59 (t, J=5.9 Hz, 2H) 1.49 (s, 9H). LCMS1 4.58 min. (M+H)=592

Step I. N-(4-{2-[4-bromo-4'-(trifluoromethoxy)biphenyl-3-yl]ethyl}benzoyl)-β-alanine To the intermediate from Step H was added DCM/TFA (1/1). The solution stirred at room temperature until no starting material remained by HPLC (1 hour). The solution was concentrated to give the title compound. The crude material was used in the next step without purification. LCMS1 4.01 min. (M+H)=536

Step J. N-(4-{2-[3-cyano-4''-(trifluoromethoxy)-1,1': 4':1''-terphenyl-2'-yl]ethyl}benzoyl)-β-alanine A DME/water solution (1/1, 2 mL) containing the intermediate from Step I (23 mg, 0.043 mmol), K$_2$CO$_3$ (12 mg, 0.086 mmol), 3-cyanophenyl boronic acid (10 mg, 0.065 mmol) and Pd(PPh$_3$)$_4$ (5 mg, 0.0043 mmol) was heated at 90° C. under an argon atmosphere. The solution was stirred at 90° C. until no starting material remained by HPLC (ca. 1 hour). The solution was cooled to room temperature and concentrated. The residue was diluted with DMF, filtered and purified by RP-HPLC to give the title compound. $^1$H NMR (500 MHz, CDCl$_3$): δ 7.65-7.63 (m, 5H); 7.53-7.46 (m, 4H); 7.34 (d, J=8.1 Hz, 2H); 7.22 (d, J=7.8 Hz, 2H); 7.03 (broad s, 1H);

6.96 (d, J=8.1 Hz, 2H); 3.77-3.73 (m, 2H); 2.93-2.85 (m, 4H); 2.74 (t, J=5.8 Hz, 2H). LCMS1 4.02 min. (M+H)=559

EXAMPLE 2

N-{4-[({3-[4-(TRIFLUOROMETHOXY)PHENYL]-1-NAPHTHYL}OXY)METHYL]BENZOYL}-β-ALANINE

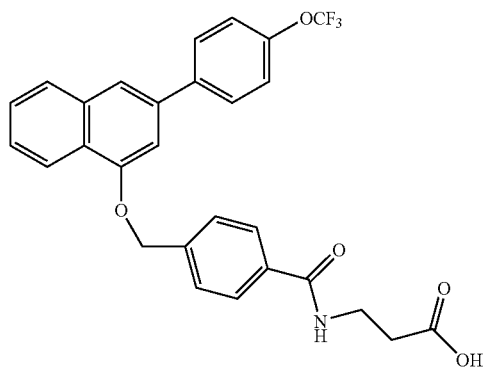

Step A. 4-Hydroxy-2-naphthyl trifluoromethanesulfonate and 3-hydroxy-1-naphthyl trifluoromethanesulfonate Trifluoromethanesulfonic anhydride (0.96 g, 3.4 mmol) and DIEA (0.6 mL, 3.4 mmol) were added dropwise simultaneously to 1,3 dihydroxynaphthalene (0.5 g, 3.1 mmol) in dichloromethane at room temperature. After stirring overnight the solution was partitioned between aqueous 1N hydrochloric acid and ethyl acetate. The organic phase was dried over MgSO$_4$, filtered and concentrated. The residue was purified by silica gel chromatography using a hexanes/ethyl acetate gradient to give title compounds. Data for the faster eluting isomer, 4-hydroxy-2-naphthyl trifluoromethanesulfonate: $^1$H NMR (500 MHz, CDCl$_3$): δ 8.23 (d, J=8.1 Hz, 1H); 7.85 (d, J=7.6 Hz, 1H); 7.64-7.57 (m, 2H); 7.39 (d, J=2.1 Hz, 1H); 6.80 (d, J=2.3 Hz, 1H); 6.08 (s, 1H). Data for the slower eluting isomer, 3-hydroxy-1-naphthyl trifluoromethanesulfonate: $^1$H NMR (500 MHz, CDCl$_3$): δ 8.02 (d, J=8.4 Hz, 1H); 7.75 (d, J=8.1 Hz, 1H); 7.58-7.50 (m, 2H); 7.21 (s, 2H), 5.70 (broad s, 1H). The regiochemistry of the triflation was confirmed by taking a portion of the slower eluting isomer and reducing with 10% Pd/C in ethyl acetate under a hydrogen atmosphere. The proton NMR of the reduced material was identical to the NMR of commercially available 2-naphthol.

Step B. 3-[4-(Trifluoromethoxy)phenyl]-1-naphthol

4-Hydroxy-2-naphthyl trifluoromethanesulfonate (100 mg, 0.34 mmol), 4-(trifluoromethoxy)phenyl boronic acid (0.14 g, 0.68 mmol) and Pd(PPh$_3$)$_4$ (20 mg, 0.017 mmol) in DME/2M K$_2$CO$_3$ (1/1) were heated at reflux under an argon atmosphere. After approximately 2 hours the solution was cooled and partitioned between aqueous 1N hydrochloric acid and ethyl acetate. The organic phase was dried over MgSO$_4$, filtered and concentrated. The residue was purified by silica gel chromatography using a hexanes/ethyl acetate gradient to give the compound. LCMS1 3.94 min. (M+H)= 305

Step C. Methyl 4-[({3-[4-(trifluoromethoxy)phenyl]-1-naphthyl}oxy)methyl]benzoate An acetone solution of 3-[4-(trifluoromethoxy)phenyl]-1-naphthol (50 mg, 0.166 mmol), methyl 4-(bromomethyl)benzoate (73 mg, 0.32 mmol) and K$_2$CO$_3$ (44 mg, 0.32 mmol) was heated at reflux until no starting material remained by HPLC analysis. The solution was concentrated and the residue purified by silica gel chromatography using a hexanes/ethyl acetate gradient to give the title compound. LCMS1 4.64 min. (M+H)=453

Step D. 4-[({3-[4-(Trifluoromethoxy)phenyl]-1-naphthyl}oxy)methyl]benzoic acid

To a THF/MeOH solution (ca. 1/1, 2 mL) of the intermediate from Step C (40 mg, 0.09 mmol) was added LiOH monohydrate (20 mg, 0.49 mmol) in 1 mL water. The solution was stirred at room temperature until no ester remained by HPLC analysis. The solution was concentrated and partitioned between ethyl acetate and aqueous 1N HCl. The organic phase was washed with brine, dried over MgSO$_4$ and filtered. The solution was then concentrated to give the title compound which was used without further purification. LCMS1 4.27 min. (M+H)=439

Step E N-{4-[{3-[4-(trifluoromethoxy)phenyl]-1-naphthyl}oxy)methyl]benzoyl}-β-alanine To a DMF solution (2 mL) of the intermediate from Step D (35 mg, 0.08 mmol) was added tert-butyl β-alaninate hydrochloride (30 mg, 0.16 mmol) DIEA (0.06 mL, 0.35 mmol) and BOP (53 mg, 0.12 mmol). The solution was stirred at room temperature for ca. 30 minutes. The solution was then partitioned between ethyl acetate and aqueous 1N HCl. The organic phase was washed with aqueous 1N HCl (3×), brine; dried over MgSO$_4$ and filtered to give tert-butyl N-{4-[({3-[4-(trifluoromethoxy)phenyl]-1-naphthyl}oxy)methyl]benzoyl}-β-alaninate. LCMS1 4.50 min. (M+H)=566. The tert butyl group was removed by treatment with 1/1 DCM/TFA for 1 hour. The crude acid was purified by reverse phase HPLC to give the title compound. $^1$H NMR (500 MHz, CD$_3$OD): δ 8.57 (s, 1H); 8.31 (d, J=8.1 Hz, 1H); 7.92 (m, 1H); 7.89 (d, J=8.3 Hz, 2H); 7.82 (d, J=8.7 Hz, 2H); 7.70 (m, 3H); 7.56-7.49 (m, 2H); 7.39 (d, J=8.1 Hz, 2H); 7.24 (s, 1H); 5.46 (s, 2H); 3.69-3.65 (m, 2H); 2.68-2.66 (m, 2H). LCMS1 3.97 min. (M+H)=510

INTERMEDIATE 1

TERT-BUTYL N-(4-IODOBENZOYL)-β-ALANINATE

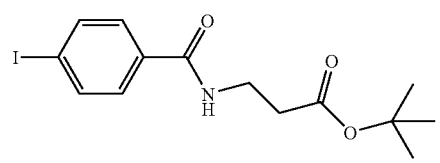

The title compound was prepared from 4-iodobenzoic acid using the procedure described in EXAMPLE 1 Step H. $^1$H NMR (400 MHz, CDCl$_3$): δ 7.77 (d, J=8.5 Hz, 2H); 7.47 (d, J=8.5 Hz, 2H); 6.91 (broad s, 1H); 3.66 (q, J=5.9 Hz, 2H); 2.54 (t, J=5.9 Hz, 2H); 1.45 (s, 9H). LCMS1 3.35 min. (M+H)=376.

EXAMPLES 3A, 3B

N-(4-{2-(1H-INDOL-3-YL)-2-[4'-(TRIFLUO-ROMETHOXY)BIPHENYL-3-YL]ETHYL}BENZOYL)-β-ALANINE

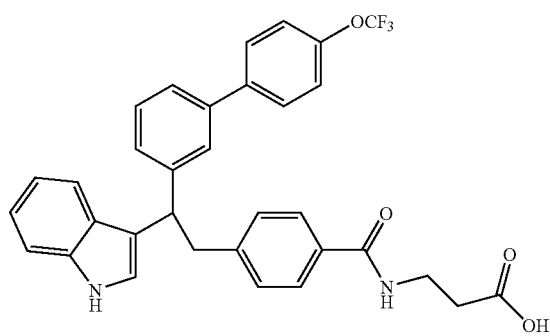

Step A. 3-(3-Chlorophenyl)but-3-en-1-ol

A solution of DME (20 mL) and 2M $Na_2CO_3$ (15 mL) containing 3-bromobut-3-en-1-ol (1.40 g, 7.66 mol), (3-chlorophenyl)boronic acid (2.3 g, 14.7 mmol) and $Pd(PPh_3)_4$ (0.4 g, 0.35 mmol) was refluxed under an argon atmosphere for 3 hours. The solution was concentrated (to remove excess DME) and partitioned between water and ethyl acetate. The organic phase was washed with 1N NaOH, water (2×) and brine. The solution was then dried over $MgSO_4$, filtered and concentrated. The residue was purified by silica gel chromatography using a hexanes/ethyl acetate gradient to give the title compound. $^1$H NMR (500 MHz, $CDCl_3$): δ 7.42 (s, 1H); 7.31-7.29 (m, 3H); 5.43 (s, 1H); 5.21 (s, 1H); 3.73 (t, J=6.5 Hz, 2H); 2.77 (t, J=6.3 Hz, 2H); 1.91 (s, 1H). LCMS1 2.95 min. (M-OH)=165.

Step B. 3-[4'-(Trifluoromethoxy)biphenyl-3-yl]but-3-en-1-ol

A toluene solution (5 mL) containing the intermediate from Step A (441 mg, 2.4 mmol), 4-(trifluoromethoxy)phenyl boronic acid (746 mg, 3.62 mmol), $K_3PO_4$ (865 mg, 4.08 mmol), 2-(dicyclohexylphosphino)biphenyl (68 mg, 0.19 mmol) and $Pd(OAc)_2$ (22 mg, 0.098 mmol) was heated at 100° C. under an argon atmosphere. After 1 hour the solution was partitioned between water and ethyl acetate. The organic phase washed with 1N NaOH, brine, dried over $MgSO_4$ and concentrated. The residue was purified by silica gel chromatography using a hexanes/ethyl acetate gradient to give the title compound. LCMS1 3.71 min. (M+H)=309.

Step C. tert-butyl N-(4-[4-oxo-2-[4'-(trifluoromethoxy)biphenyl-3-yl]butyl]benzoyl)-β-alaninate A DMF solution (4 mL) containing the intermediate from Step B (453 mg, 1.47 mmol), INTERMEDIATE 1 (607 mg, 1.62 mmol), $Bu_4NCl$ (817 mg, 2.94 mmol), LiOAc (242 mg, 3.67 mmol), LiCl (62 mg, 1.47 mmol) and $Pd(OAc)_2$ (17 mg, 0.076 mmol) was stirred overnight at 90° C. under an argon atmosphere. The solution was partitioned between water and ethyl acetate. The organic phase was washed with water (3×), brine and dried over $MgSO_4$. The solution was filtered, concentrated and the residue purified by silica gel chromatography using a hexanes/ethyl acetate gradient to give the title compound. $^1$H NMR (400 MHz, $CDCl_3$): δ 9.67 (s, 1H); 7.63 (d, J=8.2 Hz, 2H); 7.50 (d, J=8.6 Hz, 2H); 7.39-7.33 (m, 2H); 7.29-7.24 (m, 3H); 7.15-7.08 (m, 3H); 6.79 (broad s, 1H); 3.66 (q, J=5.9 Hz, 2H); 3.61-3.55 (m, 1H); 3.03-2.97 (m, 2H); 2.85-2.81 (m, 2H); 2.53 (t, J=5.9 Hz, 2H); 1.42 (s, 9H). LCMS1 4.00 min. (M+H)=500.

Step D. N-(4-{2-(1H-indol-3-yl)-2-[4'-(trifluoromethoxy)biphenyl-3-yl]ethyl}benzoyl)-β-alanine A glacial acetic acid solution (4 mL) containing the intermediate from Step C (150 mg, 0.27 mmol), phenyl hydrazine hydrochloride (51 mg, 0.35 mmol) and $ZnCl_2$ (110 mg, 0.81 mmol) was heated at 80° C. for 1 hour. The solution was concentrated and partitioned between aqueous 1N HCl and ethyl acetate. The organic phase was washed with brine, dried over $MgSO_4$, filtered and concentrated. The residue was purified by RP-HPLC and the isolated material was resolved using chiral OJ SFC-HPLC to give the title compounds. Isomer A: Chiral LC1 4.85 min, LCMS1 3.80 min. (M+H)=572. Isomer B: Chiral LC1 12.09 min, LCMS1 3.80 min. (M+H)=572. Representative $^1$H NMR (400 MHz, $CD_3OD$): δ 7.58 (d, J=8.2 Hz, 2H); 7.47 (d, J=8.6 Hz, 2H); 7.37-7.14 (m, 11H); 7.01 (t, J=7.5 Hz, 1H); 6.85 (t, J=7.5 Hz, 1H); 4.57 (t, J=7.9 Hz, 1H); 3.63 (dd, J=6.7, 13.4 Hz, 1H); 3.56 (t, J=6.9 Hz, 2H); 3.36 (dd, J=9.1, 13.3 Hz, 1H); 2.57 (t, J=7.0 Hz, 2H).

INTERMEDIATE 2

TERT-BUTYL N-{4-[2-(5-BROMO-2-HYDROXYPHENYL)ETHYL]BENZOYL}-β-ALANINATE

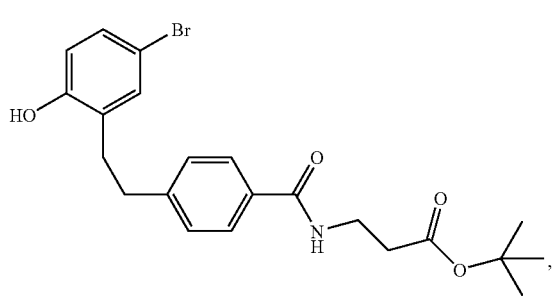

The title compound was prepared from 5-bromo-2-hydroxybenzaldehyde using the chemistry described in EXAMPLE 1. $^1$H NMR (500 MHz, $CD_3OD$): δ 7.70 (t, J=4.1 Hz, 2H); 7.27 (d, J=8.2 Hz, 2H); 7.11-7.07 (m, 2H); 6.68 (d, J=8.4 Hz, 1H); 3.60 (t, J=6.9 Hz, 2H); 2.95-2.83 (m, 4H); 2.56 (t, J=6.9 Hz, 2H); 1.45 (s, 9H). LCMS1 3.65 min. (M+H)= 448

EXAMPLE 4

N-(4-{2-[4-(CYCLOPENTYLOXY)-4'-(TRIFLUOROMETHOXY)BIPHENYL-3-YL]ETHYL}BENZOYL)-β-ALANINE

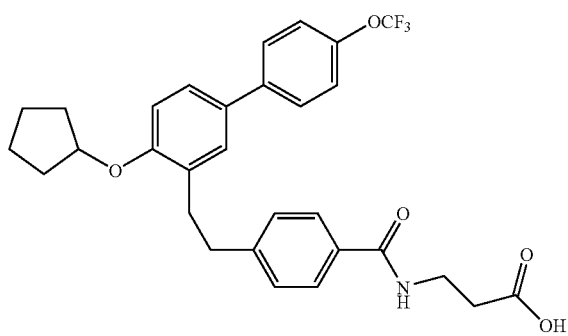

Step A. tert-butyl N-(4-{2-[4-hydroxy-4'-(trifluoromethoxy)biphenyl-3-yl]ethyl}benzoyl)-β-alaninate The title compound was prepared from INTERMEDIATE 2 using the Suzuki conditions described in EXAMPLE 1. LCMS1 4.05 min. (M+H)=530

Step B. N-(4-{2-[4-cyclopentyloxy-4'-(trifluoromethoxy)biphenyl-3-yl]ethyl}benzoyl)-β-alaninate DIAD (0.04 mL, 0.20 mmol) was added to a 1,4-dioxane solution (1 mL) containing the intermediate from Step A (25 mg, 0.047 mmol), triphenylphosphine (50 mg, 0.19 mmol) and cyclopentanol (0.022 mL, 0.24 mmol) heated at 75° C. After stirring overnight at 75° C. the solution was concentrated and the residue purified by PTLC using a hexanes/ethyl acetate mobile phase to give tert-butyl N-(4-{2-[4-(cyclopentyloxy)-4'-(trifluoromethoxy)biphenyl-3-yl]ethyl}benzoyl)-β-alaninate. The tert butyl group was removed with TFA as described in Example 1 Step I and the crude material purified by RP-HPLC to give the title compound. $^{1}$H NMR (500 MHz, CD$_3$OD): δ 7.71 (d, J=8.3 Hz, 2H); 7.56-7.54 (m, 2H); 7.40 (dd, J=2.4, 8.5 Hz, 1H); 7.28-7.23 (m, 5H); 6.99 (d, J=8.6 Hz, 1H); 4.93-4.89 (m, 1H); 3.62 (t, J=6.9 Hz, 2H); 2.95 (broad s, 4H); 2.62 (t, J=6.9 Hz, 2H); 2.02-1.68 (m, 8H). LCMS1 4.29 min. (M+H)=542

EXAMPLE 5

N-[4-(2-{3',4'-DICHLORO-4-[4-(TRIFLUOROMETHOXY)PHENOXY]BIPHENYL-3-YL}ETHYL)BENZOYL]-β-ALANINE

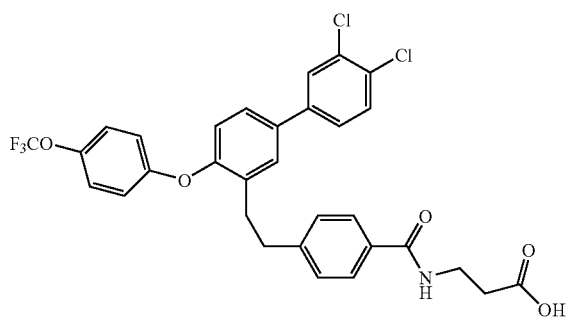

Step A. tert-butyl N-{4-[2-(3',4'-dichloro-4-hydroxybiphenyl-3-yl)ethyl]benzoyl}-β-alaninate The title compound was prepared from INTERMEDIATE 2 using the Suzuki conditions described in EXAMPLE 1 Step A. $^{1}$H NMR (500 MHz, CDCl$_3$): δ 7.72 (d, J=7.9 Hz, 2H); 7.56 (d, J=2.1 Hz, 1H); 7.46 (d, J=7.4 Hz, 1H); 7.33-7.29 (m, 4H); 7.22 (d, J=2.2 Hz, 1H); 7.07-7.01 (m, 1H); 6.90 (dd, J=2.2, 8.2 Hz, 1H); 3.74 (q, J=5.9 Hz, 2H); 3.03-2.99 (m, 4H); 2.61 (t, J=5.8 Hz, 2H) 1.50 (s, 9H). LCMS1 4.14 min. (M+H)= 514

Step B. N-[4-(2-{3',4'-dichloro-4-[4-(trifluoromethoxy)phenoxy]biphenyl-3-yl}ethyl)benzoyl]-β-alanine A DCM solution (1 mL) containing the intermediate from Step A (22 mg, 0.043 mmol), copper(II) acetate (8 mg, 0.043 mmol), 4-(trifluoromethoxy)phenyl boronic acid (18 mg, 0.086 mmol), triethylamine (0.03 mL, 0.215 mmol) and 4 Å molecular sieves (small spatula tip) was stirred under an air atmosphere. After stirring overnight the solution was filtered and concentrated to give tert-butyl N-[4-(2-{3',4'-dichloro-4-[4-(trifluoromethoxy)phenoxy]biphenyl-3-yl}ethyl)benzoyl]-β-alaninate. LCMS1 4.85 min. (M+H)=674. The tert butyl group was cleaved as described in EXAMPLE 1 Step I to give the title compound. $^{1}$H NMR (500 MHz, CDCl$_3$): δ 7.65 (d, J=8.2 Hz, 2H); 7.59 (d, J=2.2 Hz, 1H); 7.51 (d, J=8.3 Hz, 1H); 7.37-7.34 (m, 3H); 7.24 (d, J=8.3 Hz, 2H); 7.21 (d, J=8.4 Hz, 2H); 6.98-6.95 (m, 4H); 3.79 (q, J=5.9 Hz, 2H); 3.01 (s, 4H); 2.80 (t, J=5.8 Hz, 2H). LCMS1 4.43 min. (M+H)= 618.

INTERMEDIATE 3

METHYL 4-{[(3-CHLOROISOQUINOLIN-1-YL)OXY]METHYL}BENZOATE

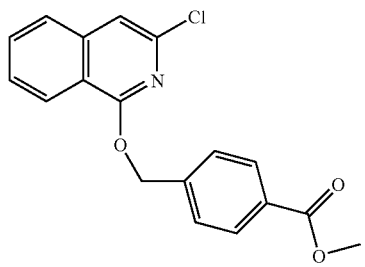

A toluene (3 mL) solution containing 1,3-dichloroisoquinoline (50 mg, 0.25 mmol), 4-(hydroxymethyl)benzoate (105 mg, 0.63 mmol), cesium carbonate (206 mg, 0.63 mmol), palladium acetate (5 mg, 0.02 mmol) and racemic-2-(di-t-butylphosphino)-1,1'-binaphthyl (14 mg, 0.035 mmol) was heated at 75° C. for 1.5 hours. The solution was partitioned between ethyl acetate and water. The organic phase was washed with brine and dried over MgSO$_4$. The solution was filtered, concentrated and the residue purified by silica gel chromatography using hexanes/ethyl acetate gradient. $^{1}$H NMR (500 MHz, CDCl$_3$): δ 8.30 (d, J=8.3 Hz, 1H); 8.13 (d, J=8.3 Hz, 2H); 7.72-7.70 (m, 2H); 7.65 (d, J=8.2 Hz, 2H); 7.59-7.55 (m, 1H); 7.34 (s, 1H); 5.68 (s, 2H); 3.98 (s, 3H). LCMS2 2.73 min. (M+H)=328

INTERMEDIATE 4

RACEMIC METHYL 4-{1-[(3-CHLOROISOQUINOLIN-1-YL)OXY]ETHYL}BENZOATE

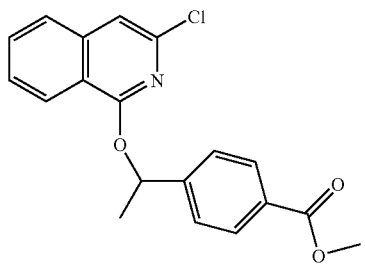

The title compound was prepared from 1,3-dichloroisoquinoline and racemic methyl 4-(1-hydroxyethyl)benzoate as described in the preparation of INTERMEDIATE 3. $^1$H NMR (500 MHz, CDCl$_3$): δ 8.35 (d, J=8.4 Hz, 1H); 8.08 (d, J=8.3 Hz, 2H); 7.72-7.68 (m, 2H); 7.64 (d, J=8.3 Hz, 2H); 7.60-7.56 (m, 1H); 7.31 (s, 1H); 6.56 (q, J=6.6 Hz, 1H); 3.95 (s, 3H); 1.81 (d, J=6.5 Hz, 3H). LCMS1 4.26 min. (M-(CH$_3$CHPhCO2Me)+H)=180

INTERMEDIATE 5

METHYL 4-[(3,6-DICHLOROPYRIDIN-2-YL)METHOXY]BENZOATE

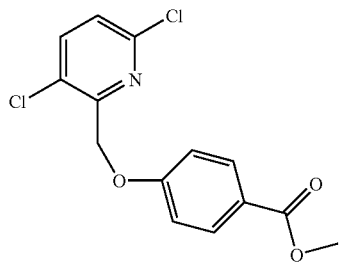

Step A. (3,6-Dichloropyridin-2-yl)methanol

BOP (1.27 g, 2.9 mmol) was added to a THF (10 mL) solution containing 3,6-dichloropyridine-2-carboxylic acid (0.5 g, 2.6 mmol) and DIEA (0.55 mL, 3.2 mmol). After 5 minutes sodium borohydride (103 mg, 2.7 mmol) was added and the solution stirred at room temperature for 20 minutes. The solution was partitioned between ethyl ether and aqueous 1N HCl. The organic phase was washed with water, brine and dried over MgSO$_4$. The solution was filtered, concentrated and the residue purified by silica gel chromatography using a hexanes/ethyl acetate gradient to give the title compound. LCMS2 1.32 min. (M+H)=178

Step B. Methyl 4-[(3,6-dichloropyridin-2-yl)methoxy]benzoate

The title compound was prepared from the intermediate from Step A and methyl 4-hydroxybenzoate using the Mitsunobu conditions described in EXAMPLE 4. $^1$H NMR (500 MHz, CDCl3): δ 8.054 (d, J=8.8 Hz, 2H); 7.74 (d, J=8.4 Hz, 1H); 7.35 (d, J=8.4 Hz, 1H); 7.07 (d, J=8.7 Hz, 2H); 5.31 (s, 2H); 3.93 (s, 3H). LCMS2 2.29 min. (M+H)=312

INTERMEDIATE 6

RACEMIC METHYL 4-[1-(3,6-DICHLOROPYRIDIN-2-YL)ETHOXY]BENZOATE

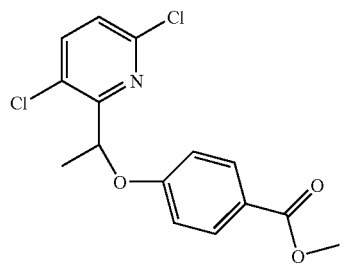

Step A. 1-(3,6-Dichloropyridin-2-yl)ethanol

Methyl magnesium bromide (3.0M Et$_2$O, 0.25 mL, 0.75 mmol) was added dropwise to a THF (2 mL) solution of 3,6-dichloropyridine-2-carbaldehyde (100 mg, 0.57 mmol) cooled to 0° C. After 1 hour the solution was partitioned between ethyl acetate and 1N aqueous HCl. The organic phase was washed with brine, dried over MgSO$_4$, filtered and concentrated. The residue was purified by silica gel chromatography using a hexanes/ethyl acetate gradient to give the title compound. $^1$H NMR (500 MHz, CDCl$_3$): δ 7.67 (d, J=8.4 Hz, 1H); 7.30 (d, J=8.2 Hz, 1H); 5.22-5.14 (m, 1H); 3.83 (d, J=8.7 Hz, 1H) 1.50 (d, J=6.5 Hz, 3H). LCMS1 2.40 min. (M–H2O)=174

Step B. Methyl 4-[1-(3,6-dichloropyridin-2-yl)ethoxy]benzoate

The title compound was prepared from the intermediate from Step A and methyl 4-hydroxybenzoate using the Mitsunobu conditions described in EXAMPLE 4. $^1$H NMR (500 MHz, CDCl$_3$): δ 7.97 (d, J=8.2 Hz, 2H); 7.67 (d, J=8.4 Hz, 1H); 7.26 (d, J=8.3 Hz, 1H); 6.94 (d, J=8.7 Hz, 2H); 5.85 (q, J=6.5 Hz, 1H); 3.90 (s, 3H); 1.78 (d, J=6.5 Hz, 3H). LCMS1 3.68 min. (M-OPhCO2Me)=174

INTERMEDIATE 7

RACEMIC METHYL 4-[1-(2,5-DICHLOROPHENYL)ETHYL]BENZOATE

Step A. Methyl 4-[1-(2,5-dichlorophenyl)-1-hydroxyethyl]benzoate

A solution of iPrMgCl (2.0M THF, 17.8 mL) was added dropwise to a THF solution (16 mL) of 4-iodo methyl benzoate (4.2 g, 16.04 mmol) cooled in an MeOH/ice bath (−15° C.). The solution was stirred at −15° C. until no starting material remained by HPLC (30 min). A THF solution (5 mL) of 1-(2,5-dichloro-phenyl)-ethanone (2.27 g, 13.0 mmol) was then added dropwise. The cooling bath was removed and the solution stirred for approximately 30 minutes. The solution was partitioned between aqueous 1N HCl and ethyl acetate. The organic phase was washed with water, brine and dried over $MgSO_4$. The solution was then filtered, concentrated and the residue purified by silica gel chromatography using a hexanes/ethyl acetate gradient to give the title compound. $^1$H NMR (500 MHz, $CDCl_3$): δ 8.00 (d, J=8.2 Hz, 2H); 7.86 (d, J=2.4 Hz, 1H); 7.38 (d, J=8.3 Hz, 2H); 7.30-7.26 (m, 2H); 3.93 (s, 3H); 1.98 (s, 3H). LCMS1 3.63 min. (M+H)=325

Step B. Methyl 4-[1-(2,5-dichlorophenyl)ethyl]benzoate

To the intermediate from Step A (75 mg, 0.23 mmol) in a screw cap tube was added DCM (2 mL), $Et_3SiH$ (0.4 mL) and TFA (0.4 mL). The closed tube was then heated at 75° C. for 1.5 hours. The solution was cooled and concentrated. To the residue, which is a mixture of the title compound and methyl 4-[1-(2,5-dichlorophenyl)vinyl]benzoate (1/1), was added DCM (4 mL) and $PtO_2$ (15 mg). The solution was stirred under a hydrogen atmosphere (balloon) for 3 hours. The hydrogen was purged and the solution filtered. The residue was purified by silica gel chromatography using a hexanes/ethyl acetate gradient to give the title compound LCMS1 4.19 min. (M+H)=309

INTERMEDIATE 8

RACEMIC METHYL 4-[(6-{[(TRIFLUOROMETHYL)SULFONYL]OXY}-2,3-DIHYDRO-1H-INDEN-1-YL)METHYL]BENZOATE

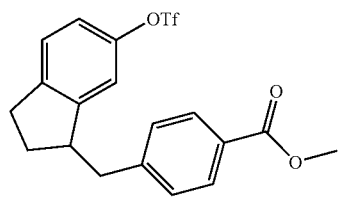

Step A. 6-Methoxyindane-1-carbaldehyde

A dimethylsulfoxide (8 mL) solution containing sodium hydride (60%, 0.14 g, 3.5 mmol) was heated at 75° C. for ca. 45 minutes. The solution was cooled to room temperature and diluted with THF (8 mL). The solution was cooled to 0° C. and trimethylsulfonium iodide (0.7 g, 3.4 mmol) was added in portions. After 15 minutes a THF solution of 6-methoxyindan-1-one (0.5 g, 3.1 mmol) was added. The solution was then stirred at room temperature for 4 days. The solution was diluted with water and ethyl ether. The organic phase was washed with water (3×) and brine. The solution was then dried over $MgSO_4$, filtered and concentrated. The residue was purified by silica gel chromatography using a hexanes/ethyl acetate gradient to give the title compound. $^1$H NMR (500 MHz, $CDCl_3$): δ 9.68 (d, J=2.9 Hz, 1H); 7.29 (s, 1H); 7.21 (d, J=8.0 Hz, 1H); 6.86-6.82 (m, 1H); 3.95-3.93 (m, 1H); 3.82 (s, 3H); 3.03-2.93 (m, 2H); 2.48-2.44 (m, 1H); 2.41-2.37 (m, 1H). LCMS1 2.90 min. (M+H)=177

Step B. Methyl 4-[hydroxy(6-methoxy-2,3-dihydro-1H-inden-1-yl)methyl]benzoate The title compound was prepared from the intermediate from Step A and 4-iodo methyl benzoate using the conditions described in INTERMEDIATE 7 Step A. LCMS1 3.39 min. (M−17)=295

Step C. Methyl 4-[(6-methoxy-2,3-dihydro-1H-inden-1-yl)methyl]benzoate

The title compound was prepared from the intermediate from Step B using the conditions described in INTERMEDIATE 7 Step B. $^1$H NMR (500 MHz, $CDCl_3$): δ 8.00 (d, J=8.2 Hz, 2H); 7.30 (d, J=8.1 Hz, 2H); 7.14 (d, J=8.5 Hz, 1H); 6.75 (dd, J=2.4, 8.2 Hz, 1H); 6.65 (d, J=2.2 Hz, 1H); 3.95 (s, 3H); 3.77 (s, 3H); 3.50-3.42 (m, 1H); 3.18 (dd, J=6.0, 13.6 Hz, 1H); 2.85-2.73 (m, 3H); 2.20-2.13 (m, 1H); 1.82-1.75 (m, 1H). LCMS1 4.03 min. (M−31)=265

Step D. Methyl 4-[(6-hydroxy-2,3-dihydro-1H-inden-1-yl)methyl]benzoate

A solution of $BBr_3$ (1.0M DCM, 0.32 mL) was added dropwise to a DCM (2 mL) solution containing the intermediate from Step C (71 mg, 0.24 mmol). The solution was stirred at room temperature until no starting material remained by HPLC analysis. The reaction was quenched with MeOH (1 mL) and AcOH (1 mL). The solution was then concentrated and the residue partitioned between aqueous 1N HCl and ethyl acetate. The organic phase was washed with water and brine and dried over $MgSO_4$. The filtered solution was concentrated and the residue purified by silica gel chromatography using a hexanes/ethyl acetate gradient to give the title compound. LCMS1 3.51 min (M−31)=251

Step E. Methyl 4-[(6-{[(trifluoromethyl)sulfonyl]oxy}-2,3-dihydro-1H-inden-1-yl)methyl]benzoate Trifluoromethanesulfonic anhydride (0.08 mL, 0.48 mmol) was dropwise to a solution of toluene (2 mL) and aqueous 30% $K_3PO_4$ (2 mL) containing the intermediate from Step D (63 mg, 0.22 mol). The solution was stirred at room temperature until no starting material remained by HPLC analysis. The solution was partitioned between ethyl acetate and water. The organic phase was washed with water and brine. The solution was then dried over $MgSO_4$, filtered and concentrated. The residue was purified by silica gel chromatography using a hexanes/ethyl acetate gradient to give the title compound. $^1$H NMR (500 MHz, $CDCl_3$): δ 8.01 (d, J=8.2 Hz, 2H); 7.27 (d, J=8.1 Hz, 2H); 7.08 (dd, J=2.3, 8.2 Hz, 1H); 6.95 (d, J=2.1 Hz, 1H); 3.95 (s, 3H); 3.56-3.50 (m, 1H); 3.15

(dd, J=6.2, 13.5 Hz, 1H); 2.92-2.80 (m, 3H); 2.28-2.20 (m, 1H); 1.90-1.83 (m, 1H). LCMS2 2.71 min. (M+H)=415

INTERMEDIATE 9

RACEMIC METHYL 4-[(7-METHOXY-1,2,3,4-TETRAHYDRONAPHTHALEN-1-YL)METHYL]BENZOATE

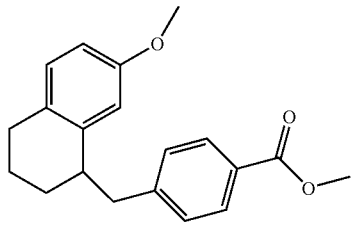

Step A. 7-Methoxy-1-methylene-1,2,3,4-tetrahydronaphthalene n-Butyl lithium (1.6M, 6.2 mL, 9.92 mmol) was added dropwise to a THF (20 mL) solution containing methyltriphenylphosphonium bromide (3.65 g, 10.22 mmol) cooled in an ice bath. The solution was stirred at room temperature for 3 hours. A THF (5 mL) solution of 7-methoxy-3,4-dihydronaphthalen-1(2H)-one (1 g, 5.68 mmol) was added dropwise. The solution was then stirred at 60° C. overnight. The solution was partitioned between ethyl ether and water. The organic phase was washed with water (3×) and brine and dried over MgSO$_4$. The filtered solution was concentrated and the residue purified by silica gel chromatography using a hexanes/ethyl acetate gradient to give the title compound. $^1$H NMR (500 MHz, CDCl$_3$): δ 7.25 (d, J=2.6 Hz, 1H); 7.10 (d, J=8.3 Hz, 1H); 6.86 (dd, J=2.6, 8.4 Hz, 1H); 5.55 (s, 1H); 5.05 (s, 1H); 3.88 (s, 3H); 2.86 (t, J=6.3 Hz, 2H); 2.61 (t, J=6.2 Hz, 2H); 1.96-1.92 (m, 2H). LCMS1 3.79 min. (M+1)=175

Step B. Methyl 4-[(E,Z)-(7-methoxy-3,4-dihydronaphthalen-1(2H)-ylidene)methyl]benzoate A DMF (2 mL) solution containing the intermediate from Step A (100 mg, 0.57 mmol), 4-iodo methyl benzoate (224 mg, 0.855 mmol), NaHCO$_3$ (189 mg, 2.26 mmol), n-Bu$_4$NCl (169 mg, 0.57 mmol) and Pd(OAc)$_2$ (10 mg, 0.044 mmol) was heated at 80° C. overnight under an argon atmosphere. The solution was partitioned between ethyl acetate and water. The organic phase was washed with water, brine and dried over MgSO$_4$. The filtered solution was concentrated and the residue purified by silica gel chromatography using a hexanes/ethyl acetate gradient. The isolated material contained a mixture of olefinic products. LCMS1 4.04 min. (M+1)=309

Step C. Methyl 4-[(7-methoxy-1,2,3,4-tetrahydronaphthalen-1-yl)methyl]benzoate An ethyl acetate solution (4 mL) containing the intermediate from Step B (25 mg, 0.081 mmol) and 10% Pd/C (5 mg) was stirred under a hydrogen atmosphere (balloon) until no starting material remained by HPLC analysis. LCMS2 2.64 min. (M+1)=311

INTERMEDIATE 10

RACEMIC METHYL 4-[2-(2-BROMO-5-METHOXYPHENYL)-1-METHYLETHYL]BENZOATE

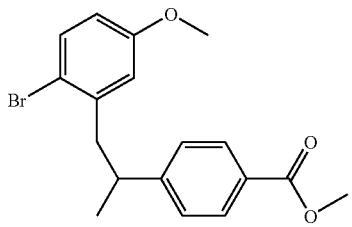

Step A. 4-[2-(2-Bromo-5-methoxyphenyl)-1-methylethyl]benzoic acid

Butyl lithium (1.6M hexanes, 35 mL, 56 mmol) was added dropwise to a THF (50 mL)/HMPA (10 mL) solution of diisopropylamine (7.9 mL, 56 mmol) cooled to −5° C. After stirring 10 minutes a THF solution (17 mL) of 4-ethylbenzoic acid (3.36 g, 22.4 mmol) was added dropwise. The red solution was kept at 5° C. overnight. A THF solution (17 mL) of 1-bromo-2-(bromomethyl)-4-methoxybenzene (60.27 g, 22.4 mmol) was added dropwise. The reaction solution was then allowed to warm to room temperature. The solution was then partitioned between ethyl acetate and aqueous 1N HCl. The organic phase was washed with water, brine and dried over MgSO$_4$. The filtered solution was concentrated and the residue purified by silica gel chromatography using hexanes/ethyl acetate (with 1% AcOH) gradient to give the title compound. LCMS1 3.72 min. (M−17)=331

Step B. Methyl 4-[2-(2-bromo-5-methoxyphenyl)-1-methylethyl]benzoate (Trimethylsilyl)diazomethane (2.0M hexanes, 4.8 mL) was added dropwise to a benzene/MeOH solution (7/3, 50 mL) containing the intermediate from Step A (2.8 g, 8.0 mmol). After 20 minutes AcOH was added dropwise to quench the excess reagent. The solution was concentrated and the residue purified by silica gel chromatography using a hexanes/ethyl acetate gradient to give the title compound. $^1$H NMR (500 MHz, CDCl$_3$): δ 7.98 (d, J=8.2 Hz, 2H); 7.43 (d, J=8.2 Hz, 1H); 7.29 (d, J=8.2 Hz, 2H); 6.63 (dd, J=3.0, 8.7 Hz, 1H); 6.50 (d, J=3.0 Hz, 1H); 3.93 (s, 3H); 3.68 (s, 3H);

3.26-3.19 (m, 1H); 2.96 (d, J=7.0 Hz, 2H); 1.34 (d, J=6.9 Hz, 3H). LCMS1 4.14 min. (M-31)=331

INTERMEDIATE 11

4-[2-(2-BROMO-5-METHOXYPHENYL)ETHYL]BENZOIC ACID

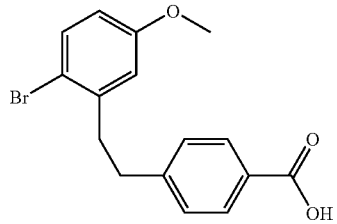

The title compound was prepared from 4-methylbenzoic acid and 1-bromo-2-(bromomethyl)-4-methoxybenzene using the procedure described for the preparation of INTERMEDIATE 10. $^1$H NMR (400 MHz, CD$_3$OD): δ 7.90 (d, J=8.3 Hz, 2H); 7.40 (d, J=8.7 Hz, 1H); 7.27 (d, J=8.2 Hz, 2H); 6.72-6.66 (m, 2H); 3.68 (s, 3H); 3.01-2.91 (m, 4H). LCMS1 3.68 min. (M-OH)=317

INTERMEDIATE 12

4-{2-[5-CHLORO-2-(TRIFLUOROMETHYL)PHENYL]ETHYL}BENZOIC ACID

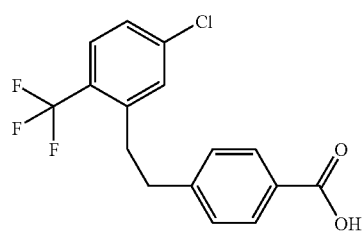

The title compound was made from 4-methylbenzoic acid and 2-(bromomethyl)-4-chloro-1-(trifluoromethyl)benzene using the procedure described for the preparation of INTERMEDIATE 10. $^1$H NMR (500 MHz, CDCl$_3$): δ 8.10 (d, J=8.1 Hz, 2H); 7.62 (d, J=8.2 Hz, 1H); 7.32 (m, 4H); 3.11-3.07 (m, 2H); 3.05-2.99 (m, 2H).

INTERMEDIATE 13

RACEMIC METHYL 4-[2-(3-CHLOROPHENYL)-2-(1-METHYL-1H-PYRAZOL-5-YL)ETHYL]BENZOATE

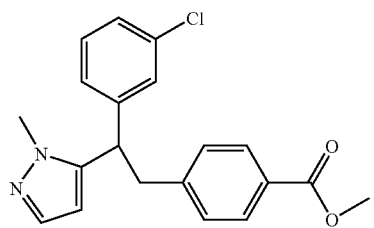

Step A. Methyl 4-[2-(3-chlorophenyl)-3-oxobutyl]benzoate

Sodium t-butoxide (0.60 g, 6.34 mmol) was added all at once to a THF solution (10 mL) of 1-(3-chloro-phenyl)-propan-2-one (1.08 g, 6.40 mmol) stirred at −78° C. After 3 minutes 4-bromomethyl-benzoic acid methyl ester (1.54 g, 6.72 mmol) was added all at once and the reaction solution was allowed to warm to room temperature. After stirring for 1 hour the reaction solution was partitioned between aqueous 1N HCl and ethyl acetate. The organic phase was washed with brine and dried over MgSO$_4$. The solution was filtered, concentrated and the residue purified by silica gel chromatography using a hexanes/ethyl acetate gradient to give the title compound. $^1$H NMR (500 MHz, CDCl$_3$): δ 7.91 (d, J=8.2 Hz, 2H); 7.29-7.25 (m, 2H); 7.20 (s, 1H); 7.13 (d, J=8.2 Hz, 2H); 7.07-7.03 (m, 1H); 3.91 (broad s, 4H); 3.47 (dd, J=7.2, 13.8 Hz, 1H); 2.96 (dd, J=7.6, 13.8 Hz, 1H); 2.07 (s, 3H). LCMS1 3.66 min. (M+H)=317.

Steps B. Methyl 4-[(4E)-2-(3-chlorophenyl)-5-(dimethylamino)-3-oxopent-4-en-1-yl]benzoate To a screw cap tube was added the intermediate from Step A (50 mg, 0.16 mmol), MeOH (2 mL), N,N-dimethylformamide dimethyl acetal (0.4 mL, excess) and acetic acid (10 drops). The solution was heated at 100° C. until no starting material remained by HPLC analysis (ca. 1 hour). The solution was then cooled and concentrated. The residue was partitioned between ethyl acetate and water. The organic phase was washed with brine, dried over MgSO$_4$, filtered and concentrated to give the title compound. $^1$H NMR (500 MHz, CDCl$_3$): δ 7.88 (d, J=8.2 Hz, 2H); 7.53 (d, J=12.4 Hz, 1H); 7.29 (d, J=1.7 Hz, 1H); 7.20-7.14 (m, 5H); 4.90 (d, J=12.4 Hz, 1H); 3.88 (s, 3H); 3.80 (t, J=7.4 Hz, 1H); 3.54 (dd, J=8.0, 13.7 Hz, 1H); 3.02 (broad s, 3H); 2.99-2.81 (m, 1H); 2.71 (broad s, 3H). LCMS1 3.45 min. (M+H)=372.

Step C Methyl 4-[2-(3-chlorophenyl)-2-(1-methyl-1H-pyrazol-5-yl)ethyl]benzoate To a screw cap tube was added the intermediate from Step B (50 mg, 0.13 mmol), MeOH (2 mL), methyl hydrazine (0.3 mL, excess) and acetic acid (10 drops). The solution was heated at 100° C. until no starting material remained by HPLC analysis (ca. 1 hour). The solution was then cooled and concentrated. The residue was partitioned between ethyl acetate and water. The organic phase was washed with brine, dried over MgSO$_4$, filtered and concentrated. The residue was purified by silica gel chromatography using a hexanes/ethyl acetate gradient to give the title compound. LCMS1 3.55 min. (M+H)=355

INTERMEDIATE 14

RACEMIC METHYL 4-{3-(2-FLUOROPHENYL)-3-OXO-2-[4'-(TRIFLUOROMETHOXY)BIPHENYL-3-YL]PROPYL}BENZOATE

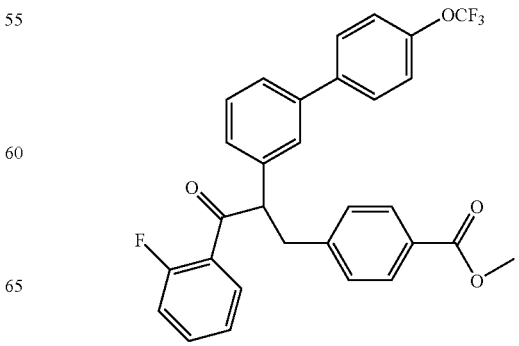

Step A. 3'-Chlorobiphenyl-4-yl trifluoromethyl ether

A solution of DME (40 mL) and 2M $K_2CO_3$ (40 mL) containing 1-bromo-3-chlorobenzene (2.53 g, 13.21 mol), 4-(trifluoromethoxy)phenyl boronic acid (4 g, 19.4 mmol) and $Pd(PPh_3)_4$ (0.76 g, 0.66 mmol) was refluxed under an argon atmosphere until no starting material remained by HPLC analysis. The solution was concentrated (to remove excess DME) and partitioned between water and ethyl acetate. The organic phase was washed with 1N NaOH, water (2×) and brine. The solution was then dried over $MgSO_4$, filtered and concentrated. The residue was purified by silica gel chromatography using a hexanes/ethyl acetate gradient to give the title compound. LCMS1 4.23 min.

Step B. 1-(2-Fluorophenyl)-2-[4'-(Trifluoromethoxy)biphenyl-3-yl]ethanone

A 1,4-dioxane solution (50 mL) containing the intermediate from Step A (2.4 g, 8.80 mmol), 2-fluoro acetophenone (3.04 g, 22.0 mmol), $K_3PO_4$ (4.9 g, 23 mmol), $Pd(OAc)_2$ (79 mg, 0.35 mmol), and dicyclohexyl-(2'-methyl-biphenyl-2-yl)-phosphane (282 mg, 0.77 mmol) was heated for 2 hours at 85° C. under an argon atmosphere. The solution was partitioned between ethyl acetate and water. The organic phase was washed with aqueous 1N HCl, brine and dried over $MgSO_4$. The solution was then filtered, concentrated and the residue purified by silica gel chromatography using a hexanes/ethyl acetate gradient to give the title compound. H NMR (500 MHz, $CDCl_3$): δ 7.92-7.88 (m, 1H); 7.63-7.53 (m, 3H); 7.50-7.41 (m, 3H); 7.32-7.27 (m, 4H); 7.21-7.17 (m, 1H); 4.39 (d, J=2.5 Hz, 2H). LCMS1 4.19 min. (M+H)=375

Step C. Methyl 4-{3-(2-fluorophenyl)-3-oxo-2-[4'-(trifluoromethoxy)biphenyl-3-yl]propyl}benzoate Sodium t-butoxide (67 mg, 0.70 mmol) was added all at once to a THF solution (4 mL) containing the intermediate from Step B (250 mg, 0.668 mmol) stirred at −78° C. After 2 minutes 4-bromomethyl-benzoic acid methyl ester (161 mg, 0.70 mmol) was added all at once. The reaction solution was allowed to warm to room temperature. After stirring for 1 hour the reaction solution was partitioned between aqueous 1N HCl and ethyl acetate. The organic phase was washed with brine and dried over $MgSO_4$. The solution was filtered, concentrated and the residue purified by silica gel chromatography using a hexanes/ethyl acetate gradient to give the title compound. $^1$H NMR (500 MHz, $CDCl_3$): δ 7.92-7.90 (m, 2H); 7.79-7.75 (m, 1H); 7.51-7.49 (m, 2H); 7.47-7.32 (m, 4H); 7.30-7.27 (m, 2H); 7.24-7.19 (m, 3H); 7.17-7.15 (m, 1H); 7.05 (dd, J=8.3, 11.3 Hz, 1H); 4.88 (t, J=7.4 Hz, 1H); 3.91 (s, 3H); 3.68 (dd, J=7.1, 13.7 Hz, 1H); 3.17 (dd, J=7.6, 13.7 Hz, 1H). LCMS1 4.40 min. (M+H)⁻ 523

INTERMEDIATE 15

RACEMIC ETHYL 4-[1-(5-BROMO-2-HYDROXYPHENYL)ETHYL]BENZOATE

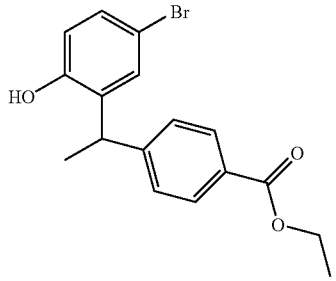

The title compound was prepared from 1-(5-bromo-2-hydroxyphenyl)ethanone and 4-iodo ethyl benzoate as described for the preparation of INTERMEDIATE 7. $^1$H NMR (400 MHz, $CD_3OD$): δ 7.89 (d, J=8.4 Hz, 2H); 7.31 (d, J=8.3 Hz, 2H); 7.13-7.09 (m, 2H); 6.65 (d, J=8.5 Hz, 1H); 4.52 (q, J=7.2 Hz, 1H); 4.31 (q, J=7.1 Hz, 2H); 1.54 (d, J=7.3 Hz, 3H); 1.34 (t, J=7.1 Hz, 3H). LCMS1 3.82 min. (M+1)= 349.

INTERMEDIATE 16

METHYL 4-(2,5-DICHLOROBENZYL)BENZOATE

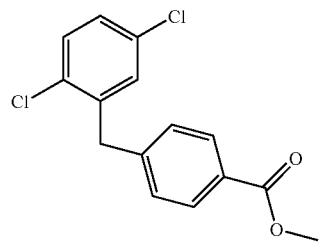

The title compound was prepared from 2,5-dichlorobenzaldehyde and 4-iodo methyl benzoate as described for the preparation of INTERMEDIATE 7. $^1$H NMR (500 MHz, $CDCl_3$): δ 8.01 (d, J=8.3 Hz, 2H); 7.34 (d, J=8.5 Hz, 1H); 7.29 (d, J=5.3 Hz, 2H); 7.21-7.17 (m, 1H); 7.15 (d, J=2.4 Hz, 1H); 4.14 (s, 2H); 3.93 (s, 3H). LCMS1 4.14 min. (M+1)=295.

INTERMEDIATE 17

RACEMIC ETHYL 4-[1-(4'-(TRIFLUOROMETHOXY)-4-{[(TRIFLUOROMETHYL)SULFONYL]OXY}BIPHENYL-3-YL)ETHYL]BENZOATE

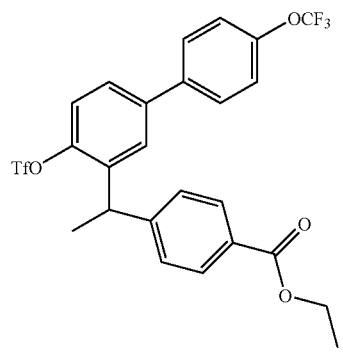

Step A. Ethyl 4-{1-[4-hydroxy-4'-(trifluoromethoxy)biphenyl-3-yl]ethyl}benzoate

The title compound was made from INTERMEDIATE 15 using the Suzuki conditions described in EXAMPLE 1 Step A. LCMS1 4.22 min. (M+H)=431.

Step B. Ethyl 4-[1-(4'-(trifluoromethoxy)-4-{[trifluoromethyl)sulfonyl]oxy}biphenyl-3-yl)ethyl]benzoate The title compound was made from the intermediate from Step A using trifluoromethanesulfonic anhydride as described in the procedure for INTERMEDIATE 8 Step E. $^1$H NMR (500 MHz, CDCl$_3$): δ 8.02 (d, J=8.3 Hz, 2H); 7.53-7.47 (m, 3H); 7.44 (d, J=2.3 Hz, 1H); 7.38-7.30 (m, 5H); 4.65 (q, J=7.1 Hz, 1H); 4.41-4.37 (m, 2H); 1.74 (d, J=7.1 Hz, 3H); 1.40 (dd, J=7.0 Hz, 3H). LCMS1 4.67 min. (M+H)=563.

INTERMEDIATE 18

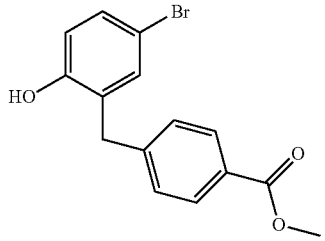

The title compound was prepared from 5-Bromo-2-hydroxy-benzaldehyde using the procedure described for the preparation of INTERMEDIATE 7. $^1$H NMR (400 MHz, DMSO): δ 9.77 (s, 1H); 7.83 (d, J=8.2 Hz, 3H); 7.32 (d, J=8.2 Hz, 3H); 7.20-7.14 (m, 3H); 6.74 (dd, J=2.5, 8.6 Hz, 2H); 3.88 (s, 2H); 3.78 (s, 3H). LCMS1 3.57 min. (M+H)=321.

INTERMEDIATE 19

METHYL 4-F{[4-BROMO-4'-(TRIFLUOROMETHOXY)BIPHENYL-3-YL]OXY}BENZOATE

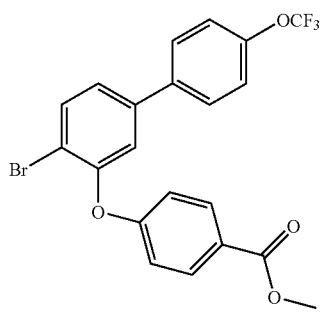

Step A. Methyl 4-(5-chloro-2-nitrophenoxy)benzoate

A DMF (4 mL) solution containing Na$_2$CO$_3$ (60 mg, 0.57 mmol), 4-chloro-2-fluoro-1-nitrobenzene (100 mg, 0.57 mmol) and methyl 4-hydroxybenzoate (87 mg, 0.57 mmol) was stirred at room temperature for 8 hours. HPLC analysis indicated ca. 85% product. The reaction solution was stirred for an additional 2 hours at 40° C. The solution was then diluted with ethyl acetate and washed with 1N NaOH. The organic phase was washed with water (3×), brine and dried over Na$_2$SO$_4$. The solution was filtered, concentrated and the residue purified by silica gel chromatography using a hexanes/ethyl acetate gradient to give the title compound. $^1$H NMR (500 MHz, CDCl$_3$): δ 8.11 (d, J=8.1 Hz, 2H); 8.01 (d, J=8.2 Hz, 1H); 7.31-7.27 (m, 1H); 7.11-7.07 (m, 3H); 3.95 (s, 3H). LCMS1 3.66 min. (M+H)=308.

Step B. Methyl 4-{[4-nitro-4'-(trifluoromethoxy)biphenyl-3-yl]oxy}benzoate

A DMF (4 mL) solution containing the intermediate from Step A (50 mg, 0.163 mmol), K$_3$PO$_4$ (69 mg, 0.326 mmol), tetrabutylammonium bromide (11 mg, 0.033 mmol), Pd(OAc)$_2$ (4 mg, 0.018 mmol) and (trifluoromethoxy)phenyl boronic acid (67 mg, 0.326 mmol) was stirred at 100° C. under an argon atmosphere for 1 hour. The reaction was cooled and diluted with ethyl acetate. The solution was washed with 1N NaOH, water (3×) and brine. The solution was then dried over Na$_2$SO$_4$, filtered and concentrated. The residue was purified by silica gel chromatography using a hexanes/ethyl acetate gradient to give the title compound. LCMS1 4.14 min. (M+H)=434.

Step C. Methyl 4-{[4-amino-4'-(trifluoromethoxy)biphenyl-3-yl]-4-oxy}benzoate

An ethyl acetate (20 mL) solution containing the intermediate from Step B (861 mg, 1.99 mmol) and 15 wt % Pd/C (129 mg) was stirred under a hydrogen atmosphere (balloon) for 1 hour. The solution was filtered and concentrated. The residue was used without further purification. LCMS1 3.95 min. (M+H)=404

Step D. methyl 4-{[4-bromo-4'-(trifluoromethoxy)biphenyl-3-yl]oxy}benzoate

The title compound was made from the intermediate from Step C using the procedure described in EXAMPLE 1 Step B. $^1$H NMR (500 MHz, CDCl$_3$): δ 8.07-8.05 (m, 2H); 7.75 (d, J=8.3 Hz, 1H); 7.57-7.54 (m, 2H); 7.33-7.29 (m, 4H); 7.02-6.99 (m, 2H); 3.93 (s, 3H). LCMS1 4.44 min. (M+H)=467

INTERMEDIATE 20

METHYL 4-[(2,5-DICHLOROPHENYL)THIO]BENZOATE

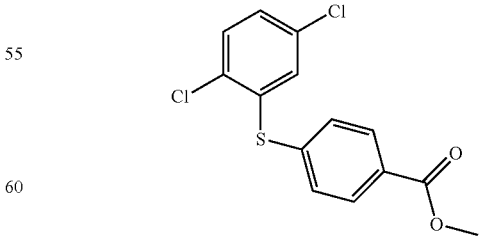

A toluene solution (30 mL) containing 2,6-dichloro thiophenol (2.53 g, 14.13 mmol), 4-iodo methylbenzoate (4.1 g, 15.65 mmol), CuI (300 mg, 1.57 mmol), K$_3$PO$_4$ (5.0 g, 23.6 mmol) and 2,9-dimethyl-[1,10]phenanthroline (328 mg, 1.58 mmol) was heated at reflux for 3 hours. The solution was then partitioned between water and ethyl acetate. The organic phase was washed with aqueous 1N NaOH, NH₄OH, 1N HCl and brine. The solution was then dried over MgSO₄, filtered and concentrated. The residue was purified by silica gel chromatography using a hexanes/ethyl acetate gradient to give the title compound. ¹H NMR (400 MHz, CDCl₃): δ 8.01 (d, J=8.5 Hz, 2H); 7.37 (dd, J=3.0, 8.4 Hz, 3H); 7.21-7.17 (m, 2H); 3.92 (s, 3H). LCMS1 4.21 min. (M+H)=313

EXAMPLE 6

N-(4-{2-[4-(1H-PYRAZOL-1-YL)-4'-(TRIFLUO-ROMETHOXY)BIPHENYL-3-YL]ETHYL}BENZOYL)-β-ALANINE

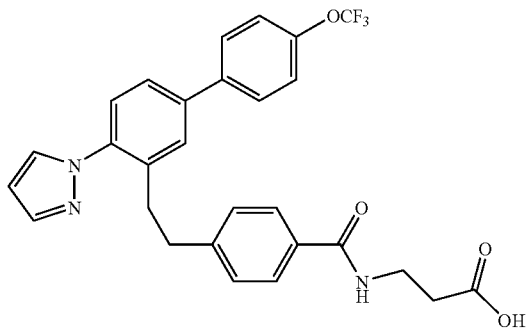

A 1-methyl-2-pyrrolidine (1 mL) solution containing the intermediate from EXAMPLE 1 Step H (40 mg, 0.07 mmol), pyrazole (10 mg, 0.14 mmol), K₂CO₃ (19 mg, 0.14 mmol) and CuI (2 mg, 0.007 mmol) was heated at 200° C. in a microwave (250 watts). After 2 hours the solution was cooled and concentrated. The tert butyl group was cleaved with TFA as described in EXAMPLE 1 and the crude material was purified by RP-HPLC to give the title compound. LCMS1 3.69 min (M+H)=524

EXAMPLE 7

N-(4-{2-[4-METHYL-4'-(TRIFLUO-ROMETHOXY)BIPHENYL-3-YL]ETHYL}BENZOYL)-β-ALANINE

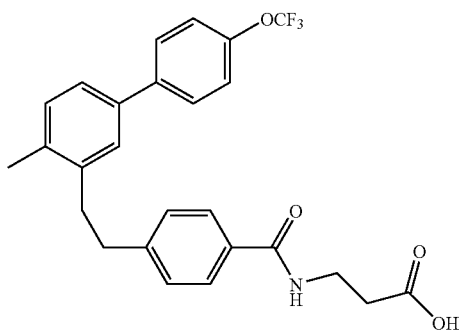

Tetramethylstannane (41 μl, 0.295 mmol) was added to the intermediate from Example 1 Step H (35 mg, 0.059 mmol),
Pd(PPh₃)₄ (5 mg, 0.04 mmol) in 3 mL DMF. The solution was then heated at 120° C. overnight under an argon atmosphere. The solution was cooled and partitioned between ethyl acetate and water. The organic phase was washed with water (3×) and brine. The solution was then dried over Na₂SO₄, filtered and concentrated. The residue was purified by PTLC using 6/4 hexanes/ethyl acetate mobile phase to give tert-butyl N-(4-{2-[4-methyl-4-(trifluoromethoxy)biphenyl-3-yl]ethyl}benzoyl)-β-alaninate. The tert butyl group was removed with TFA as described in EXAMPLE 1 Step I to give the title compound. ¹H NMR (500 MHz, CDCl₃): δ 7.73 (d, J=7.9 Hz, 2H); 7.54 (d, J=8.5 Hz, 2H); 7.36-7.33 (m, 1H); 7.31-7.23 (m, 6H); 6.81-6.76 (m, 1H); 3.80-3.75 (m, 2H); 2.99 (s, 4H); 2.77 (t, J=5.7 Hz, 2H); 2.35 (s, 3H). LCMS1 3.94 min (M+H)=472

EXAMPLE 8

4-{2-[3-CHLORO-4''-(TRIFLUOROMETHOXY)-1,1':4',1''-TERPHENYL-2'-YL]ETHYL}-N-1H-TET-RAZOL-5-YLBENZAMIDE

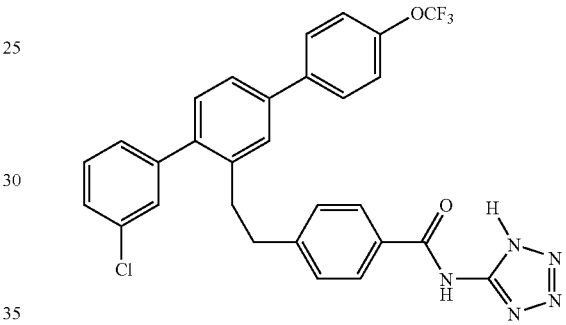

A DMF solution (1 mL) containing 4-{2-[3-chloro-4''-(trifluoromethoxy)-1,1':4',1''-terphenyl-2'-yl]ethyl}benzoic acid (12 mg, 0.024 mmol), prepared using the procedures described in EXAMPLE 1, DIEA (21 μg, 0.12 mmol), 1H-tetrazol-5-amine (3 mg, 0.036 mmol), and BOP (21 mg, 0.048 mmol) was heated at 50° C. for 30 minutes. The solution was then purified directly by RP-HPLC to give the title compound. LCMS1 4.36 min (N+H)=564

EXAMPLE 9

N-(4-{2-[4-(PHENYLTHIO)-4'-(TRIFLUO-ROMETHOXY)BIPHENYL-3-YL]ETHYL}BENZOYL)-β-ALANINE

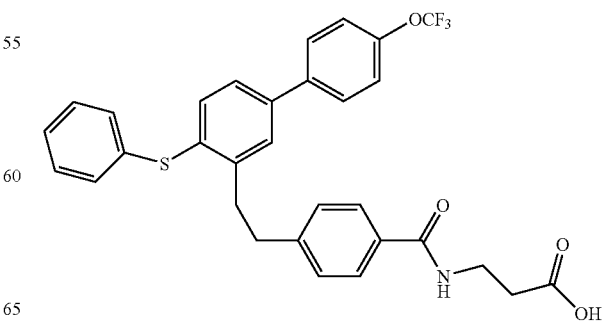

A DMF (1 mL) solution containing the intermediate from EXAMPLE 1 Step H (30 mg, 0.05 μmol), Cu₂O (4 mg, 0.025 mmol), KOH (3 mg, 0.05 mmol) and thiophenol (5.2 μl) was heated to 120° C. overnight. The crude material was partitioned between ethyl acetate and water. The organic phase was washed with water, brine, and dried over Na₂SO₄. The solution was filtered, concentrated and the residue purified by PTLC to give tert-butyl N-(4-{2-[4-(phenylthio)-4'-(trifluoromethoxy)biphenyl-3-yl]ethyl}benzoyl)-β-alaninate. The tert butyl group was removed with TFA as described in EXAMPLE 1 Step I to give the title compound. ¹H NMR (500 MHz, CDCl₃): selected data 3.62 (t, J=6.4 Hz, 2H); 3.16 (t, J=7.6 Hz, 2H); 2.97 (t, J=6.6 Hz, 2H); 2.64 (t, J=7.4 Hz, 2H). LCMS1 4.27 min (M+H)=566.

EXAMPLE 10

N-(4-{2-[4-(BUTOXYCARBONYL)-4'-(TRIFLUOROMETHOXY)BIPHENYL-3-YL]ETHYL}BENZOYL)-β-ALANINE

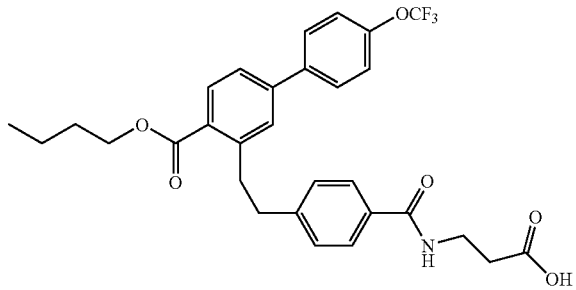

A n-butanol (3 mL) solution containing the intermediate from EXAMPLE 1 Step H (50 mg, 0.085 mmol), DIEA (44 μl, 0.255 mmol) and PdCl₂(PPh₃)₂ (12 mg, 0.017 mmol) was heated at 115° C. under a carbon monoxide atmosphere overnight. The solution was concentrated and the residue purified by PTLC using a 1/1 hexanes/ethyl acetate mobile phase to give tert butyl N-(4-{2-[4-(butoxycarbonyl)-4'-(trifluoromethoxy)biphenyl-3-yl]ethyl}benzoyl)-β-alaninate. The tert-butyl group was cleaved with TFA as described in EXAMPLE 1 Step I and the residue purified by RP-HPLC to give the title compound. LCMS1 4.68 min (M+H)=558

EXAMPLE 11

N-(4-{2-[4-CYANO-4'-(TRIFLUOROMETHOXY)BIPHENYL-3-YL]ETHYL}BENZOYL)-β-ALANINE

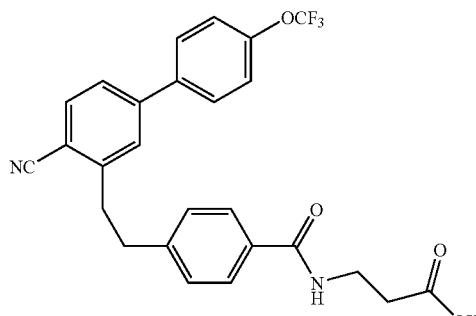

A DMF (2 mL) solution containing the intermediate from EXAMPLE 1 Step H (10 mg, 0.02 mmol), Zn(CN)₂ (7 mg, 0.06 mmol), Pd₂dba₃ (4 mg, 0.004 mmol) and 1,1'-bis(diphenylphosphino)-ferrocine (6 mg, 0.01 mmol) was heated at 120° C. for 1 hour. The solution was cooled and partitioned between ethyl acetate and water. The organic phase was washed with water (3×) and brine. The solution was then dried over MgSO₄, filtered and concentrated. The residue was purified by PTLC using a hexanes/ethyl acetate mobile phase. The tert butyl group was cleaved with TFA as described in EXAMPLE 1 Step I. 1H NMR (500 MHz, CD3OD): δ7.75 (t, J=8.8 Hz, 3H); 7.68-7.66 (m, 2H); 7.63 (dd, J=1.7, 8.0 Hz, 1H); 7.55 (d, J=1.5 Hz, 1H); 7.37 (d, J=8.1 Hz, 2H); 7.30 (d, J=8.1 Hz, 2H); 3.62 (t, J=6.9 Hz, 2H); 3.24 (t, J=7.7 Hz, 2H); 3.10 (t, J=7.7 Hz, 2H); 2.66-2.62 (m, 2H). LCMS1 3.70 min. (M+H)=483.

EXAMPLE 12

N-{4-[({4-[4-(TRIFLUOROMETHOXY)PHENYL]-2-NAPHTHYL}OXY)METHYL]BENZOYL}-β-ALANINE

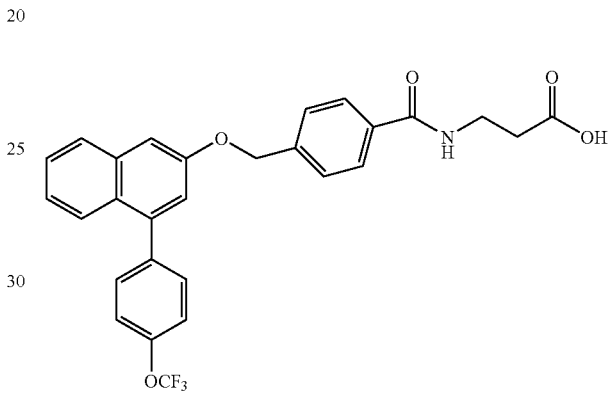

The title compound was prepared from 3-hydroxy-1-naphthyl trifluoromethanesulfonate (from EXAMPLE 2, Step A) as described in EXAMPLE 2. ¹H NMR (500 MHz, CD₃OD): δ 8.54 (s, 1H); 7.86 (d, J=8.3 Hz, 2H); 7.83 (d, J=8.1 Hz, 1H); 7.68 (d, J=8.3 Hz, 1H); 7.62 (d, J=8.2 Hz, 2H); 7.56 (d, J=8.2 Hz, 2H); 7.47-7.45 (m, 1H); 7.43 (d, J=7.9 Hz, 2H); 7.38 (d, J=2.4 Hz, 1H); 7.32-7.30 (m, 1H); 7.18 (d, J=2.5 Hz, 1H); 5.31 (s, 2H); 3.68-3.64 (m, 2H); 2.66 (t, J=6.9 Hz, 2H). LCMS1 3.95 min. (M+H)=510

EXAMPLE 13

RACEMIC N-{4-[1-({3-[4-(TRIFLUOROMETHOXY)PHENYL]-1-NAPHTHYL}OXY)ETHYL]BENZOYL}-β-ALANINE

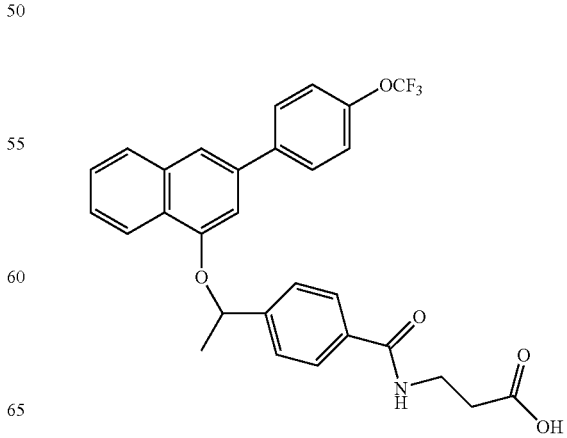

The title compound was prepared from 4-hydroxy-2-naphthyl trifluoromethanesulfonate and racemic methyl 4-(1-bromoethyl)benzoate using the chemistry described in EXAMPLE 2. ¹H NMR (500 MHz, CDCl3): δ 8.48-8.43 (m, 1H); 7.89-7.84 (m, 1H); 7.78 (d, J=8.2 Hz, 2H); 7.71-7.67 (m, 1H); 7.59-7.47 (m, 6H); 7.30 (d, J=10.1 Hz, 2H); 6.859-6.82 (m, 2H); 5.67 (q, J=6.3 Hz, 1H); 3.74 (q, J=5.8 Hz, 2H); 2.72 (q, J=5.7 Hz, 2H); 1.83 (d, J=6.4 Hz, 3H). LCMS1 4.01 min. (M+H)=524

EXAMPLE 14

N-{4-[({3-[4-(TRIFLUOROMETHOXY)PHENYL]-2-NAPHTHYL}OXY)METHYL]BENZOYL}-β-ALANINE

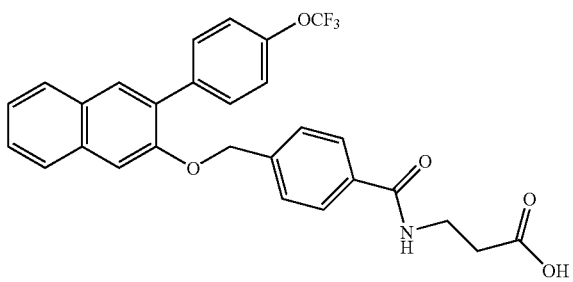

The title compound was prepared from naphthalene-2,3-diol using the procedure described in EXAMPLE 2. ¹H NMR (500 MHz, CD₃OD): δ 7.85-7.81 (m, 2H); 7.81-7.77 (m, 3H); 7.72 (d, J=8.8 Hz, 2H); 7.49-7.43 (m, 4H); 7.39-7.32 (m, 3H); 5.31 (s, 2H); 3.62 (t, J=6.9 Hz, 2H); 2.63 (t, J=6.8 Hz, 2H). LCMS1 3.95 min. (M+H)=510

EXAMPLE 15

N-{4-[({3-[4-(TRIFLUOROMETHOXY)PHENYL]ISOQUINOLIN-1-YL}OXY)METHYL]BENZOYL}-β-ALANINE

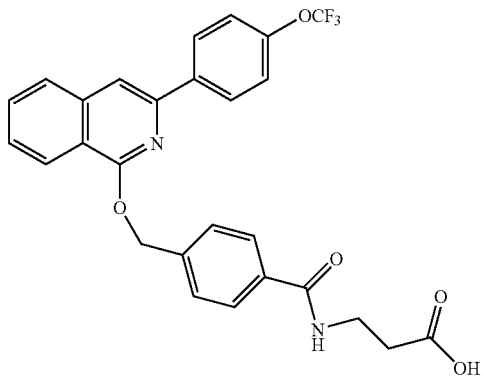

The title compound was prepared from INTERMEDIATE 3 using the chemistry described in EXAMPLE 3 Step B (Suzuki coupling) and EXAMPLE 1. ¹H NMR (500 MHz, CD₃OD): δ 8.31 (d, J=8.1 Hz, 1H); 8.26-8.24 (m, 2H); 7.91 (d, J=8.2 Hz, 1H); 7.88-7.84 (m, 3H); 7.76-7.72 (m, 1H); 7.69 (d, J=8.3 Hz, 2H); 7.61-7.59 (m, 1H); 7.37 (d, J=8.1 Hz, 2H); 5.80 (s, 2H); 3.65 (t, J=6.9 Hz, 2H); 2.66 (t, J=6.9 Hz, 2H). LCMS1 3.98 min. (M+H)=511

EXAMPLE 16

RACEMIC N-{4-[1-({3-[4-(TRIFLUOROMETHOXY)PHENYL]ISOQUINOLIN-1-YL}OXY)ETHYL]BENZOYL}-β-ALANINE

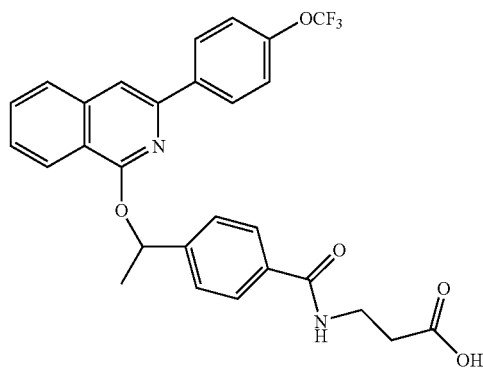

The title compound was prepared from INTERMEDIATE 4 using the chemistry described in EXAMPLE 3 Step B (Suzuki coupling) and EXAMPLE 1. ¹H NMR (500 MHz, CD₃OD): δ 8.39 (d, J=8.2 Hz, 1H); 8.11 (m, 2H); 7.87 (d, J=8.0 Hz, 1H); 7.81-7.77 (m, 3H); 7.76-7.72 (m, 1H); 7.66 (d, J=8.3 Hz, 2H); 7.64-7.58 (m, 1H); 7.33 (d, J=8.1 Hz, 2H); 6.58 (q, J=6.5 Hz, 1H); 3.64-3.60 (m, 2H); 2.62 (t, J=6.9 Hz, 2H); 1.82 (d, J=7.1 Hz, 3H). LCMS1 4.03 min. (M+H)=525

EXAMPLE 17

N-[4-({3,6-BIS [4-(TRIFLUOROMETHOXY)PHENYL]PYRIDIN-2-YL}METHOXY)BENZOYL]-β-ALANINE

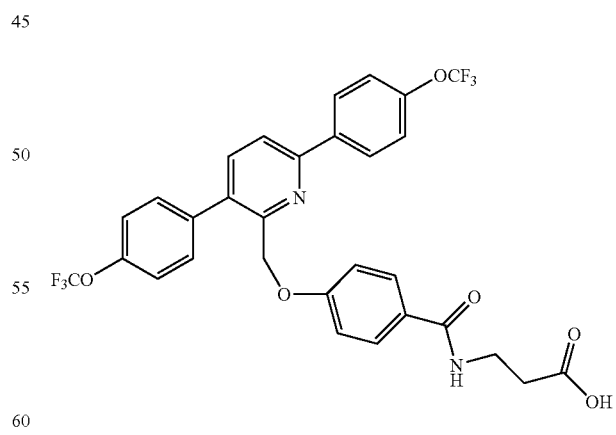

The title compound was made from the INTERMEDIATE 5 using the chemistry described in EXAMPLE 3 Step B (Suzuki coupling) and EXAMPLE 1. ¹H NMR (500 MHz, CDCl₃): δ 11.35 (s, 1H); 8.06 (d, J=8.2 Hz, 1H); 8.02 (d, J=8.7 Hz, 2H); 7.94 (d, J=8.2 Hz, 2H); 7.67 (d, J=8.7 Hz, 2H); 7.52 (d, J=8.6 Hz, 2H); 7.39 (d, J=8.2 Hz, 2H); 7.35 (d, J=8.1 Hz, 2H); 7.19 (t, J=5.7 Hz, 1H); 6.92 (d, J=8.8 Hz, 2H); 5.30 (s, 2H); 3.66 (t, J=5.7 Hz, 2H); 2.66 (t, J=5.9 Hz, 2H). LCMS1 4.01 min. (M+H)=621

EXAMPLE 18

N-[4-({2,5-BIS[4-(TRIFLUOROMETHOXY)PHENYL]PYRIDIN-4-YL}METHOXY)BENZOYL]-β-ALANINE

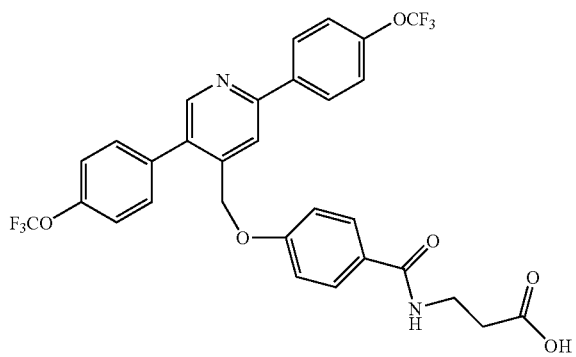

The title compound was prepared from 2,5-dichloroisonicotinic acid using the chemistry described for the preparation of INTERMEDIATE 5 and in EXAMPLE 1 and 3. $^1$H NMR (400 MHz, CD$_3$OD): δ 8.59 (s, 1H); 8.16 (s, 1H); 8.09 (d, J=9.0 Hz, 2H); 7.72 (d, J=8.8 Hz, 2H); 7.57 (d, J=8.7 Hz, 2H); 7.39 (t, J=7.2 Hz, 4H); 6.92 (d, J=8.9 Hz, 2H); 5.16 (s, 2H); 3.56 (t, J=6.9 Hz, 2H); 2.58 (t, J=6.9 Hz, 2H). LCMS1 3.97 min. (M+H)=621

EXAMPLE 19

N-[4-({2,5-BIS[4-(TRIFLUOROMETHOXY)PHENYL]PYRIDIN-3-YL}METHOXY)BENZOYL]-β-ALANINE

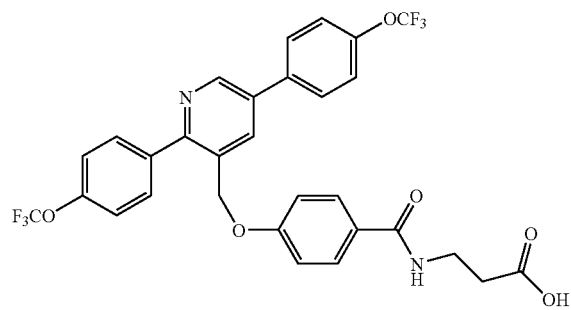

The title compound was prepared from 5-bromo-2-chloronicotinic acid using the chemistry described for the preparation of INTERMEDIATE 5 and in EXAMPLE 1 and 3. $^1$H NMR (400 MHz, CD$_3$OD): δ 8.94 (d, J=2.0 Hz, 1H); 8.51 (d, J=1.9 Hz, 1H); 7.85 (d, J=8.7 Hz, 2H); 7.74 (d, J=8.7 Hz, 4H); 7.41 (t, J=9.3 Hz, 4H); 6.95 (d, J=8.8 Hz, 2H); 5.16 (s, 2H); 3.57 (t, J=6.9 Hz, 2H); 2.5 g (t, J=6.9 Hz, 2H). LCMS1 3.79 min. (M+H)=621

EXAMPLE 20

N-(4-{[4,4''-BIS(TRIFLUOROMETHOXY)-1,1':4',1''-TERPHENYL-2'-YL]METHOXY}BENZOYL)-β-ALANINE

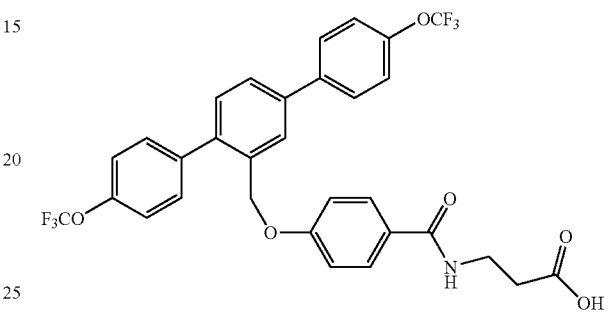

The title compound was prepared from (2,5-dichlorophenyl)methanol and methyl 4-hydroxybenzoate using the chemistry described in EXAMPLE 1, 3 and 4. $^1$H NMR (500 MHz, CD$_3$OD): δ 7.87 (d, J=1.8 Hz, 1H); 7.79-7.71 (m, 5H); 7.54 (d, J=8.8 Hz, 2H); 7.46 (d, J=7.9 Hz, 1H); 7.38 (d, J=8.1 Hz, 2H); 7.32 (d, J=8.2 Hz, 2H); 6.94 (d, J=8.9 Hz, 2H); 5.08 (s, 2H); 3.60 (t, J=6.9 Hz, 2H); 2.62 (t, J=6.9 Hz, 2H). LCMS1 4.24 min. (M+H)=620

EXAMPLE 21

RACEMIC N-(4-{1-[4,4''-BIS(TRIFLUOROMETHOXY)-1,1':4',1''-TERPHENYL-2'-YL]ETHOXY}BENZOYL)-β-ALANINE

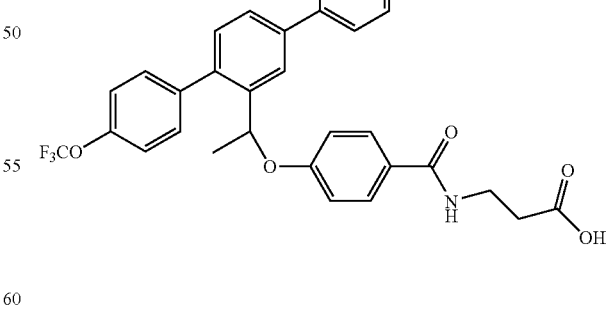

The title compound was made from racemic 1-(2,5-dichlorophenyl)ethanol and methyl 4-hydroxybenzoate using the chemistry described in EXAMPLE 1, 3 and 4. $^1$H NMR (500 MHz, CD$_3$OD): δ 7.82 (d, J=1.9 Hz, 1H); 7.68 (d, J=8.6 Hz, 2H); 7.63-7.59 (m, 3H); 7.51 (d, J=8.5 Hz, 2H); 7.44 (d, J=8.3 Hz, 2H); 7.34 (t, J=8.1 Hz, 3H); 6.70 (d, J=8.5 Hz, 2H); 5.43

(q, J=6.4 Hz, 1H); 3.57 (broad s, 2H); 2.66 (broad s, 2H); 1.71 (d, J=6.3 Hz, 3H). LCMS1 4.25 min. (M+H)=634

EXAMPLE 22

N-[4-({[4-ISOPROPOXY-4''-(TRIFLUO-ROMETHOXY)-1,1':3',1''-TERPHENYL-5'-YL]OXY}METHYL)BENZOYL]-β-ALANINE

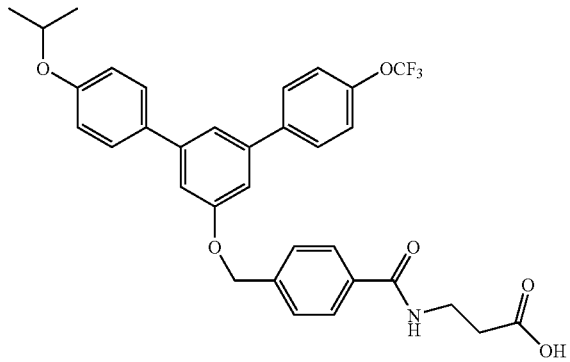

The title compound was made from 3,5-dichlorophenol and methyl 4-(bromomethyl)benzoate using the chemistry described in EXAMPLE 2 and 3. $^1$H NMR (500 MHz, CD$_3$OD): δ 7.85 (d, J=8.2 Hz, 2H); 7.75 (d, J=8.7 Hz, 2H); 7.59 (dd, J=8.3, 16.1 Hz, 4H); 7.40 (s, 1H); 7.36 (d, J=8.3 Hz, 2H); 7.19 (d, J=14.2 Hz, 2H); 6.98 (d, J=8.7 Hz, 2H); 5.30 (s, 2H); 4.65 (m, 1H); 3.63 (t, J=6.9 Hz, 2H); 2.63 (t, J=6.8 Hz, 2H); 1.34 (d, J=6.0 Hz, 6H). LCMS1 4.25 min. (M+H)=594

EXAMPLE 23

N-[4-({[4,4''-BIS(TRIFLUOROMETHOXY)-1,1':4',1''-TERPHENYL-2'-YL]OXY}METHYL)BENZOYL]-β-ALANINE

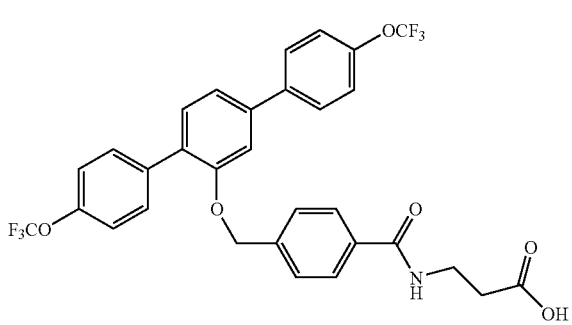

The title compound was made from 2,5-dichlorophenol and methyl 4-(bromomethyl)benzoate using the chemistry described in EXAMPLE 2 and 3. $^1$H NMR (400 MHz, CD$_3$OD): δ 7.73 (dd, J=8.3, 12.2 Hz, 4H); 7.65 (d, J=8.1 Hz, 2H); 7.44-7.38 (m, 2H); 7.36-7.26 (m, 7H); 5.25 (s, 2H); 3.59 (t, J=6.9 Hz, 2H); 2.64-2.58 (m, 2H). LCMS2 2.75 min. (M+H)=620

EXAMPLES 24A, 24B

N-[4-(1-{[4,4''-BIS(TRIFLUOROMETHOXY)-1,1':4',1''-TERPHENYL-2'-YL]OXY}ETHYL)BENZOYL]-β-ALANINE

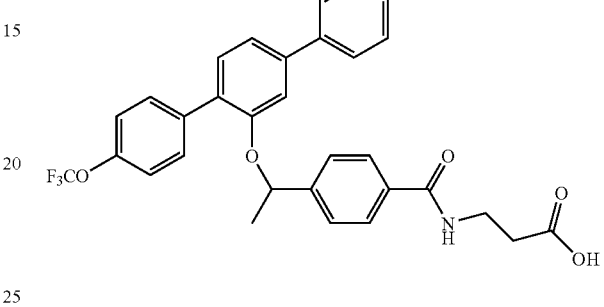

The title compounds were made from 2,5-dichlorophenol and racemic methyl 4-(1-bromoethyl)benzoate using the chemistry described in EXAMPLE 2 and 3. The title compounds were characterized as the corresponding beta alanine tert butyl esters. Representative data: $^1$H NMR (500 MHz, CDCl$_3$): δ 7.75 (d, J=8.2 Hz, 2H); 7.68 (d, J=8.6 Hz, 2H); 7.48 (d, J=8.3 Hz, 2H); 7.42-7.28 (m, 7H); 7.22 (dd, J=1.6, 7.8 Hz, 1H); 7.03 (d, J=1.5 Hz, 1H); 6.90 (t, J=5.8 Hz, 1H); 5.43 (q, J=6.4 Hz, 1H); 3.72 (q, J=5.9 Hz, 2H); 2.59 (t, J=5.9 Hz, 2H); 1.62 (d J=6.1 Hz, 3H); 1.50 (s, 9H). LCMS1 4.66 min. (M+H)= 690. The racemic tert butyl beta alanine ester intermediate was resolved on a ChiralPak AD column (2×25 cm) using an isocratic heptane/IPA eluent (flow 9 mL/min). Chiral LC3 (96/4 to 65/35 heptane/IPA over 20 min): Isomer A 17.14 min, Isomer B 20.70 min. The tert butyl group of the resolved esters was cleaved with TFA as described previously to give the title compounds. Isomer A: LCMS1 4.28 min. (M+H)= 634, Isomer B: LCMS1 4.28 min. (M+H)=634

EXAMPLE 25

N-[4-({[5'-HYDROXY-4,4''-BIS(TRIFLUO-ROMETHOXY)-1,1':4',1''-TERPHENYL-2'-YL]OXY}METHYL)BENZOYL]-β-ALANINE

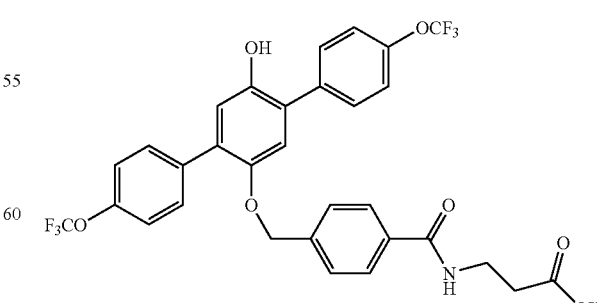

The title compound was made from 2,5-dibromobenzene-1,4-diol and methyl 4-(bromomethyl)benzoate using the chemistry described in EXAMPLE 1 and 2. The title compound was characterized as the corresponding beta alanine tert butyl ester. Data for the tert butyl beta alanine intermediate: $^1$H NMR (500 MHz, CDCl$_3$): δ 7.75 (d, J=8.2 Hz, 2H); 7.65 (d, J=8.6 Hz, 2H); 7.58 (d, J=8.4 Hz, 2H); 7.37 (dd, J=8.0, 18.2 Hz, 4H); 7.32-7.29 (m, 2H); 7.02 (s, 1H); 6.96 (s, 1H); 6.91 (t, J=6.1 Hz, 1H); 5.07 (s, 2H); 3.73 (q, J=5.8 Hz, 2H); 2.60 (t, J=5.9 Hz, 2H); 1.51 (s, 9H). LCMS1 4.25 min. (M+H)=692. The tert butyl group was cleaved with TFA as described previously to give the title compound. LCMS1 3.78 min. (M+H)=636.

EXAMPLE 26

N-[4-({[5'-PROPOXY-4,4"-BIS(TRIFLUO-ROMETHOXY)-1,1':4',1"-TERPHENYL-2'-YL]OXY}METHYL)BENZOYL]-β-ALANINE

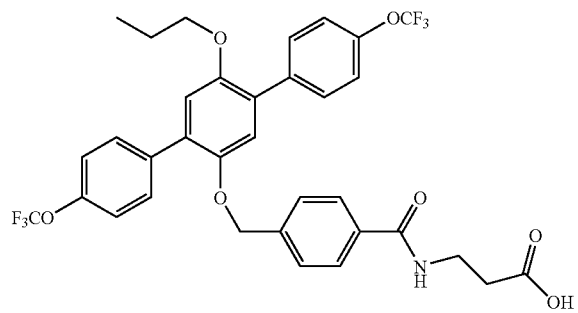

The title compound was prepared from tert-butyl N-[4-({[5'-hydroxy-4,4"-bis(trifluoromethoxy)-1,1':4',1"-terphenyl-2'-yl]oxy}methyl)benzoyl]-β-alaninate (From EXAMPLE 25) and n-propanol as described in EXAMPLE 4. $^1$H NMR (400 MHz, CD$_3$OD): δ 7.71 (d, J=8.3 Hz, 2H); 7.65 (d, J=8.7 Hz, 2H); 7.61 (d, J=8.8 Hz, 2H); 7.35 (d, J=8.2 Hz, 2H); 7.29 (t, J=7.7 Hz, 4H); 7.09 (s, 1H); 7.02 (s, 1H); 5.09 (s, 2H); 3.91 (t, J=6.3 Hz, 2H); 3.59 (t, J=6.9 Hz, 2H); 2.60 (t, J=6.9 Hz, 2H); 1.71-1.65 (m, 2H); 0.91 (t, J=7.4 Hz, 3H). LCMS1 4.43 min. (M+H)=678

EXAMPLE 27

N-(4-{2-[4'-(TRIFLUOROMETHOXY)-4-(TRIFLUOROMETHYL)BIPHENYL-3-YL]ETHYL}BENZOYL)-ε-ALANINE

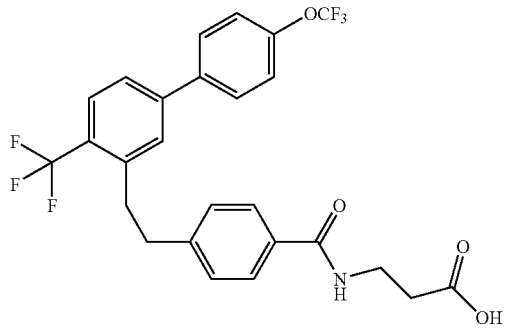

The title compound was prepared from INTERMEDIATE 12 using the chemistry described in EXAMPLE 1 and 3. $^1$H NMR (400 MHz, CD$_3$OD): δ 7.73 (dd, J=4.2, 8.2 Hz, 3H); 7.61-7.57 (m, 3H); 7.46 (s, 1H); 7.33 (d, J=8.1 Hz, 2H); 7.28 (d, J=8.2 Hz, 2H); 3.60 (t, J=6.9 Hz, 2H); 3.15 (t, J=7.8 Hz, 2H); 3.01 (t, J=7.8 Hz, 2H); 2.63-2.59 (m, 2H). LCMS1 3.99 min. (M+H)=526.

EXAMPLE 28

N-[4-(2-{3'-CHLORO-4-[4-(TRIFLUO-ROMETHOXY)PHENOXY]BIPHENYL-2-YL}ETHYL)BENZOYL]-β-ALANINE

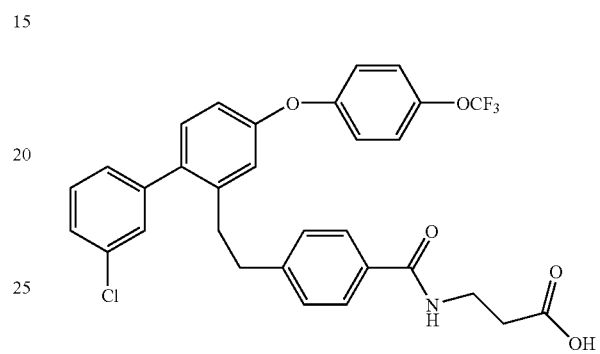

The title compound was prepared from INTERMEDIATE 11 using the chemistry described in INTERMEDIATE 8 and EXAMPLE 1 and 5. $^1$H NMR (500 MHz, CD$_3$OD): δ 7.60 (d, J=8.3 Hz, 2H); 7.38-7.34 (m, 2H); 7.25 (d, J=8.4 Hz, 2H); 7.16-7.14 (m, 3H); 7.01-6.99 (m, 2H); 6.94 (d, J=8.3 Hz, 2H); 6.90-6.84 (m, 2H); 3.70-3.60 (m, 2H); 2.87 (t, J=7.5 Hz, 2H); 2.71 (t, J=7.5 Hz, 2H); 2.63 (t, J=6.9 Hz, 2H). LCMS2 2.69 min. (M+H)=584.

EXAMPLE 29

N-(3-FLUORO-4-{2-[4'-(TRIFLUO-ROMETHOXY)-4-(TRIFLUOROMETHYL)BI-PHENYL-3-YL]ETHYL}BENZOYL)-β-ALANINE

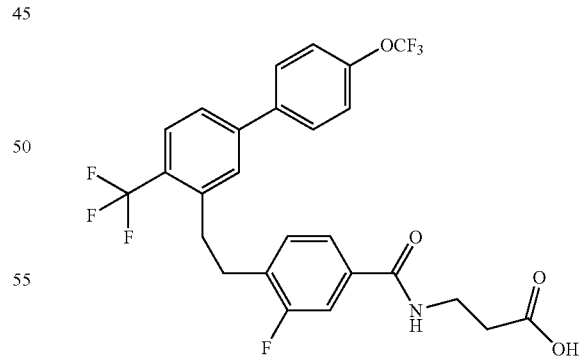

The title compound was prepared from 3-fluoro-4-methyl-benzoic acid and 2-(bromomethyl)-4-chloro-1-(trifluoromethyl)benzene using the chemistry described for the preparation of INTERMEDIATE 12 and in EXAMPLE 1 and 3. The title compound was characterized as the corresponding beta alanine tert butyl ester. Data for the tert butyl alanine intermediate: $^1$H NMR (500 MHz, CDCl$_3$): δ 7.75 (d, J=8.2 Hz, 1H); 7.55-7.53 (m, 3H); 7.51 (d, J=8.8 Hz, 1H); 7.47 (dd, J=1.5, 7.8 Hz, 1H); 7.42 (s, 1H); 7.33 (d, J=8.4 Hz, 2H); 7.29 (s, 1H); 7.25 (t, J=7.6 Hz, 1H); 6.89 (t, J=5.8 Hz, 1H); 3.73-3.69 (m, 2H); 3.17 (t, J=7.9 Hz, 2H); 3.06 (t, J=8.0 Hz, 2H); 2.60-2.56 (m, 2H); 1.49 (s, 9H). The tert butyl group was cleaved with TFA as described previously to give the title compound. LCMS1 4.02 min. (M+H)=544.

EXAMPLES 30A, 30B

N-{4-[2-(3",4"-DICHLORO-3-CYANO-1,1':4',1"-TERPHENYL-2'-YL)-1-METHYLETHYL]BENZOYL}-β-ALANINE

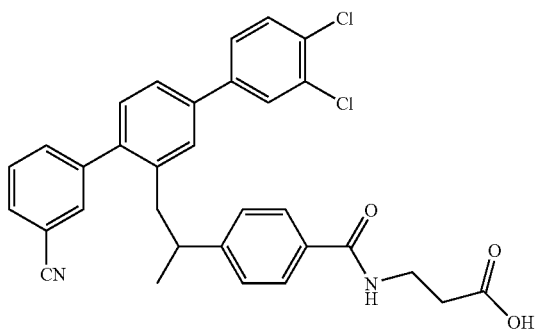

The title compounds were made from INTERMEDIATE 10 using the chemistry described for the preparation of INTERMEDIATE 8 and in EXAMPLE 2. The racemic tert butyl beta alanine intermediate was resolved on a ChiralPak AD column (2×25 cm) using an isocratic n-heptane/IPA eluent (flow 9 mL/min). Chiral LC3 (96/4 to 45/55 heptane/IPA over 20 min): Isomer A 23.57 min, Isomer B 24.29 min. The tert butyl group of the resolved esters was cleaved with TFA as described previously. Isomer A: LCMS1 4.14 min. (M+H)= 557, Isomer B: LCMS1 4.14 min. (M+H)=557. Representative $^1$H NMR (400 MHz, CD$_3$OD): δ 7.71-7.69 (m, 1H); 7.61-7.52 (m, 4H); 7.47-7.39 (m, 3H); 7.33 (d, J=1.8 Hz, 1H); 7.16 (d, J=7.9 Hz, 1H); 6.91 (d, J=8.3 Hz, 2H); 3.58 (t, J=6.9 Hz, 2H); 3.01-2.79 (m, 3H); 2.61 (t, J=7.0 Hz, 2H); 1.17 (d, J=6.6 Hz, 3H).

EXAMPLES 31A, 31B

N-(4-{2-[4,4"-BIS(TRIFLUOROMETHOXY)-1,1':4',1"-TERPHENYL-2'-YL]PROPYL}BENZOYL)-β-ALANINE

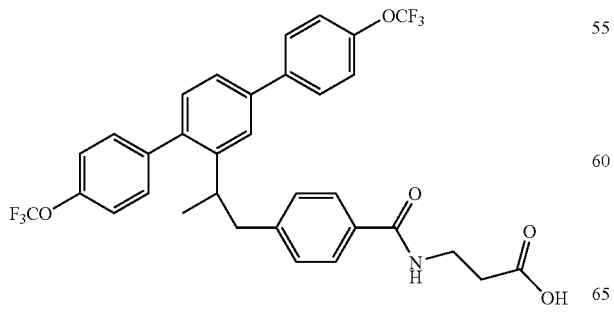

The title compound was prepared from 1-(2,5-dichlorophenyl)ethanonone using the chemistry described in EXAMPLE 1 and EXAMPLE 3. The racemic tert butyl beta alanine ester intermediate was resolved on a ChiralPak AD column (2×25 cm) using an isocratic heptane/IPA eluent (flow 9 mL/min). Chiral LC3 (96/4 to 45/55 heptane/IPA over 20 min): Isomer A 13.03 min, Isomer B 13.62 min. The tert butyl group of the resolved esters was cleaved with TFA as described previously to give the title compounds. Isomer A: LCMS1 4.40 min. (M+H)=632, Isomer B LCMS1 4.40 min. (M+H)=632. Representative $^1$H NMR (400 MHz, CD$_3$OD): δ 7.77-7.71 (m, 3H); 7.53 (d, J=8.2 Hz, 2H); 7.44 (dd, J=1.8, 7.9 Hz, 1H); 7.36 (d, J=8.0 Hz, 2H); 7.24 (d, J=7.9 Hz, 2H); 7.12 (d, J=7.9 Hz, 1H); 7.01 (d, J=7.7 Hz, 2H); 6.84 (d, J=8.2 Hz, 2H); 3.57 (t, J=6.9 Hz, 2H); 3.21-3.12 (m, 1H); 2.96-2.90 (m, 1H); 2.83 (dd, J=6.7, 13.2 Hz, 1H); 2.59 (t, J=6.9 Hz, 2H); 1.30 (d J=6.7 Hz, 3H).

EXAMPLE 32

RACEMIC N-[4-(2-{4'-(TRIFLUOROMETHOXY)-4-[4-(TRIFLUOROMETHOXY)PHENOXY]BIPHENYL-3-YL}PROPYL)BENZOYL]-β-ALANINE

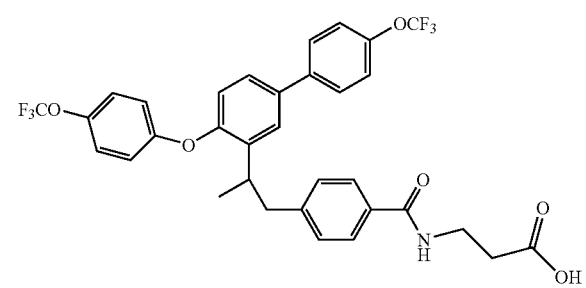

The title compound was prepared from 1-(5-bromo-2-hydroxy-phenyl)-ethanone using the chemistry described in EXAMPLE 1 and 5. $^1$H NMR (500 MHz, CD$_3$OD): δ 7.74-7.53 (m, 5H); 7.44 (dd, J=2.3, 8.4 Hz, 1H); 7.36 (d, J=8.0 Hz, 2H); 7.20 (d, J=8.4 Hz, 2H); 7.11 (d, J=8.2 Hz, 2H); 6.90 (d, J=8.4 Hz, 1H); 6.84-6.80 (m, 2H); 3.60 (t, J=6.9 Hz, 2H); 3.57-3.49 (m, 1H); 3.05 (dd, J=8.1, 13.3 Hz, 1H); 2.97 (dd, J=7.0, 13.3 Hz, 1H); 2.61 (t, J=7.0 Hz, 2H); 1.33 (d, J=6.8 Hz, 3H). LCMS2 2.86 min. (M+H)=648.

EXAMPLE 33

RACEMIC N-(4-{2-(1-METHYL-1H-PYRAZOL-5-YL)-2-[4'-(TRIFLUOROMETHOXY)BIPHENYL-3-YL]ETHYL}BENZOYL)-β-ALANINE

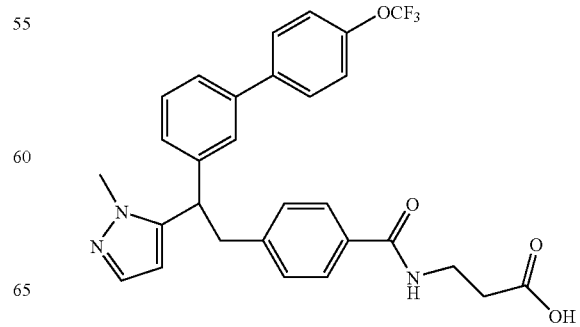

The title compound was prepared from INTERMEDIATE 13 using the procedure described in EXAMPLE 1 and 2. The title compound was characterized as the corresponding beta alanine tert butyl ester. Data for the tert butyl beta alanine intermediate: $^1$H NMR (500 MHz, CDCl$_3$): δ 7.63 (d, J=8.6 Hz, 2H); 7.49 (d, J=1.7 Hz, 1H); 7.43-7.36 (m, 3H); 7.31 (t, J=7.7 Hz, 1H); 7.28-7.23 (m, 2H); 7.08-7.11 (m, 1H); 7.06 (d, J=8.2 Hz, 2H); 6.97 (d, J=7.7 Hz, 1H); 6.85-6.81 (m, 1H); 6.40 (s, 1H); 4.25-4.21 (m, 1H); 3.71-3.63 (m, 2H); 3.55 (s, 3H); 3.53-3.47 (m, 1H); 3.24 (dd, J=8.8, 13.4 Hz, 1H); 2.55 (t, J=5.9 Hz, 2H); 1.50 (s, 9H). LCMS1 3.98 min. (M+H)=594. The tert butyl group was cleaved with TFA as described previously to give the title compound. LCMS1 3.41 min. (M+H)=538.

EXAMPLES 34A, 34B

N-(4-{2-(1H-INDAZOL-3-YL)-2-[4'-(TRIFLUO-ROMETHOXY)BIPHENYL-3-YL]ETHYL}BENZOYL)-β-ALANINE

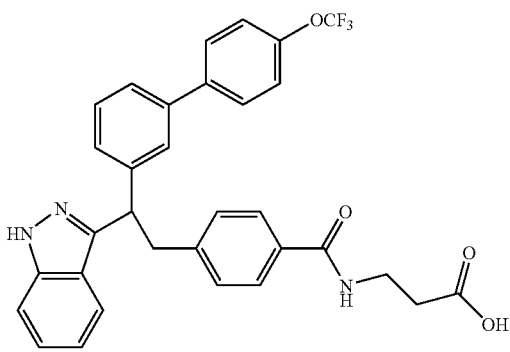

To INTERMEDIATE 14 (50 mg, 0.1 mmol) was added methanol (2 mL) and hydrazine hydrate (ca. 0.5 mL, excess). The mixture was heated at 100° C. in a screw cap tube until no starting material remained by HPLC analysis. The solution was concentrated to give the methyl 4-{2-(1H-indazol-3-yl)-2-[4'-(trifluoromethoxy)biphenyl-3-yl]ethyl}benzoate which was used without purification. LCMS14.22 min. (M+H)=517. The title compound was prepared using the chemistry described in EXAMPLE 1. The racemic tert butyl beta alanine ester intermediate was resolved on a Chiral Cel OJ column (2×25 cm) using an isocratic heptane/EtOH eluent (flow 9 mL/min). Chiral LC4 (97/3 to 80/20 heptane/EtOH over 25 min): Isomer A 22.38 min, Isomer B 26.61 min. The tert butyl group of the resolved esters was cleaved with TFA as described previously to give the title compounds. Isomer A LCMS1 3.68 min. (M+H)=574, Isomer B LCMS1 3.68 min. (M+H)=574. Representative $^1$H NMR (400 MHz, CD$_3$OD): δ 7.59-7.47 (m, 6H); 7.41 (d, J=8.4 Hz, 1H); 7.37-7.33 (m, 1H); 7.28-7.24 (m, 5H); 7.18 (d, J=8.2 Hz, 2H); 6.97 (t, J=7.5 Hz, 1H); 4.81 (t, J=8.0 Hz, 1H); 3.79 (dd, J=7.6, 13.5 Hz, 1H); 3.55-3.49 (m, 3H); 2.56 (t, J=7.0 Hz, 2H).

EXAMPLES 35A, 35B

N-(4-{2-(1-METHYL-1H-INDAZOL-3-YL)-2-[4'-(TRIFLUOROMETHOXY)BIPHENYL-3-YL]ETHYL}BENZOYL)-β-ALANINE

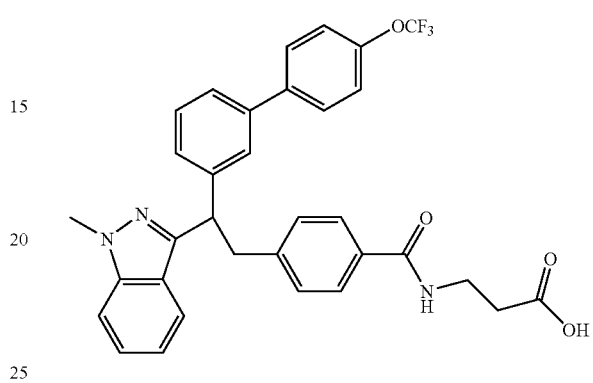

The title compound was prepared from INTERMEDIATE 14 and methyl hydrazine as described in EXAMPLE 34A/34B. The racemic tert butyl beta alanine ester intermediate was resolved on a ChiralPak AD column (2 cm×25 cm) using an isocratic heptane/IPA eluent (flow 9 mL/min). Chiral LC3 (96/4 to 65/35 heptane/IPA over 20 min): Isomer A 18.85 min, Isomer B 20.76 min. The tert butyl group of the resolved esters was cleaved with TFA as described previously to give the title compounds. Isomer A: LCMS1 3.90 min. (M+H)=588; Isomer B: LCMS1 3.90 min. (M+H)=588. Representative $^1$H NMR (400 MHz, CD$_3$OD): δ 7.60-7.46 (m, 6H); 7.40 (d, J=8.0 Hz, 1H); 7.38-7.34 (m, 1H); 7.33-7.24 (m, 5H); 7.19 (d, J=8.2 Hz, 2H); 6.99 (t, J=7.5 Hz, 1H); 4.79 (t, J=7.8 Hz, 1H) 4.01 (s, 3H); 3.83-3.76 (m, 1H); 3.56-3.47 (m, 3H); 2.56 (t, J=6.9 Hz, 2H).

EXAMPLES 36A, 36B

N-(4-{2-PHENYL-2-[4'-(TRIFLUOROMETHOXY)BIPHENYL-3-YL]ETHYL}BENZOYL)-β-ALANINE

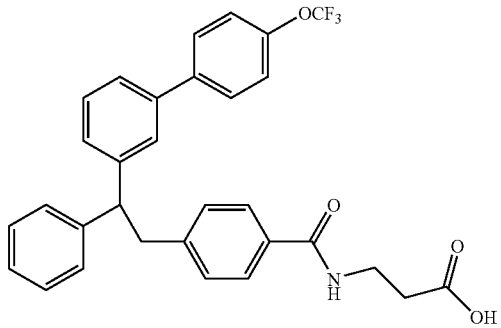

The title compounds were prepared from (3-chlorophenyl)(phenyl)methanone using the chemistry described in EXAMPLE 1 and 3. The racemic compound was resolved using chiral OD SFC—HPLC to give title compounds. Isomer A: Chiral LC2 3.388 min, LCMS1 3.95 min. (M+H)= 534. Isomer B: Chiral LC2 4.25 min, LCMS1 3.95 min. (M+H)=534. Representative $^1$H NMR (500 MHz, CDCl$_3$): δ 7.59 (d, J=9.2 Hz, 2H); 7.52-7.50 (m, 2H); 7.39-7.35 (m, 3H); 7.30-7.16 (m, 8H); 7.10 (d, J=8.2 Hz, 2H); 6.77 (t, J=6.0 Hz, 1H); 4.32 (t, J=7.9 Hz, 1H); 3.72 (q, J=5.9 Hz, 2H); 3.47 (d, J=7.8 Hz, 2H); 2.72 (t, J=5.8 Hz, 2H).

EXAMPLE 37

RACEMIC N-(4-{(5-FLUORO-1H-INDOL-3-YL)[4'-(TRIFLUOROMETHOXY)BIPHENYL-3-YL]METHYL}BENZOYL)-β-ALANINE

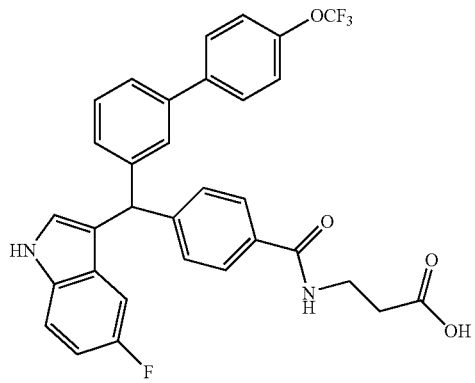

Step A. Ethyl 4-[(3-bromophenyl)(hydroxy)methyl]benzoate

A solution of i-propylmagnesium chloride (2.0M IN THF, 6.6 mL, 13.2 mmol) was added dropwise to a solution (10 mL THF) of 4-iodo ethylbenzoate (3.21 g, 11.6 mmol) cooled in an ice/methanol bath (ca. −12° C. external bath temperature). After stirring 10 minutes HPLC analysis showed consumption of the iodo starting material. A solution of 3-bromobenzaldehyde (2.78 g, 15 mmol) in 2 mL THF was added dropwise. The bath was removed and the reaction solution stirred 25 minutes. The solution was partitioned between ethyl acetate and aqueous 1N HCl. The organic phase was washed with aqueous 1N HCl, brine and dried over MgSO$_4$. The solution was filtered, concentrated and the residue purified by silica gel chromatography using a hexanes/ethyl acetate gradient to give the title compound as a yellow oil. $^1$H NNR (CDCl$_3$, 400 MHz): δ 8.02 (d, 2H, J=8.4 Hz), 7.53 (s, 1H), 7.44 (d, 2H, J=8.0 Hz), 7.42-7.38 (m, 1H), 7.28-7.17 (m, 2H), 5.84 (s, 1H), 4.36 (q, 2H, 7=8.0 Hz), 1.38 (t, 3H, J=8.0 Hz). LCMS1 3.51 min. (M+H)=335

Step B. 4-[(3-Bromophenyl)(hydroxy)methyl]benzoic acid

The title compound was made from the intermediate from Step A using the hydrolysis conditions described in EXAMPLE 1 Step G. The crude acid was used without purification. LCMS1 2.87 min. (M+H)=289

Step C. tert-Butyl N-{4-[(3-bromophenyl)(hydroxy)methyl]benzoyl}-β-alaninate The title compound was made from the intermediate from Step B using the procedure described in Example 1 Step H. LCMS1 3.33 min. (M+H)=378

Step D. tert-Butyl N-(4-{hydroxy[4'-(trifluoromethoxy)biphenyl-3-yl]methyl}benzoyl)-β-alaninate The title compound was made from the intermediate from Step C using the Suzuki conditions described in EXAMPLE 1 Step A. $^1$H NMR (400 MHz, CDCl$_3$): δ 7.68 (d, J=8.3 Hz, 2H); 7.56-7.52 (m, 3H); 7.46-7.41 (m, 3H); 7.39 (t, J=7.6 Hz, 1H); 7.33 (d, J=7.6 Hz, 1H); 7.25 (d, J=7.0 Hz, 2H); 6.90 (t, J=5.8 Hz, 1H); 5.90 (s, 1H); 3.63 (q, J=5.9 Hz, 2H); 2.51 (t, J=5.9 Hz, 2H); 1.43 (s, 9H). LCMS1 3.81 min. (M+H)=460

Step E. N-(4-{(5-fluoro-1H-indol-3-yl)[4'-trifluoromethoxy)biphenyl-3-yl]methyl}benzoyl)-β-alanine To the intermediate from Step D (16 mg, 0.03 mmol) was added DCM (1 mL), 5-fluoro-1H-indole (10 mg, 0.07 mmol) and TFA (10 drops). The solution was heated at 75° C. in a screw cap vial for 1.7 hours. The solution was then concentrated and the residue purified by RP-HPLC to give the title compound. $^1$H NMR (400 MHz, CDCl$_3$): δ 8.09 (s, 1H); 7.68 (d, J=8.2 Hz, 2H); 7.49 (d, J=8.3 Hz, 2H); 7.43 (d, J=7.8 Hz, 1H); 7.40-7.33 (m, 2H); 7.32-7.25 (m, 3H); 7.22 (d, J=8.0 Hz, 2H); 7.17 (d, J=7.6 Hz, 1H); 6.93-6.89 (m, 1H); 6.82 (dd, J=2.4, 9.6 Hz, 1H); 6.78 (t, J=5.9 Hz, 1H); 6.62 (s, 1H); 5.67 (s, 1H); 3.71 (q, J=5.8 Hz, 2H); 2.70 (t, J=5.8 Hz, 2H). LCMS1 3.80 min. (M+H)=577.

EXAMPLE 38

RACEMIC N-(4-{(4-METHOXYPHENYL)[4'-(TRIFLUOROMETHOXY)BIPHENYL-3-YL]METHYL}BENZOYL)-β-ALANINE

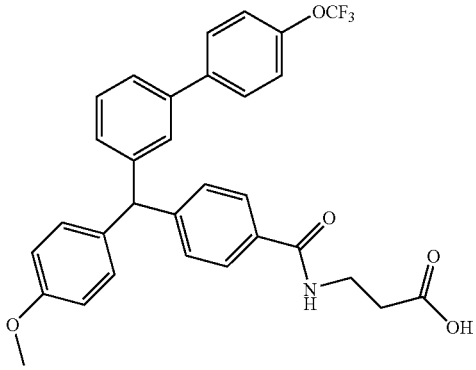

To the intermediate from EXAMPLE 37 Step D (16 mg, 0.0311 mmol) was added DCM (1 mL), methoxybenzene (10 drops) and TFA (10 drops). The solution was heated at 75° C. in a screw cap tube for 1.7 hours. The solution was then concentrated and the residue purified by RP-HPLC to give the title compound. $^1$H NMR (400 MHz, CDCl$_3$): δ 7.68 (d, J=7.9 Hz, 2H); 7.49 (d, J=8.7 Hz, 2H); 7.42-7.32 (m, 2H); 7.29-7.16 (m, 6H); 7.02 (d, J=8.2 Hz, 2H); 6.84 (d, J=8.5 Hz, 2H); 6.74

(t, J=6.0 Hz, 1H); 5.58 (s, 1H); 3.78 (s, 3H); 3.74-3.70 (m, 2H); 2.71 (t, J=5.8 Hz, 2H). LCMS1 3.90 min, (M+H)=550.

EXAMPLE 39

RACEMIC N-(4-{1-[4'-(TRIFLUOROMETHOXY)BIPHENYL-3-YL]BUT-3-EN-1-YL}BENZOYL)-β-ALANINE

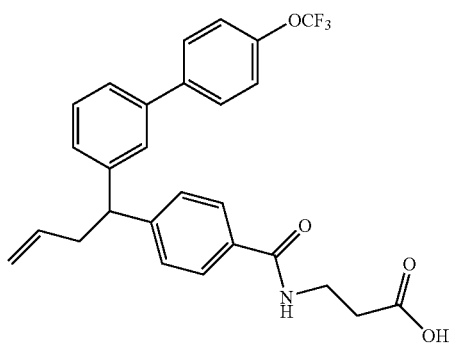

To the intermediate from EXAMPLE 37 Step D (16 mg, 0.031 mmol) was added DCM (1 mL), allyltrimethylsilane (0.3 mL, 1.9 mmol) and boron trifluoride dimethyl etherate (0.3 mL, 3.3 mmol). The solution was stirred at room temperature overnight. The solution was then partitioned between ethyl acetate and aqueous 1N HCl. The organic phase was washed with aqueous 1N HCl (2×) and concentrated. The residue was purified by RP-HPLC to give the title compound. $^1$H NMR (400 MHz, CD$_3$OD): δ 7.70 (d, J=8.3 Hz, 2H); 7.62 (d, J=8.2 Hz, 2H); 7.48 (s, 1H); 7.42-7.26 (m, 7H); 5.77-5.67 (m, 1H); 5.04-4.90 (m, 2H); 4.16 (t, J=7.9 Hz, 1H); 3.57 (t, J=6.9 Hz, 2H); 2.87 (t, J=7.4 Hz, 2H); 2.5 g (t, J=6.9 Hz, 2H). LCMS1 3.89 nm in. (M+H)=484.

EXAMPLES 40A, 40B

N-(4-{1-[4,4''-BIS(TRIFLUOROMETHOXY)-1,1':4',1''-TERPHENYL-2'-YL]ETHYL}BENZOYL)-β-ALANINE

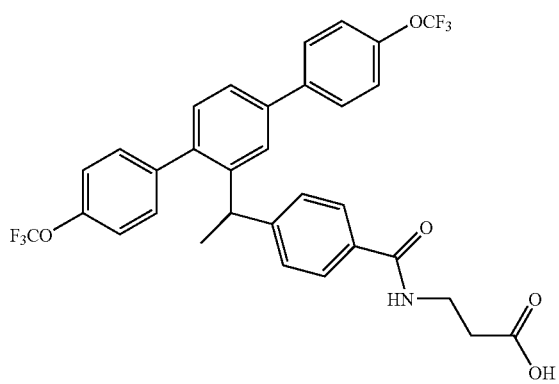

The title compounds were prepared from INTERMEDIATE 7 using the chemistry described in EXAMPLE 1 and 3. The racemic tert butyl beta alanine ester intermediate was resolved on a ChiralPak AD column (2×25 cm) using an isocratic heptane/IPA eluent (flow 9 mL/min). Chiral LC3 (90/10 heptane/IPA): Isomer A 11.59 min, Isomer B 13.20 min. The tert butyl group of the resolved esters was cleaved with TFA as described previously to give the title compounds. Isomer A: LCMS1 4.35 min. (M+H)=618, Isomer B: LCMS1 4.35 min. (M+H)=618. Representative $^1$H NMR (400 MHz, CD$_3$OD): δ 7.69-7.65 (m, 2H); 7.60 (dd, J=8.4, 17.3 Hz, 3H); 7.52 (dd, J=1.9, 7.9 Hz, 1H); 7.33 (d, J=8.0 Hz, 2H); 7.26 (m, 5H); 7.07 (d, J=8.3 Hz, 2H); 4.33 (q, J=7.1 Hz, 1H); 3.57 (t, J=6.9 Hz, 21H); 2.58 (t, J=6.9 Hz, 2H); 1.61 (d, J=7.2 Hz, 31H).

EXAMPLE 41

N-(4-{[4,4''-BIS(TRIFLUOROMETHOXY)-1,1':4',1''-TERPHENYL-2'-YL]METHYL}BENZOYL)-β-ALANINE

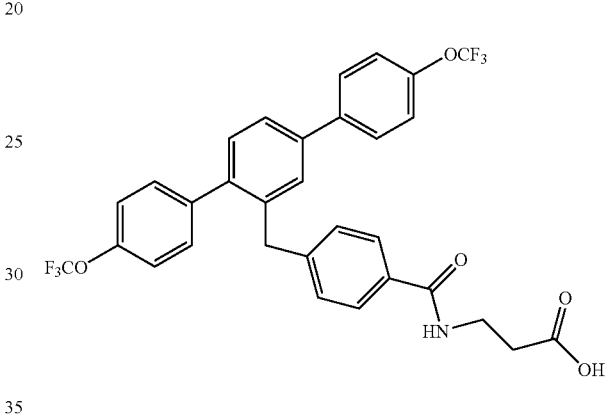

The title compound was prepared from INTERMEDIATE 16 using the chemistry described in EXAMPLE 1 and 3. $^1$H NMR (400 MHz, CD$_3$OD): δ 7.70 (d, I=7.9 Hz, 2H); 7.57 (t, J=7.9 Hz, 41H); 7.32 (d, J=9.7 Hz, 2H); 7.30-7.20 (m, 5H); 6.97 (d, J=8.3 Hz, 2H); 4.06 (s, 2H); 3.56 (t, J=6.9 Hz, 2H); 2.58 (t, J=6.9 Hz, 2H). LCMS1 4.26 min. (M+H)=604.

EXAMPLES 42A, 42B

N-(4-{1-[4-(1H-INDOL-3-YL)-4'-(TRIFLUOROMETHOXY)BIPHENYL-3-YL]ETHYL}BENZOYL)-β-ALANINE

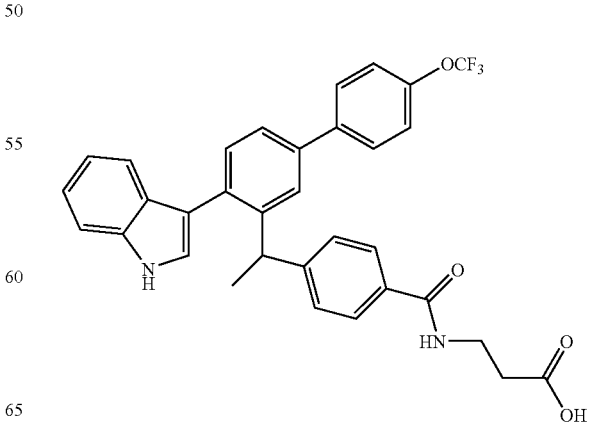

Step A. Ethyl 4-{1-[4-allyl-4'-(trifluoromethoxy)biphenyl-3-yl]ethyl}benzoate A DMF (1.5 mL) solution containing INTERMEDIATE 17 (24 mg, 0.043 mmol), allyl(tributyl)stannane (0.05 mL, 0.16 mmol), lithium chloride (20 mg, 0.47 mmol) and (PPh$_3$)$_2$PdCl$_2$ (10 mg, 0.014 mmol) was heated at 104° C. under an argon atmosphere for 45 minutes. The reaction was cooled to room temperature and partitioned between ethyl acetate and water. The organic phase was washed with water (3×) and brine and dried over MgSO$_4$. The solution was then filtered, concentrated and the residue purified by silica gel chromatography using a hexanes/ethyl acetate gradient to give the title compound. The isolated material was contaminated with 10% of the des-OTf compound. LCMS1 4.72 min. (M+H)=455.

Step B. Ethyl 4-{1-[4-(2-oxoethyl-4'-(trifluoromethoxy)biphenyl-3-yl]ethyl}benzoate Ozone was purged through a DCM solution (4 mL) cooled to −78° C. and containing the intermediate from Step A (227 mg, 0.5 mmol). The ozone purge was maintained until a slight blue color persisted (2 minutes). The solution was then purged with oxygen (to remove excess ozone). To the reaction solution was added methyl sulfide (1 mL) and PPh$_3$ (393 mg, 1.5 mmol). The solution was warm to room temperature and purified by silica gel chromatography using a hexanes/ethyl acetate gradient to give the title compound. $^1$H NMR (500 MHz, CDCl$_3$): δ 9.60 (s, J=1.9 Hz, 1H); 7.99 (d, J=8.3 Hz, 2H); 7.61-7.59 (m, 2H); 7.54 (d, J=1.7 Hz, 1H); 7.48 (dd, J=1.9, 7.8 Hz, 1H); 7.32 (d, J=8.1 Hz, 2H); 7.29-7.25 (m, 3H); 4.41-4.34 (m, 3H); 3.73 (d, J=1.9 Hz, 2H); 1.71 (d, J=7.1 Hz, 3H); 1.40 (t, J=7.1 Hz, 3H). LCMS1 4.28 min. (M+H)=411.

Step C. N-(4-{1-[4-(1H-indol-3-1)-4'-(trifluoromethoxy)biphenyl-3-yl]ethyl}benzoyl)-β-alanine The title compound was made from the intermediate from Step B using the chemistry described in EXAMPLE 1 and 3. The racemic tert butyl beta alanine ester intermediate was resolved on a ChiralPak AD column (2×25 cm) using an isocratic heptane/IPA eluent (flow 9 mL/min). Chiral LC3 (97/3 to 40/60 heptane/IPA over 20 min): Isomer A 21.72 min, Isomer B 28.54 min. The tert butyl group of the resolved esters was cleaved with TFA as described previously. Isomer A: LCMS1 3.96 min. (M+H)=573, Isomer B: LCMS13.96 min. (M+H)=573. Representative $^1$H NMR (400 MHz, CD$_3$CN): 3 9.49 (s, 1H); 7.73-7.69 (m, 2H); 7.59-7.47 (m, 5H); 7.43 (d, J=7.9 Hz, 1H); 7.36 (d, J=7.3 Hz, 3H); 7.20-7.16 (m, 1H); 7.10-7.04 (m, 5H); 4.52 (q, J=7.2 Hz, 1H); 3.51 (q, J=6.4 Hz, 2H); 2.53 (t, J=6.7 Hz, 2H); 1.60 (d, J=7.2 Hz, 3H).

EXAMPLE 43

N-(4-{[4,4"-BIS(TRIFLUOROMETHOXY)-1,1':4',1"-TERPHENYL-2'-YL]OXY}BENZOYL)-β-ALANINE

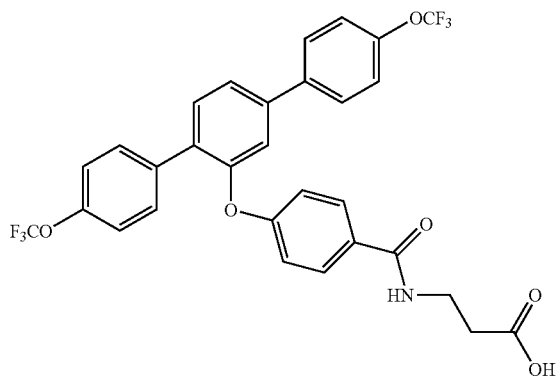

The title compound was prepared from 2,5-dichlorophenol and [4-(ethoxycarbonyl)phenyl]boronic acid using the chemistry described in EXAMPLE 1, 3 and 5. $^1$H NMR (500 MHz, CD$_3$OD): δ 7.75-7.73 (m, 4H); 7.66-7.62 (m, 4H); 7.41 (d, J=1.4 Hz, 1H); 7.32 (d, J=8.1 Hz, 2H); 7.25 (d, J=8.2 Hz, 2H); 6.88 (d, J=8.8 Hz, 2H); 3.56 (t, J=6.9 Hz, 2H); 2.57 (t, J=6.9 Hz, 2H). LCMS1 4.13 min. (M+H)=606

EXAMPLE 44

N-(4-{[4-(6-METHOXY-2-NAPHTHYL)-4'-(TRIFLUOROMETHOXY)BIPHENYL-3-YL]OXY}BENZOYL)-β-ALANINE

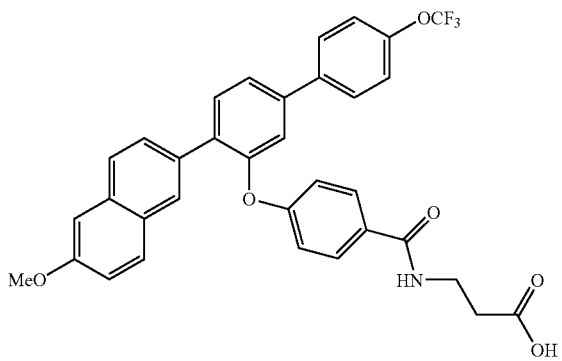

The title compound was made from INTERMEDIATE 19 using the chemistry described in EXAMPLE 1. $^1$H NMR (400 MHz, CD$_3$OD): δ 7.89 (s, 1H); 7.74 (d, J=8.8 Hz, 2H); 7.70-7.58 (m, 7H); 7.42 (d, J=1.7 Hz, 1H); 7.34 (d, J=8.2 Hz, 2H); 7.15 (d, J=2.1 Hz, 1H); 7.07 (dd, J=2.5, 8.9 Hz, 1H); 6.88 (d, J=8.8 Hz, 2H); 3.87 (s, 3H); 3.52 (t, J=6.9 Hz, 2H); 2.54 (t, J=6.9 Hz, 2H). LCMS1 4.16 min. (M+H)=602

EXAMPLES 45A, 45B

N-[4-({6-[4-(TRIFLUOROMETHOXY)PHENYL]-2,3-DIHYRO-1H-INDEN-1-YL}METHYL)BENZOYL]-β-ALANINE

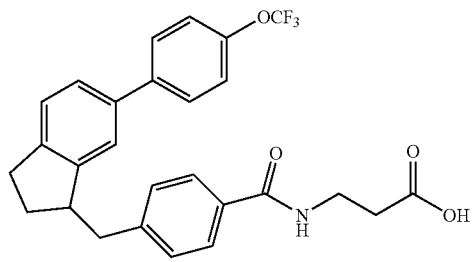

The title compound was prepared from INTERMEDIATE 8 using the chemistry described in EXAMPLE 2. The racemic tert butyl beta alanine ester intermediate was resolved on a ChiralCel OJ column (2×25 cm) using an isocratic heptane/IPA eluent (flow 9 mL/min). Chiral LC4 (96/4 to 55/45 heptane/IPA over 20 min, 0.5 mL/min): Isomer A 15.85 min, Isomer B 17.66 min. The tert butyl group of the resolved esters was cleaved with TFA as described previously to give the title compounds. Isomer A: LCMS1 4.01 min. (M+H)= 484, Isomer B: LCMS1 4.01 min. (M+H)=484. Representative $^1$H NMR (400 MHz, CD$_3$OD): δ 7.73 (d, J=8.2 Hz, 2H); 7.57-7.53 (m, 2H); 7.36 (dd, J=1.4, 7.8 Hz, 1H); 7.30-7.24 (m, 5H); 7.20 (s, 1H); 3.63-3.59 (m, 2H); 3.53-3.44 (m, 1H); 3.16 (dd, J=6.4, 13.4 Hz, 1H); 2.92-2.75 (m, 3H); 2.62 (t, J=6.9 Hz, 2H); 2.20-2.12 (m, 1H); 1.86-1.77 (m, 1H).

EXAMPLES 46A, 46B

N-[4-({7-[4-(TRIFLUOROMETHOXY)PHENYL]-1,2,3,4-TETRAHYDRONAPHTHALEN-1-YL}METHYL)BENZOYL]-β-ALANINE

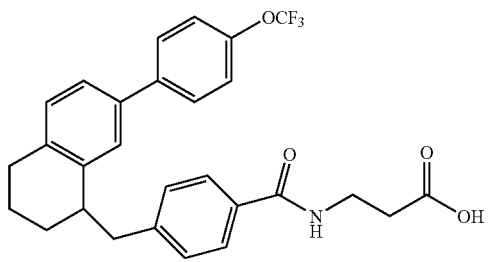

The title compounds were prepared from INTERMEDIATE 9 using the chemistry described for the preparation of INTERMEDIATE 8 and in EXAMPLE 2. The racemic tert butyl beta alanine ester intermediate was resolved on a ChiralPak AD column (2×25 cm) using an isocratic heptane/IPA eluent (flow 9 mL/min). Chiral LC3 (96/4 to 45/55 heptane/IPA over 20 min): Isomer A 17.37 min, Isomer B 18.44 min. The tert butyl group of the resolved esters was cleaved with TFA as described previously. Isomer A: LCMS1 4.11 min. (M+1)=498, Isomer B: LCMS1 4.11 min. (M+1)=498. Representative $^1$H NMR (500 MHz, CD$_3$OD): δ 7.77 (d, J=8.2 Hz, 2H); 7.53 (d, J=8.6 Hz, 2H); 7.35 (d, J=2.0 Hz, 1H); 7.32 (d, J=8.2 Hz, 2H); 7.28 (d, J=8.1 Hz, 2H); 7.21 (d, J=1.7 Hz, 1H); 7.16 (d, J=7.9 Hz, 1H); 3.65 (t, J=6.9 Hz, 2H); 3.25-3.11 (m, 2H); 2.95-2.74 (m, 3H); 2.66 (t, J=7.0 Hz, 2H); 2.01-1.92 (m, 1H); 1.81-1.69 (m, 3H).

The compounds in TABLE 1 were prepared using the chemistry described in EXAMPLES 1, 4, 5 and 6 or with following modifications: 1) EXAMPLES 47 to 50 (where $R^1$=$R^{21}$) were prepared as described in EXAMPLE 1 substituting 4-bromo-4'-(trifluoromethoxy)biphenyl-3-carbaldehyde with 2,5-dibromobenzaldehyde; 2) EXAMPLES 117 to 133 were prepared as described in EXAMPLE 1 substituting methyl 2-amino-5-bromobenzoate with methyl 5-amino-2-bromobenzoate; 3) EXAMPLES 111 to 113 were prepared from the intermediate from EXAMPLE 1 Step H using the procedure described in EXAMPLE 42A/42B.

TABLE 1

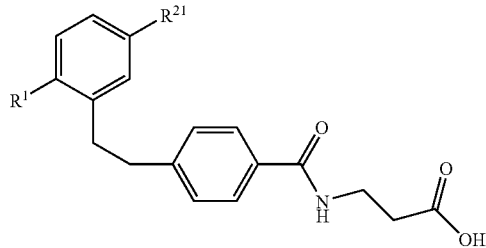

| EXAMPLE | $R^1$ | $R^{21}$ | LC-MS data |
|---|---|---|---|
| 47 | 3,5-ClPh | 3,5-ClPh | LCMS1 4.59 min (M + H) = 586 |
| 48 | 3-FPh | 3-FPh | LCMS1 3.95 min (M + H) = 486 |
| 49 | 4-FPh | 4-FPh | LCMS1 3.94 min (M + H) = 484 |
| 50 | 4-n-BuOPh | 4-n-BuOPh | LCMS1 4.62 min (M + H) = 592 |
| 51 | Ph | 4-CF$_3$OPh | LCMS1 4.20 min (M + H) = 534 |
| 52 | 4-tBuPh | 4-CF$_3$OPh | LCMS1 4.51 min (M + H) = 590 |
| 53 | 4-iPrOPh | 4-CF$_3$OPh | LCMS1 4.35 min (M + H) = 592 |
| 54 | 4-nBuOPh | 4-CF$_3$OPh | LCMS1 4.50 min (M + H) = 606 |
| 55 | 2-EtOPh | 4-CF$_3$OPh | LCMS2 2.69 min (M + H) = 578 |
| 56 | 2-iPrOPh | 4-CF$_3$OPh | LCMS1 4.30 min (M + H) = 592 |
| 57 | 4-FPh | 4-CF$_3$OPh | LCMS1 4.16 min (M + H) = 552 |
| 58 | 2-FPh | 4-CF$_3$OPh | LCMS1 4.12 min (M + H) = 552 |
| 59 | 3-ClPh | 4-CF$_3$OPh | LCMS1 4.28 min (M + H) = 568 |
| 60 | 2-ClPh | 4-CF$_3$OPh | LCMS2 2.69 min (M + H) = 568 |
| 61 | 4-CNPh | 4-CF$_3$OPh | LCMS2 2.56 min (M + H) = 559 |
| 62 | 2-CNPh | 4-CF$_3$OPh | LCMS1 3.89 min (M + H) = 559 |
| 63 | 2-CF$_3$OPh | 4-CF$_3$OPh | LCMS1 4.26 min (M + H) = 618 |
| 64 | 2-CF$_3$Ph | 4-CF$_3$OPh | LCMS2 2.68 min (M + H) = 602 |
| 65 | 4-(C$_2$H$_5$O$_2$C)Ph | 4-CF$_3$OPh | LCMS1 4.27 min (M + H) = 606 |
| 66 | 4-AcetylPh | 4-CF$_3$OPh | LCMS1 4.02 min (M + H) = 576 |

TABLE 1-continued

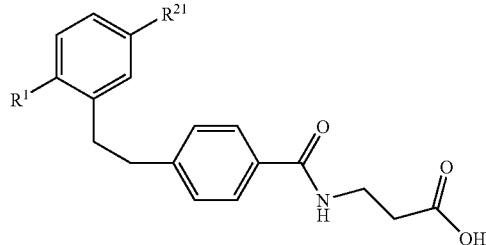

| EXAMPLE | R$^1$ | R$^{21}$ | LC-MS data |
|---|---|---|---|
| 67 | 4-MeSO$_2$Ph | 4-CF$_3$OPh | LCMS1 3.83 min (M + H) = 612 |
| 68 | 2-MeOPh | 4-CF$_3$OPh | LCMS1 4.09 min (M + H) = 564 |
| 69 | 4-MeOPH | 4-CF$_3$OPh | LCMS1 4.16 min (M + H) = 564 |
| 70 | 4-HOPh | 4-CF$_3$OPh | LCMS2 2.46 min (M + H) = 550 |
| 71 | 4-CF$_3$Ph | 4-CF$_3$OPh | LCMS1 4.32 min (M + H) = 602 |
| 72 | 3-NO$_2$Ph | 4-CF$_3$OPh | LCMS1 4.08 min (M + H) = 579 |
| 73 | 4-NO$_2$Ph | 4-CF$_3$OPh | LCMS1 4.11 min (M + H) = 579 |
| 74 | 4-CO$_2$HPh | 4-CF$_3$OPh | LCMS1 3.85 min (M + H) = 578 |
| 75 | 4-(N,N-dimethyl)Ph | 4-CF$_3$OPh | LCMS2 2.27 min (M + H) = 577 |
| 76 | 4-(NMe$_2$CH$_2$)Ph | 4-CF$_3$OPh | LCMS1 2.22 min (M + H) = 591 |
| 77 | 4-(NH$_2$CO)Ph | 4-CF$_3$OPh | LCMS1 3.64 min (M + H) = 577 |
| 78 | 4-(NHMeCO)Ph | 4-CF$_3$OPh | LCMS1 3.73 min (M + H) = 591 |
| 79 | 4-(NMe$_2$CO)Ph | 4-CF$_3$OPh | LCMS1 3.84 min (M + H) = 605 |
| 80 | 2,4-ClPh | 4-CF$_3$OPh | LCMS1 4.36 min (M + H) = 602 |
| 81 | 2-EtO, 4-ClPh | 4-CF$_3$OPh | LCMS2 2.78 min (M + H) = 612 |
| 82 | 3-Cl, 4-nPrOPh | 4-CF$_3$OPh | LCMS1 4.47 min (M + H) = 626 |
| 83 | 3-Cl, 4-EtOPh | 4-CF$_3$OPh | LCMS1 4.35 min (M + H) = 612 |
| 84 | 3-F, 4-EtOPh | 4-CF$_3$OPh | LCMS2 2.72 min (M + H) = 596 |
| 85 | 3-Cl, 4-MeOPh | 4-CF$_3$OPh | LCMS1 4.23 min (M + H) = 598 |
| 86 | 3-F, 4-MeOPh | 4-CF$_3$OPh | LCMS2 2.64 min (M + H) = 582 |
| 87 | 3,4-ClPh | 4-CF$_3$OPh | LCMS1 4.37 min (M + H) = 602 |
| 88 | 3-Cl, 4-FPh | 4-CF$_3$OPh | LCMS1 4.27 min (M + H) = 586 |
| 89 | 3,5-ClPh | 4-CF$_3$OPh | LCMS1 4.43 min (M + H) = 602 |
| 90 | 2,3,5-FPh | 4-CF$_3$OPh | LCMS2 2.64 min (M + H) = 588 |
| 91 | 3-CN, 4-F Ph | 4-CF$_3$OPh | LCMS1 4.04 min (M + H) = 577 |
| 92 | 3-F, 4-CN Ph | 4-CF$_3$OPh | LCMS1 4.07 min (M + H) = 577 |
| 93 | 2-F, 5-CF$_3$ Ph | 4-CF$_3$OPh | LCMS1 4.27 min (M + H) = 620 |
| 94 | 2-F, 5-CN Ph | 4-CF$_3$OPh | LCMS1 3.98 min (M + H) = 577 |
| 95 | 2-MeO, 5-NO$_2$ Ph | 4-CF$_3$OPh | LCMS1 4.02 min (M + H) = 609 |
| 96 | 2-MeO, 5-CN Ph | 4-CF$_3$OPh | LCMS1 3.93 min (M + H) = 589 |
| 97 | 4-Pyridyl | 4-CF$_3$OPh | LCMS1 3.07 min (M + H) = 535 |
| 98 | 3-Pyridyl | 4-CF$_3$OPh | LCMS1 3.11 min (M + H) = 535 |
| 99 | 6-EtO, 2-Naphthyl | 4-CF$_3$OPh | LCMS1 2.86 min (M + H) = 628 |
| 100 | 5-CN, 2-Indole | 4-CF$_3$OPh | LCMS1 3.96 min (M + H) = 598 |
| 101 | 4-(1-pyrazole)phenyl | 4-CF$_3$OPh | LCMS1 4.11 min (M + H) = 600 |
| 102 | 2-F, 4-pyridyl | 4-CF$_3$OPh | LCMS1 4.17 min (M + H) = 553 |
| 103 | 2-Cl, 4-pyridyl | 4-CF$_3$OPh | LCMS1 4.30 min (M + H) = 569 |
| 104 | 1-imidazole | 4-CF$_3$OPh | LCMS1 2.97 min (M + H) = 524 |
| 105 | 5-pyrazole | 4-CF$_3$OPh | LCMS1 3.93 min (M + H) = 589 |
| 106 | 3-(1-pyrazole)Ph | 4-CF$_3$OPh | LCMS1 4.08 min (M + H) = 600 |
| 107 | 2,6-Pyrimidine | 4-CF$_3$OPh | LCMS1 4.24 min (M + H) = 536 |
| 108 | 3,5-Pyrimidine | 4-CF$_3$OPh | LCMS1 2.26 min (M + H) = 536 |
| 109 | 2-MeO, 5-Pyridyl | 4-CF$_3$OPh | LCMS1 3.14 min (M + H) = 565 |
| 110 | 3-Indole | 4-CF$_3$OPh | LCMS1 4.06 min (M + H) = 573 |
| 111 | 5-CF$_3$O, 3-Indole | 4-CF$_3$OPh | LCMS1 4.24 min (M + H) = 657 |
| 112 | 5-CF$_3$, 3-Indole | 4-CF$_3$OPh | LCMS1 4.19 min (M + H) = 641 |
| 113 | 4,6-Cl, 3-Indole | 4-CF$_3$OPh | LCMS1 4.28 min (M + H) = 641 |
| 114 | Br | 4-CF$_3$OPh | LCMS1 4.01 min (M + H) = 538 |
| 115 | H | 4-CF$_3$OPh | LCMS1 3.86 min (M + H) = 458 |
| 116 | cyclopropyl | 4-CF$_3$OPh | LCMS1 4.09 min (M + H) = 498 |
| 117 | 4-CF$_3$OPh | Br | LCMS1 4.01 min (M + H) = 536 |
| 118 | 4-CF$_3$OPh | 4-F Ph | LCMS1 4.20 min (M + H) = 552 |
| 119 | 4-CF$_3$OPh | 4-tBu Ph | LCMS1 4.61 min (M + H) = 590 |
| 119 | 4-CF$_3$OPh | 3-Cl, 4-F Ph | LCMS1 4.36 min (M + H) = 586 |
| 120 | 4-CF$_3$OPh | 3-Cl, 4-nPrO Ph | LCMS1 4.56 min (M + H) = 626 |
| 121 | 4-CF$_3$OPh | 3-Cl, 4-EtO Ph | LCMS1 4.41 min (M + H) = 612 |
| 122 | 4-CF$_3$OPh | 3-Cl, 4-MeO Ph | LCMS1 4.26 min (M + H) = 598 |
| 123 | 4-CF$_3$OPh | 3,5-Cl Ph | LCMS1 4.56 min (M + H) = 602 |
| 124 | 4-CF$_3$OPh | 2,4-Cl Ph | LCMS1 4.47 min (M + H) = 602 |
| 125 | 4-CF$_3$OPh | 2-EtO, 4-Cl Ph | LCMS1 4.43 min (M + H) = 612 |
| 126 | 4-CF$_3$OPh | 3-F, 4-EtO Ph | LCMS1 4.26 min (M + H) = 596 |
| 127 | 4-CF$_3$OPh | 2-CF$_3$ Ph | LCMS1 4.26 min (M + H) = 602 |
| 128 | 4-CF$_3$OPh | 2,3,5-F Ph | LCMS1 4.24 min (M + H) = 588 |
| 129 | 4-CF$_3$OPh | 2-EtO Ph | LCMS1 4.26 min (M + H) = 578 |
| 130 | 4-CF$_3$OPh | 2-Cl Ph | LCMS1 4.25 min (M + H) = 568 |

TABLE 1-continued

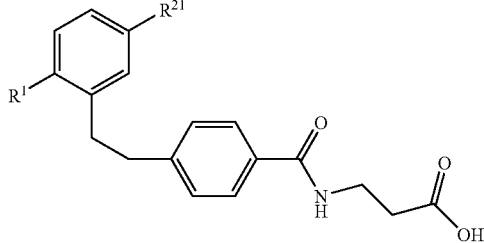

| EXAMPLE | R¹ | R²¹ | LC-MS data |
| --- | --- | --- | --- |
| 131 | 4-CF₃OPh | 3-Cl Ph | LCMS1 4.35 min (M + H) = 568 |
| 132 | 4-CF₃OPh | 3-F, 4-MeO Ph | LCMS1 4.14 min (M + H) = 582 |
| 133 | 4-CF₃OPh | 3,4-Cl Ph | LCMS1 4.50 min (M + H) = 602 |
| 134 | OH | 4-CF₃OPh | LCMS1 3.41 min (M + H) = 474 |
| 135 | O-n-propyl | 4-CF₃OPh | LCMS1 4.16 min (M + H) = 516 |
| 136 | OPh | 4-CF₃OPh | LCMS1 4.18 min (M + H) = 550 |
| 137 | OPh | 3,4-Cl Ph | LCMS1 4.30 min (M + H) = 534 |
| 138 | O-(4-MeO Ph) | 3,4-Cl Ph | LCMS1 4.26 min (M + H) = 564 |
| 139 | O-(3-CN Ph) | 3,4-Cl Ph | LCMS1 4.12 min (M + H) = 559 |
| 140 | O-(3-F, 4-MeO PH) | 3,4-Cl Ph | LCMS1 4.24 min (M + H) = 582 |
| 141 | O-(3-MeO Ph) | 3,4-Cl Ph | LCMS1 4.28 min (M + H) = 564 |
| 142 | O-(4CF₃O Ph) | 3,4-Cl Ph | LCMS1 4.45 min (M + H) = 618 |
| 143 | O-(4-F Ph) | 3,4-Cl Ph | LCMS1 4.27 min (M + H) = 552 |
| 144 | O-(4-CN Ph) | 3,4-Cl Ph | LCMS1 4.09 min (M + H) = 559 |
| 145 | O-(4-F Ph) | 4-CF₃OPh | LCMS1 4.18 min (M + H) = 568 |

Following the procedure outlined in EXAMPLE 13 the racemic compounds listed in TABLE 2 were prepared.

TABLE 2

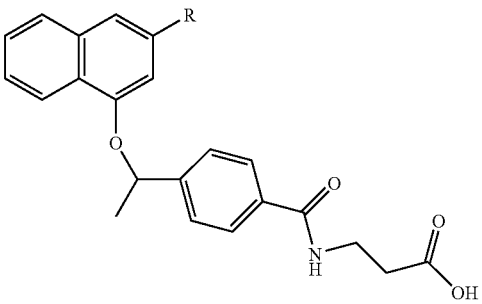

| EXAMPLE | R | LC-MS data |
| --- | --- | --- |
| 146 | 3,5-Cl Ph | LCMS1 4.15 min, (M + H) = 508 |

TABLE 2-continued

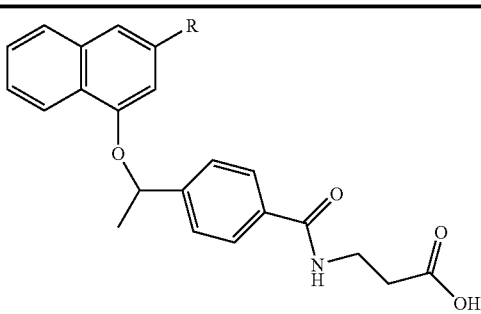

| EXAMPLE | R | LC-MS data |
| --- | --- | --- |
| 147 | 3 Cl, 4-nPrO Ph | LCMS2 2.72 min, (M + H) = 532 |

The compounds listed in TABLE 3 were prepared from INTERMEDIATE 6 as described for EXAMPLE 17.

TABLE 3

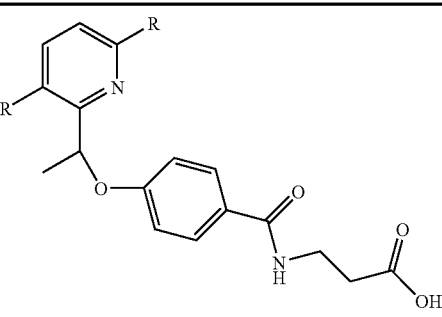

| EXAMPLE | R | Isomer | LCMS Data |
| --- | --- | --- | --- |
| 148 | 4-CF₃OPh | Enantiomer A (Faster Eluting) | LCMS1 4.10 min. (M + H) = 635 |

TABLE 3-continued

| EXAMPLE | R | Isomer | LCMS Data |
|---|---|---|---|
| 149 | 4-CF$_3$OPh | Enantiomer B (Slower Eluting) | LCMS1 4.10 min. (M + H) = 635 |
| 150 | 4F Ph | Racemic | LCMS1 3.66 min. (M + H) = 503 |

The compounds in TABLE 4 were prepared as described for EXAMPLE 22.

TABLE 4

| EXAMPLE | R$^1$ | R' | LCMS Data |
|---|---|---|---|
| 151 | Cl | 4-CF$_3$OPh | LCMS2 2.52 min (M + H) = 494 |
| 152 | 4-CF$_3$OPh | 4-CF$_3$OPh | LCMS2 2.76 min. (M + H) = 620 |
| 153 | 4-nBuO Ph | 4-CF$_3$OPh | LCMS2 4.44 min (M + H) = 608 |

The compounds in TABLE 5 were prepared as described for EXAMPLE 11, 24A/24B, 25 and 26.

TABLE 5

| EXAMPLE | R$^1$ | R$^{21}$ | R$^3$ | LC-MS data |
|---|---|---|---|---|
| 154 | 3,5-Cl Ph | OH | H | LCMS1 3.93 min. (M + H) = 604 |
| 155 | 3,5-Cl Ph | OPr | H | LCMS1 4.71 min. (M + H) = 646 |
| 156 | 4-CF$_3$OPh | OMe | Me Racemic | LCMS1 4.23 min. (M + H) = 664 |
| 157 Keith | 4-iPrO Ph | H | Me Racemic | LCMS1 4.03 min. (M + H) = 582 |
| 158 | 4-F Ph | H | Me Racemic | LCMS1 3.87 min. (M + H) = 502 |

TABLE 5-continued

[Structure: R21 and R1 on benzene ring (with additional R1), connected via O-CH(R3) to phenyl-C(O)NHCH2CH2CO2H]

| EXAMPLE | R¹ | R²¹ | R³ | LC-MS data |
|---|---|---|---|---|
| 159 | 4-CF₃OPh | CN | Me Enantiomer A | LCMS1 4.13 min. (M + H) = 659 |
| 160 | 4-CF₃OPh | CN | Me Enantiomer B | LCMS1 4.13 min. (M + H) = 659 |

The compounds listed in TABLE 6 were prepared from INTERMEDIATE 10 as described for EXAMPLE 30A/30B.

TABLE 6

[Structure: R¹ and R²¹ on benzene ring, connected via CH2-CH(R3) to phenyl-C(O)NH-CH2CH2-C(O)OH]

| Example | R¹ | R²¹ | R³ | LC-MS data |
|---|---|---|---|---|
| 161 | 3-CN Ph | 4-CF₃OPh | Me Enantiomer A | LCMS1 4.06 min. (M + H) = 573 |
| 162 | 3-CN Ph | 4-CF₃OPh | Me Enantiomer B | LCMS1 4.06 min. (M + H) = 573 |
| 163 | 2-CF₃ Ph | 4-CF₃OPh | Me Racemic | LCMS3 1.36 min (M + H) = 616 |
| 164 | 2-CF₃ Ph | 4-CF₃ Ph | Me Racemic | LCMS3 1.35 min (M + H) = 600 |
| 165 | 2-CF₃ Ph | 3,4-Cl Ph | Me Racemic | LCMS3 1.38 min (M + H) = 600 |
| 166 | 2-CF₃ Ph | 2-Naphthyl | Me Racemic | LCMS3 1.35 min (M + H) = 582 |
| 167 | 2-CF₃ Ph | 6 MeO, 2-Naphthyl | Me Racemic | LCMS3 1.35 min (M + H) = 612 |
| 168 | 2-CF₃ Ph | 3-Quinoline | Me Racemic | LCMS3 1.07 min (M + H) = 583 |
| 169 | 3-Cl Ph | 3,4-Cl Ph | Me Racemic | LCMS1 4.45 min. (M + H) = 566. |

The compounds listed in TABLE 7 were prepared as described for EXAMPLES 31A/31B and 32.

TABLE 7

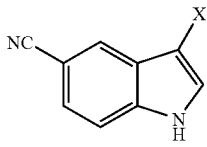

| Example | R$^1$ | R$^{21}$ | Isomer | LC-MS data |
|---|---|---|---|---|
| 170 | F | 4-CF$_3$OPh | A (derived from faster eluting enantiomer) | LCMS1 3.91 min, (M + H) 490 |
| 171 | F | 4-MeOPh | A | LCMS1 3.59 min, (M + H) 436 |
| 172 | F | 4-CF$_3$Ph | A | LCMS1 3.87 min, (M + H) 474 |
| 173 | F | 3,4-Cl Ph | A | LCMS1 3.98 min, (M + H) 474 |
| 174 | F | 4-CF$_3$OPh | B (derived from slower eluting enantiomer) | LCMS1 3.91 min, (M + H) 490 |
| 175 | F | 4-MeO Ph | B | LCMS1 3.59 min, (M + H) 436 |
| 176 | F | 4-CF$_3$ OPh | B | LCMS1 3.98 min, (M + H) 474 |
| 177 | F | 3,4-Cl Ph | B | LCMS1 3.98 min, (M + H) 474 |
| 178 | 4-CN Ph | 4-CN Ph | Racemic | LCMS1 3.68 min. (M + H) = 514 |
| 179 | O-(4-F Ph) | 4-CF$_3$OPh | Racemic | LCMS2 4.20 min. (M + H) = 582 |

The compounds listed in TABLE 8 were prepared as described for EXAMPLE 3.

TABLE 8

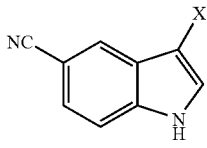

| EXAMPLE | R$^3$ | Isomer | LC-MS data |
|---|---|---|---|
| 180 | 5-CN-indol-3-yl | A (derived from faster eluting enantiomer) | LCMS1 3.72 min. (M + H) = 598 |
| 181 | 5-CN-indol-3-yl | B | LCMS1 3.72 min. (M + H) = 598 |

TABLE 8-continued

[Structure: biphenyl with OCF3, connected via CH(R3) to benzamide-NH-CH2CH2-COOH]

| EXAMPLE | R³ | Isomer | LC-MS data |
|---|---|---|---|
| 182 | 4,6-difluoroindol-3-yl (X = point of attachment) | Racemic | LCMS1 3.86 min. (M + H) = 609. |
| 183 | 5-(trifluoromethoxy)indol-3-yl (X = point of attachment) | Racemic | LCMS1 3.95 min. (M + H) = 657. |

X shows the point of attachment.

The compounds listed in TABLE 9 were prepared from the indicated precursors as described for EXAMPLE 39 and 40.

TABLE 9

[Structure: phenyl with R¹ and R²¹ substituents, connected via CH(R³) to benzamide-NH-CH2CH2-COOH]

| EXAMPLE | Precursor | R¹ | R²¹ | R³ | LC-MS data |
|---|---|---|---|---|---|
| 184 | INTERMEDIATE 16 | 4-nBuOPh | 4-nBuOPh | H | LCMS1 4.60 min. (M + H) = 580. |
| 185 | 1-(2,5-dichloro-phenyl)propan-1-one | 4-CF₃OPh | 4-CF₃OPh | Et Enantiomer A | LCMS1 4.36 min. (M + H) = 632. |
| 186 | 1-(2,5-dichloro-phenyl)propan-1-one | 4-CF₃OPh | 4-CF₃OPh | Et Enantiomer B | LCMS1 4.36 min. (M + H) = 632. |
| 187 | INTERMEDIATE 17 | 3-CNPh | 4-CF₃OPh | Me Enantiomer A | LCMS1 3.94 min. (M + H) = 559 |
| 188 | INTERMEDIATE 17 | 3-CNPh | 4-CF₃OPh | Me Enantiomer B | LCMS1 3.94 min. (M + H) = 559 |
| 189 | INTERMEDIATE 18 | 3-CNPh | 4-CF₃OPh | H | LCMS1 3.88 min. (M + H) = 545. |
| 190 | INTERMEDIATE 18 | Ph | 4-CF₃OPh | H | LCMS1 4.03 min. (M + H) = 520. |
| 191 | INTERMEDIATE 18 | 6-MeO, 2-Naphthyl | 4-CF₃OPh | H | LCMS1 4.28 min. (M + H) = 600 |
| 192 | INTERMEDIATE 15 | O(4-FPh) | 4-CF₃OPh | Me Racemic | LCMS2 2.70 min. (M + H) = 568 |
| 193 | EXAMPLE 37 Step C | H | 4-CF₃OPh | n-Propyl Racemic | LCMS1 4.01 min. (M + H) = 486 |

TABLE 9-continued

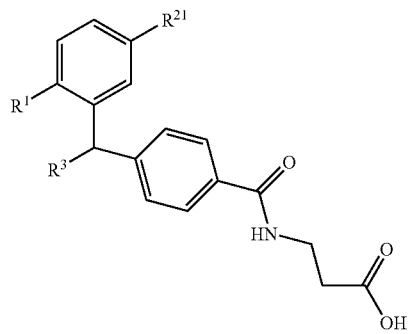

| EXAMPLE | Precursor | R¹ | R²¹ | R³ | LC-MS data |
|---|---|---|---|---|---|
| 194 | EXAMPLE 37 Step C | H | 3,5-ClPh | n-Propyl Racemic | LCMS1 4.16 min. (M + H) = 470 |
| 195 | EXAMPLE 37 Step C | H | 2-F, 5-CF₃Ph | n-Propyl Racemic | LCMS1 3.94 min. (M + H) = 488 |
| 196 | EXAMPLE 37 Step C | H | 4-ClPh | n-Propyl Racemic | LCMS1 3.95 min. (M + H) = 436 |
| 197 | EXAMPLE 37 Step C | H | 4-CF₃Ph | n-Propyl Racemic | LCMS1 3.98 min. (M + H) = 470 |
| 198 | EXAMPLE 37 Step C | H | 4-tButylPh | n-Propyl Racemic | LCMS1 4.22 min. (M + H) = 458 |

The compounds listed in TABLE 10 were prepared from INTERMEDIATE 19 and 20 as described for EXAMPLE 43 and 44.

TABLE 10

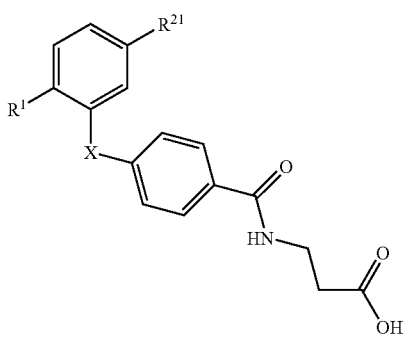

| Example | R¹ | R²¹ | X | LC-MS data |
|---|---|---|---|---|
| 199 | 4-ClPh | 4-CF₃OPh | O | LCMS1 4.15 min. (M + H) = 556 |
| 200 | 3,4-FPh | 4-CF₃OPh | O | LCMS1 3.98 min. (M + H) = 558 |
| 201 | 3-CNPh | 4-CF₃OPh | O | LCMS1 3.87 min. (M + H) = 547 |
| 202 | 2-CF₃Ph | 4-CF₃OPh | O | LCMS1 4.04 min. (M + H) = 590 |
| 203 | 3,5-ClPh | 4-CF₃OPh | O | LCMS1 4.33 min. (M + H) = 590 |
| 204 | 6-MeO, 2-Naphthyl | 3,5-ClPh | O | LCMS1 4.36 min. (M + H) = 586 |
| 205 | 4-CF₃OPh | 4-CF₃OPh | S | LCMS1 4.29 min. (M + H) = 622 |

The racemic compound listed in TABLE 11 was prepared from INTERMEDIATE 9 as described for EXAMPLE 46A/46B.

TABLE 11

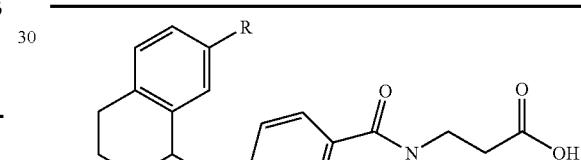

| EXAMPLE | R | LC-MS DATA |
|---|---|---|
| 206 | 3,4-ClPh | LCMS1 4.20 MIN (M + H) = 482 |

EXAMPLES 207A, 207B, 207C

N-(4-{2-(1H-INDOL-3-YL)-1-METHYL-2-[4'-(TRIFLUOROMETHOXY)BIPHENYL-3-YL]ETHYL}BENZOYL)-β-ALANINE

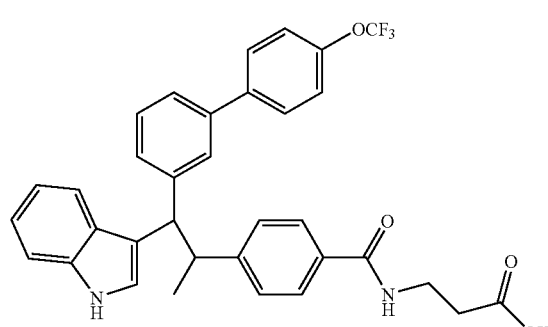

Step A. 4-Methoxybenzyl (3-bromophenyl)acetate

A DMF (30 mL) solution of (3-bromophenyl)acetic acid (2.5 g, 11.6 mmol), cesium carbonate (3.78 g, 11.6 mmol) and 4-methoxybenzyl chloride (1.82 g, 11.6 mmol) was stirred overnight at room temperature. The solution was then partitioned between ethyl acetate and water. The organic phase was washed with water (3×), brine and dried over magnesium sulfate. The solution was filtered, concentrated and the residue purified by silica gel chromatography using a hexanes/ethyl acetate gradient to give the title compound. $^1$H NMR (400 MHz, CDCl$_3$): δ 7.43-7.39 (m, 2H); 7.29-7.24 (m, 2H); 7.20-7.16 (m, 2H); 6.90-6.86 (m, 2H); 5.07 (s, 2H); 3.81 (s, 3H); 3.60 (s, 2H). LCMS1 3.70 min.

Step B. Methyl 4-{2-(3-bromophenyl)-3-[(4-methoxybenzyl)oxy]-1-methyl-3-oxopropyl}benzoate LHMDS (1.0M THF, 2.6 mL) was added dropwise to a −78° C. THF (4 mL) solution containing the intermediate from Step A (0.827 g, 2.47 mmol). After stirring 10 minutes a THF (4 mL) solution containing methyl 4-(1-bromoethyl) benzoate (0.6 g, 2.47 mmol) was added dropwise. The solution was allowed to warm to room temperature. After 1.5 hours the solution was partitioned between ethyl acetate and aqueous 1N HCl. The organic phase was washed with water, brine and dried over magnesium sulfate. The solution was filtered and the residue purified by silica gel chromatography using a hexanes/ethyl acetate gradient to give the title compounds as a 1.67/1 mixture of diastereomers. $^1$H NMR (400 MHz, CDCl$_3$): selected data δ 5.16 (d, J=12.0 Hz); 5.01 (d, J=12.0 Hz); 4.82 (d, J=12.0 Hz); 4.64 (d, J=11.9 Hz); 1.34 (d, J=6.8 Hz); 1.02 (d, J=7.0 Hz). Minor diastereomer: LCMS1 4.08 min (N+Na)=519. Major diastereomer: LCMS1 4.19 min (M+Na)=519.

Step C. 2-(3-Bromophenyl)-3-[4-(methoxycarbonyl) phenyl]butanoic acid

The intermediate from Step B (0.8 g, 1.6 mmol) was treated with 4-methoxy benzene (2 mL) and trifluoroacetic acid (15 mL). After stirring for 1.5 hours the solution was concentrated and the residue purified by silica gel chromatography using a hexanes/ethyl acetate gradient (containing 0.05% acetic acid) to give the title compounds as mixture of diastereomers. $^1$H NMR (400 MHz, CDCl$_3$): selected data δ3.90 (s); 3.85 (s); 3.72-3.64 (m); 3.52-3.42 (m); 1.39 (d, J=6.8 Hz); 1.03 (d, J=7.0 Hz). LCMS1 3.34 min. (M+H)=377. LCMS1 3.57 min. (N+H)=377.

Step D. Methyl 4-[2-(3-bromophenyl)-3-hydroxy-1-methylpropyl]benzoate

BOP (152 mg, 0.345 mmol) was added to a THF (2 mL) solution containing the intermediate from Step C (100 mg, 0.265 mmol) and DIEA (0.06 ml, 0.344 mmol). After stirring for 5 minutes sodium borohydride (20 mg, 0.53 mmol) was added to the solution. The solution was stirred for 15 minutes and then partitioned between aqueous 1N HCl and ethyl acetate. The organic phase was washed with brine and dried over magnesium sulfate. The solution was filtered and the residue purified by silica gel chromatography using a hexanes/ethyl acetate gradient to give the title compounds as a mixture of diastereomers. A portion of the isolated material also contained single diastereomeric products. Diastereomer A: $^1$H NMR (400 MHz, CDCl$_3$): δ 8.01 (d, J=8.3 Hz, 2H); 7.48-7.40 (m, 2H); 7.33 (d, J=8.3 Hz, 2H); 7.26-7.19 (m, 2H); 3.92 (s, 3H); 3.59-3.47 (m, 2H); 3.10-3.04 (m, 1H); 2.92-2.88 (m, 1H); 1.05 (d, J=6.9 Hz, 3H). LCMS1 3.60 min. (M−H$_2$O)= 345. Diastereomer B: $^1$H NMR (400 MHz, CDCl$_3$): δ 7.82 (d, J=8.3 Hz, 2H); 7.17-7.13 (m, 1H); 7.04-6.96 (m, 4H); 6.85 (d, J=7.7 Hz, 1H); 4.00-3.88 (m, 2H); 3.87 (s, 3H); 3.26-3.18 (m, 1H); 3.02-2.96 (m, 1H); 1.37 (d, J=6.9 Hz, 3H). LCMS1 3.40 min. (M−H$_2$O)=345.

Step E. Methyl 4-{1-methyl-3-oxo-2-[4'-(trifluoromethoxy)biphenyl-3-yl]propyl}benzoate The intermediate from Step D was subjected to the Suzuki conditions described in EXAMPLE 1 Step A to give methyl 4-{3-hydroxy-1-methyl-2-[4'-(trifluoromethoxy)biphenyl-3-yl]propyl}benzoate as a mixture of diastereomers. LCMS1 3.92 min. (M−H$_2$O)=427. LCMS1 4.08 min. (M−H$_2$O)=427. A DCM (2 mL) solution containing 4-{3-hydroxy-1-methyl-2-[4'-(trifluoromethoxy)biphenyl-3-yl]propyl}benzoate (50 mg, 0.1 µmol) was treated with [1,1,1-tris(acetyloxy)-1,1-dihydro-1,2-benziodoxol-3-(1H)-one] (64 mg, 0.15 mmol). After stirring for 1 hour the solution was concentrated and the residue purified by silica gel chromatography using a hexanes/ethyl acetate gradient to give the title compounds as a mixture of diastereomers. $^1$H NMR (400 MHz, CDCl$_3$): selected data δ 9.84 (d, J=2.3 Hz); 9.64 (d, J=2.3 Hz); 1.44 (d, J=6.7 Hz); 1.14 (d, J=7.0 Hz). LCMS1 4.11 min. (M+H)= 443. LCMS1 4.24 min. (M+H)=443.

Step F. Methyl 4-{2-(1H-indol-3-yl)-1-methyl-2-[4'-(trifluoromethoxy)biphenyl-3-yl]ethyl}benzoate LHMDS (1.0M THF, 3.0 mL) was added dropwise to a −10° C. THF (5 mL) solution containing (methoxymethyl) triphenylphosphonium chloride (1 g, 2.92 mmol). After stirring for 15 minutes a portion of the red ylide solution (ca. 0.365M, 11.0 ml, 0.365 mmol) was added dropwise to a 0° C. THF (1 mL) solution containing the intermediate from Step E (37 mg, 0.084 mmol). The solution was allowed to warm to room temperature and stirred for an additional 30 minutes. The solution was then partitioned between ethyl acetate and water. The organic phase was washed with brine and dried over magnesium sulfate. The solution was filtered, concentrated and the crude residue subjected to the Fisher indole reaction conditions described in EXAMPLES 3A/3B Step D. The crude material was purified by silica gel chromatography using a hexanes/ethyl acetate gradient to give the title compound as a mixture of diastereomers. $^1$H NMR (400 MHz, CDCl$_3$): selected data 54.53 (d, J=10.4 Hz); 4.45 (d, J=10.7 Hz); 1.41 (d, J=6.8 Hz); 1.22 (d, J=6.7 Hz). LCMS1 4.30 min. (M+H)=530. LCMS1 4.41 min. (M+H)=530.

Step G. N-(4-{2-(1H-indol-3-yl)-1-methyl-2-[4'-(trifluoromethoxy)biphenyl-3-yl]ethyl}benzoyl)-β-alanine The title compounds were prepared from the intermediate from Step F using the chemistry described in EXAMPLE 1. The diastereomeric products were separated by RP-HPLC. Diastereomer A: $^1$H NMR (400 MHz, CD$_3$OD): δ 7.69 (d, J=8.2 Hz, 1H); 7.59 (d, J=8.2 Hz, 2H); 7.39 (d, J=8.7 Hz, 2H); 7.33-7.29 (m, 5H); 7.22 (t, J=7.2 Hz, 3H); 7.11-7.03 (m, 3H); 6.97 (t, J=7.1 Hz, 1H); 4.49 (d, J=11.2 Hz, 1H); 3.84-3.76 (m, 1H); 3.54 (t, J=7.0 Hz, 2H); 2.56 (t, J=7.0 Hz, 2H); 1.35 (d, J=6.8 Hz, 3H). LCMS1 3.72 min. (M+H)=587. Diastereomer B (LCMS1 3.92 min. (M+H)=587) was resolved by chiral SFC—HPLC (21.2×250 mm ChiralPak AS-H, 50 ml/min of 30% MeOH/CO$_2$). Enantiomer 1: ChiralPak AS-H retention time 4.09 min, LCMS1 3.92 min. (M+H)=587. Enantiomer 2: ChiralPak AS-H retention time 4.80 min, LCMS1 3.92 min. (M+H)=587. Representative $^1$H NMR (400 MHz, CD$_3$OD): δ 7.67 (s, 1H); 7.64-7.60 (m, 2H); 7.55 (d, J=8.3 Hz, 2H); 7.46

(d, J=7.6 Hz, 2H); 7.38 (t, J=5.1 Hz, 3H); 7.34 (d, J=7.4 Hz, 1H); 7.30 (t, J=6.2 Hz, 2H); 7.13 (d, J=8.0 Hz, 1H); 7.08 (s, 1H); 6.94-6.90 (m, 1H); 6.86-6.82 (m, 1H); 4.56 (d, J=11.0 Hz, 1H); 3.80-3.72 (m, 1H); 3.52 (t, J=6.9 Hz, 2H); 2.55 (t, J=6.9 Hz, 2H); 1.17 (d, J=6.9 Hz, 3H).

Biological Assays

The ability of the compounds of the present invention to inhibit the binding of glucagon and their utility in treating or preventing type 2 diabetes mellitus and the related conditions can be demonstrated by the following in vitro assays. Glucagon Receptor Binding Assay A stable CHO (Chinese hamster ovary) cell line expressing cloned human glucagon receptor was maintained as described (Chicchi et al. *J Biol Chem* 272, 7765-9 (1997); Cascieri et al. *J Biol Chem* 274, 8694-7 (1999)). To determine antagonistic binding affinity of compounds 0.002 mg of cell membranes from these cells were incubated with $^{125}$I-Glucagon (New England Nuclear, Mass.) in a buffer containing 50 nM Tris-HCl (pH 7.5), 5 mM MgCl, 2 mM EDTA, 12% Glycerol, and 0.200 mg WGA coated PVT SPA beads (Amersham), +/−compounds or 0.001 MM unlabeled glucagon. After 4-12 hours incubation at room temperature, the radioactivity bound to the cell membranes was determined in a radioactive emission detection counter (Wallac-Microbeta). Data was analyzed using the software program Prism from GraphPad. The IC$_{50}$ values were calculated using non-linear regression analysis assuming single site competition. IC$_{50}$ values for the compounds of the invention are generally in the range of as low as about 1 nM to as high as about 500 nM, and thus have utility as glucagon antagonists.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (TopCount-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:
1. A compound represented by formula I:

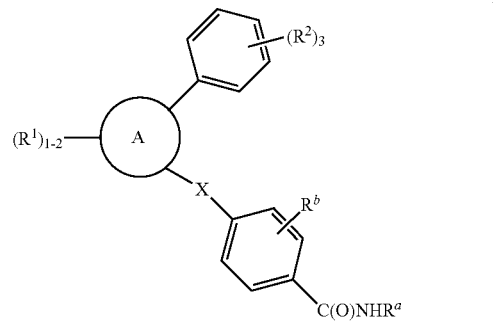

or a pharmaceutically acceptable salt thereof, wherein:
Ring A is selected from the group consisting of: phenyl, naphthyl, dihydroindenyl, tetrahydronaphthyl, indolyl, isoindolyl and pyridyl;
one to two $R^1$ groups are selected from:
a 6-10 membered aryl, aryloxy or arylthio group, or a 5-10 membered heteroaryl, heteroaryloxy or heteroarylthio group containing 1-2 nitrogen and 0-1 O or S atoms, said aryl and heteroaryl group, and the aryl and heteroaryl portions of aryloxy, arylthio, heteroaryloxy and heteroarylthio being optionally substituted with 1-3 groups selected from halo, OH, $CO_2R^4$, $SO_pR^5$, CN, $NO_2$, $C(O)NR^6R^7$, $NR^6R^7$, $C_{1-6}$alkyl, $C(O)C_{1-6}$alkyl or $OC_{1-6}$alkyl, the alkyl portions of $C_{1-6}$alkyl, $C(O)C_{1-6}$alkyl or $OC_{1-6}$alkyl being optionally substituted with: (1) 1-5 halo groups, up to perhalo, and (2) 1-2 groups selected from OH, $CO_2R^4$, $SO_pR^5$, CN, $NO_2$, $C(O)NR^6R^7$ and $NR^6R^7$,
said $R^1$ group being further optionally substituted with a member selected from the group consisting of pyrazole, imidazole, tetrazole, pyrrole, triazole, thiazole, furan, thiophene, thiadiazole and oxazole, optionally substituted with 1-2 groups selected from halo, OH, $CO_2R^4$, $SO_pR^5$, CN, $NO_2$, $C(O)NR^6R^7$, $NR^6R^7$, $C_{1-6}$alkyl, $C(O)C_{1-6}$alkyl or $OC_{1-6}$alkyl, the alkyl portions of $C_{1-6}$alkyl, $C(O)C_{1-6}$alkyl or $OC_{1-6}$alkyl being optionally substituted with: (1) 1-5 halo groups, up to perhalo, and (2) 1-2 groups selected from OH, $CO_2R^4$, $SO_pR^5$, CN, $NO_2$, $C(O)NR^6R^7$ and $NR^6R^7$;
each $R^2$ is H, halo, OH, $CO_2R^4$, $SO_pR^5$, CN, $NO_2$, $C(O)NR^6R^7$, $NR^6R^7$, $C_{1-6}$alkyl, $C(O)C_{1-6}$alkyl or $OC_{1-6}$alkyl, the alkyl portions of $C_{1-6}$alkyl, $C(O)C_{1-6}$alkyl or $OC_{1-6}$alkyl being optionally substituted with: (1) 1-5 halo groups, up to perhalo, and (2) 1-2 groups selected from OH, $CO_2R^4$, $SO_pR^5$, CN, $NO_2$, $C(O)NR^6R^7$ and $NR^6R^7$;
X is selected from the group consisting of: —O—, —S—, —(C($R^3$)$_2$)$_{1-2}$—, —OC($R^3$)$_2$—, —C($R^3$)$_2$O—;
$R^3$ is H, $C_{1-10}$alkyl, $C_{2-4}$alkenyl, Aryl or heteroaryl, said Aryl and heteroaryl being optionally substituted with 1-2 of halo, OH, $CO_2R^4$, $SO_pR^5$, CN, $NO_2$, $C(O)NR^6R^7$, $NR^6R^7$, $C_{1-6}$alkyl, $C(O)C_{1-6}$alkyl or $OC_{1-6}$alkyl, the alkyl portions of $C_{1-6}$alkyl, $C(O)C_{1-6}$alkyl or $OC_{1-6}$alkyl being optionally substituted with: (1) 1-5 halo groups, up to perhalo, and (2) 1-2 groups selected from OH, $CO_2R^4$, $SO_pR^5$, CN, $NO_2$, $C(O)NR^6R^7$ and $NR^6R^7$, with no more than one $R^3$ group being other than H and $C_{1-10}$alkyl, R⁴ is H or $C_{1-6}$alkyl, and R⁵ represents a member selected from the group consisting of: Aryl or Ar—$C_{1-10}$alkyl;

R⁶ and R⁷ each independently represent H or $C_{1-3}$alkyl;

p is 0, 1 or 2;

$R^a$ represents $CH_2CH_2CO_2R^4$, $CH_2CH(OH)CO_2R^4$ or 5-tetrazolyl; and $R^b$ is H, halo, OH, $CO_2R^4$, $SO_pR^5$, CN, $NO_2$, $C(O)NR^6R^7$, $NR^6R^7$, $C_{1-6}$alkyl, $C(O)C_{1-6}$alkyl or $OC_{1-6}$alkyl, the alkyl portions of $C_{1-6}$alkyl, $C(O)C_{1-6}$alkyl or $OC_{1-6}$alkyl being optionally substituted with: (1) 1-5 halo groups, up to perhalo, and (2) 1-2 groups selected from OH, $CO_2R^4$, $SO_pR^5$, CN, $NO_2$, $C(O)NR^6R^7$ and $NR^6R^7$.

2. A compound in accordance with claim 1 wherein ring A is selected from the group consisting of phenyl, naphthyl, pyridyl and tetrahydronaphthyl.

3. A compound in accordance with claim 2 wherein ring A is selected from the group consisting of phenyl, naphthyl and pyridyl.

4. A compound in accordance with claim 1 wherein 1-2 R¹ groups are selected from the group consisting of: phenyl, naphthyl, indolyl, imidazolyl, pyrazolyl, pyrimidinyl and O-phenyl, optionally substituted with 1-3 groups selected from: halo, CN, $OC_{1-6}$alkyl, $OhaloC_{1-6}$alkyl, $CO_2C_{1-6}$alkyl, $CO_2H$, $C(O)C_{1-6}$alkyl, $SO_2C_{1-6}$alkyl, $NO_2$, $C(O)NR^6R^7$ and pyrazolyl.

5. A compound in accordance with claim 1 wherein each R² is selected from the group consisting of: H, halo, $C_{1-6}$alkyl, $haloC_{1-6}$alkyl, $OC_{1-6}$alkyl and $OhaloC_{1-6}$alkyl.

6. A compound in accordance with claim 5 wherein each R² is selected from the group consisting of: H, Cl, F, OMe, OEt, O-n-propyl, O-i-propyl, O-n-butyl, O-t-butyl, $CF_3$ and $OCF_3$.

7. A compound in accordance with claim 1 wherein X represents —$(C(R^3)_2)_{1-2}$—, —$O(C(R^3)_2)_2$—, or —$C(R^3)_2O$—, wherein R³ is independently selected from H, $C_{1-10}$alkyl, Aryl and heteroaryl, said Aryl and heteroaryl being optionally substituted with 1-2 halo, CN, $C_{1-6}$alkyl, $OC_{1-6}$alkyl, $haloC_{1-6}$alkyl and $OhaloC_{1-6}$alkyl groups.

8. A compound in accordance with claim 1 wherein $R^a$ represents —$CH_2CH_2CO_2R^4$.

9. A compound in accordance with claim 8 wherein $R^a$ represents —$CH_2CH_2CO_2R^4$ and R⁴ represents H.

10. A compound in accordance with claim 1 wherein $R^b$ represents H.

11. A compound in accordance with claim 1 wherein:
ring A is selected from the group consisting of: phenyl, naphthyl, dihydroindenyl, tetrahydronaphthyl, indolyl, isoindolyl and pyridyl;

1-2 R¹ groups are selected from the group consisting of: phenyl, naphthyl, indolyl, imidazolyl, pyrazolyl, pyrimidinyl and O-phenyl, optionally substituted with 1-3 groups selected from: halo, CN, $OC_{1-6}$alkyl, $OhaloC_{1-6}$alkyl, $CO_2C_{1-6}$alkyl, $CO_2H$, $C(O)C_{1-6}$alkyl, $SO_2C_{1-6}$alkyl, $NO_2$, $C(O)NR^6R^7$ and pyrazolyl;

each R² is selected from the group consisting of: H, halo, $C_{1-6}$alkyl, $haloC_{1-6}$alkyl, $OC_{1-6}$alkyl and $OhaloC_{1-6}$alkyl;

X represents —$(C(R^3)_2)_{1-2}$—, —$O(C(R^3)_2)_2$—, or —$C(R^3)_2O$—, wherein R³ is independently selected from H, $C_{1-10}$alkyl, Aryl and heteroaryl, said Aryl and heteroaryl being optionally substituted with 1-2 halo, CN, $C_{1-6}$alkyl, $haloC_{1-6}$alkyl, $OC_{1-6}$alkyl and $OhaloC_{1-6}$alkyl groups;

$R^a$ represents —$CH_2CH_2CO_2R^4$ and R⁴ represents H, and $R^b$ represents H.

12. A compound in accordance with claim 1 selected from one of the following compounds:

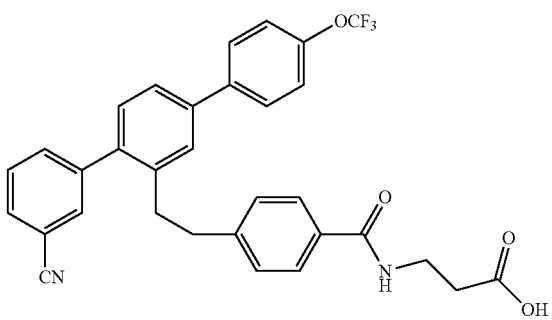

1

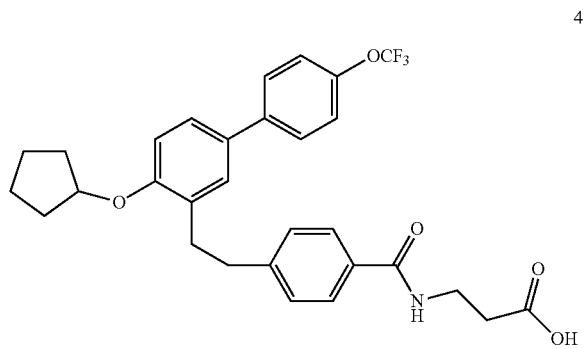

4

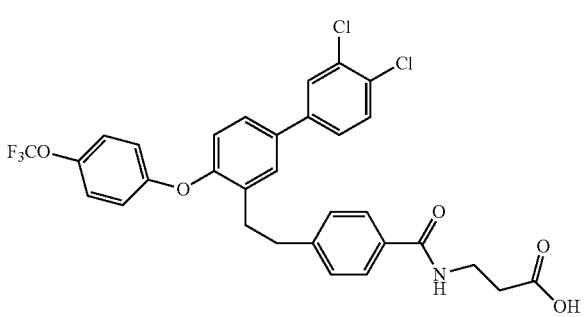

5

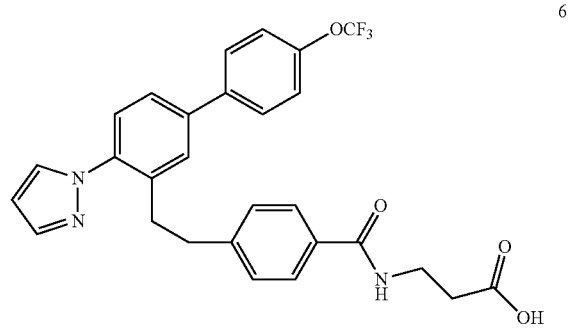

6

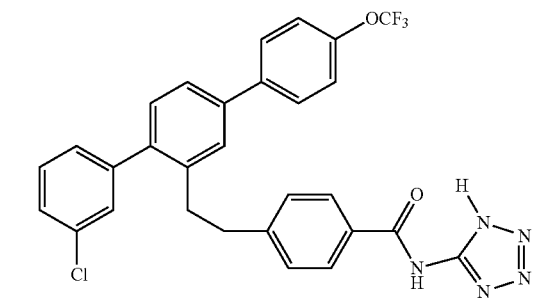
8
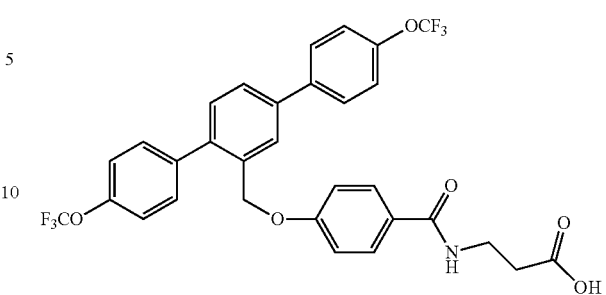
20
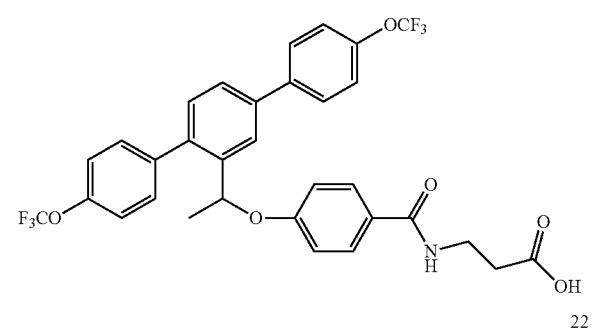
21
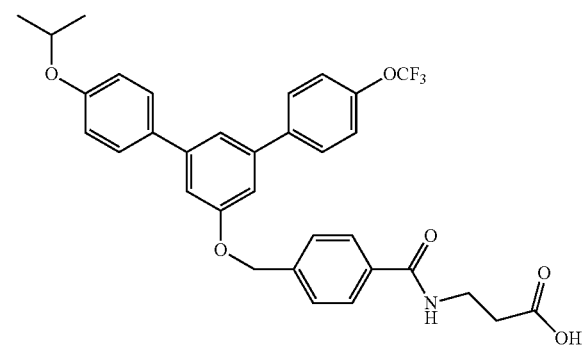
22
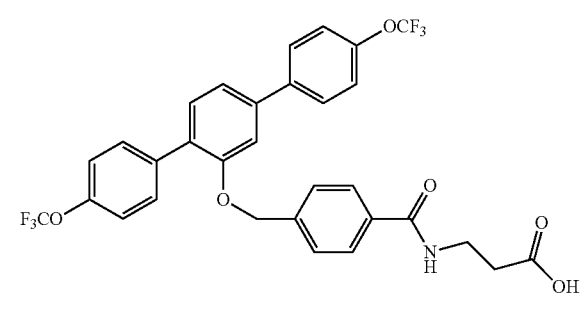
23
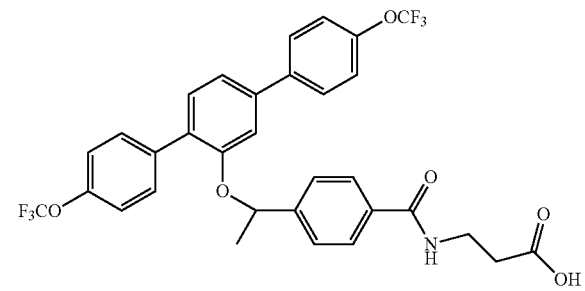
24

25
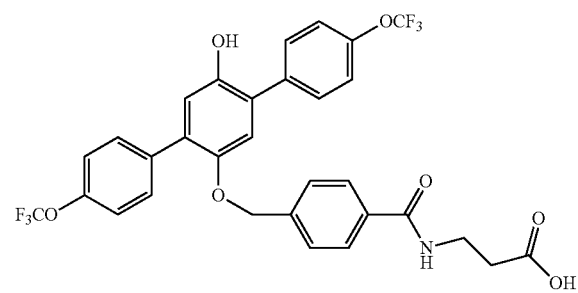
26
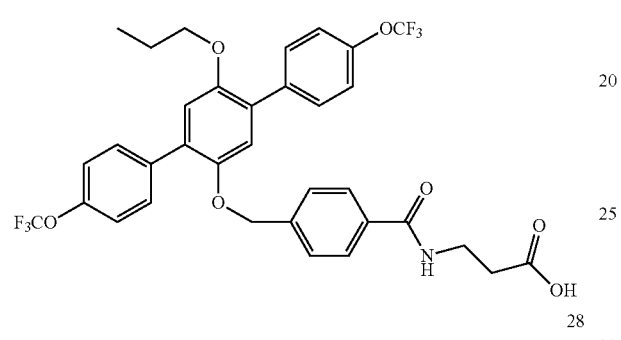
28
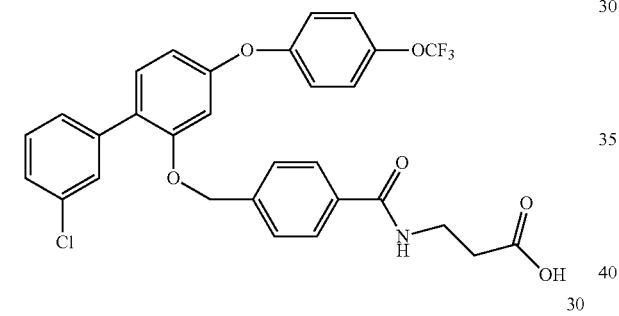
30
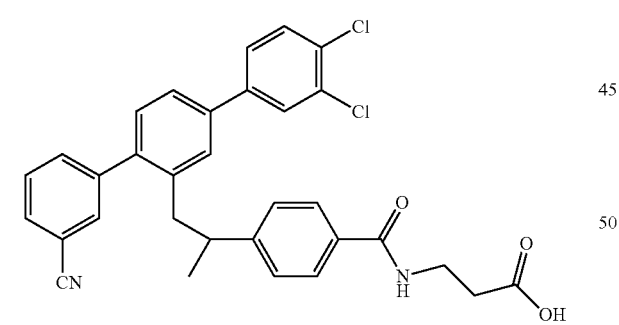
31
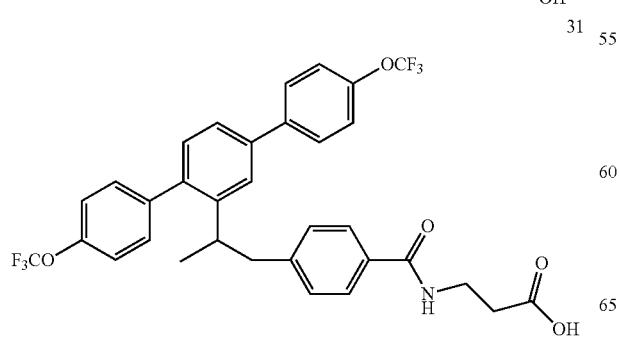
32
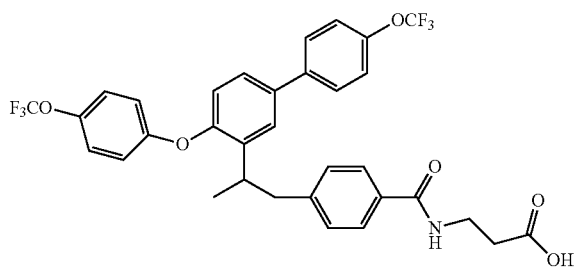
40
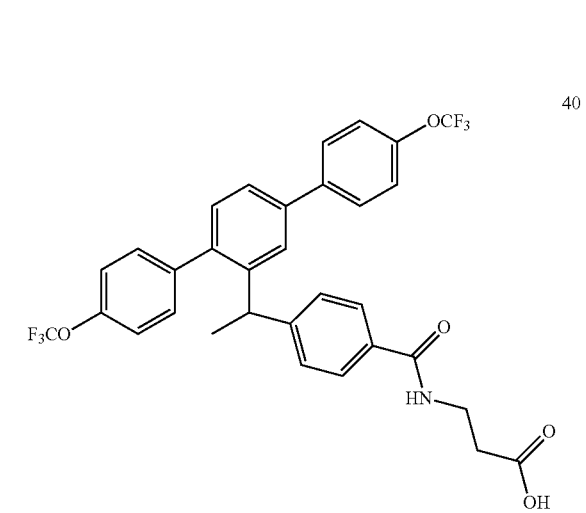
41
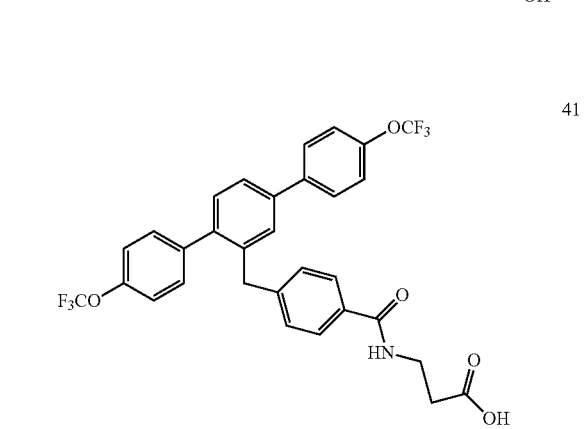
42
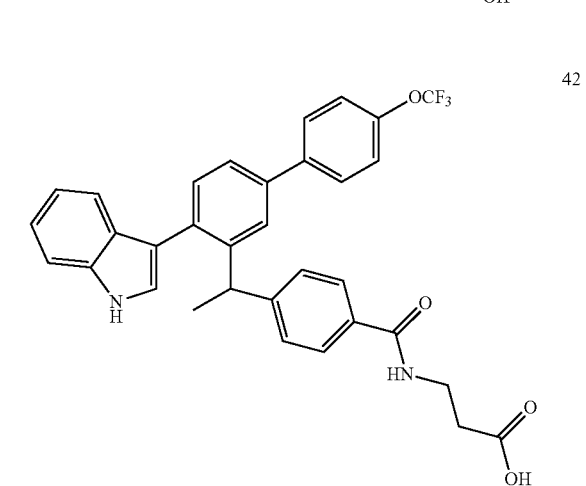

-continued

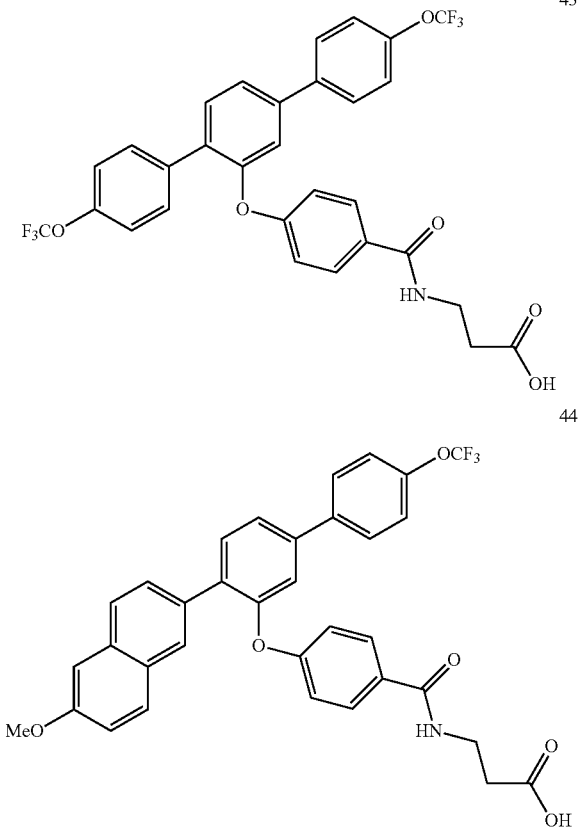

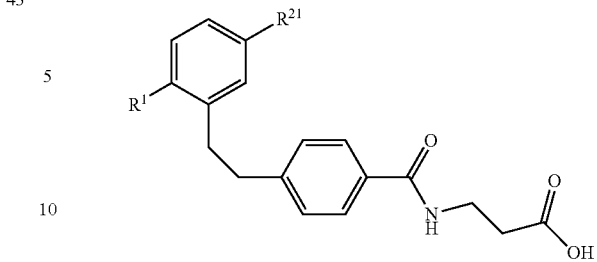

| COMPOUND | R¹ | R²¹ |
|---|---|---|
| 47 | 3,5-ClPh | 3,5-ClPh |
| 48 | 3-FPh | 3-FPh |
| 49 | 4-FPh | 4-FPh |
| 50 | 4-n-BuOPh | 4-n-BuOPh |
| 51 | Ph | 4-CF₃OPh |
| 52 | 4-tBuPh | 4-CF₃OPh |
| 53 | 4-iPrOPh | 4-CF₃OPh |
| 54 | 4-nBuOPh | 4-CF₃OPh |
| 55 | 2-EtOPh | 4-CF₃OPh |
| 56 | 2-iPrOPh | 4-CF₃OPh |
| 57 | 4-FPh | 4-CF₃OPh |
| 58 | 2-FPh | 4-CF₃OPh |
| 59 | 3-ClPh | 4-CF₃OPh |
| 60 | 2-ClPh | 4-CF₃OPh |
| 61 | 4-CNPh | 4-CF₃OPh |
| 62 | 2-CNPh | 4-CF₃OPh |
| 63 | 2-CF₃OPh | 4-CF₃OPh |
| 64 | 2-CF₃Ph | 4-CF₃OPh |
| 65 | 4-(C₂H₅O₂C)Ph | 4-CF₃OPh |
| 66 | 4-AcetylPh | 4-CF₃OPh |
| 67 | 4-MeSO₂Ph | 4-CF₃OPh |
| 68 | 2-MeOPh | 4-CF₃OPh |
| 69 | 4-MeOPh | 4-CF₃OPh |
| 70 | 4-HOPh | 4-CF₃OPh |
| 71 | 4-CF₃Ph | 4-CF₃OPh |
| 72 | 3-NO₂Ph | 4-CF₃OPh |
| 73 | 4-NO₂Ph | 4-CF₃OPh |
| 74 | 4-CO₂HPh | 4-CF₃OPh |
| 75 | 4-(N,N-dimethyl)Ph | 4-CF₃OPh |
| 76 | 4-(NMe₂CH₂)Ph | 4-CF₃OPh |
| 77 | 4-(NH₂CO)Ph | 4-CF₃OPh |
| 78 | 4-(NHMeCO)Ph | 4-CF₃OPh |
| 79 | 4-(NMe₂CO)Ph | 4-CF₃OPh |
| 80 | 2,4-ClPh | 4-CF₃OPh |
| 81 | 2-EtO, 4-ClPh | 4-CF₃OPh |
| 82 | 3-Cl, 4-nPrOPh | 4-CF₃OPh |
| 83 | 3-Cl, 4-EtOPh | 4-CF₃OPh |
| 84 | 3-F, 4-EtOPh | 4-CF₃OPh |
| 85 | 3-Cl, 4-MeOPh | 4-CF₃OPh |
| 86 | 3-F, 4-MeOPh | 4-CF₃OPh |
| 87 | 3,4-ClPh | 4-CF₃OPh |
| 88 | 3-Cl, 4-FPh | 4-CF₃OPh |
| 89 | 3,5-ClPh | 4-CF₃OPh |
| 90 | 2,3,5-FPh | 4-CF₃OPh |
| 91 | 3-CN, 4-F Ph | 4-CF₃OPh |
| 92 | 3-F, 4-CN Ph | 4-CF₃OPh |
| 93 | 2-F, 5-CF₃ Ph | 4-CF₃OPh |
| 94 | 2-F, 5-CN Ph | 4-CF₃OPh |
| 95 | 2-MeO, 5-NO₂ Ph | 4-CF₃OPh |
| 96 | 2-MeO, 5-CN Ph | 4-CF₃OPh |
| 97 | 4-Pyridyl | 4-CF₃OPh |
| 98 | 3-Pyridyl | 4-CF₃OPh |
| 99 | 6-EtO, 2-Naphthyl | 4-CF₃OPh |
| 100 | 5-CN, 2-Indole | 4-CF₃OPh |
| 101 | 4-(1-pyrazole)phenyl | 4-CF₃OPh |
| 102 | 2-F, 4-pyridyl | 4-CF₃OPh |
| 103 | 2-Cl, 4-pyridyl | 4-CF₃OPh |
| 104 | 1-imidazole | 4-CF₃OPh |
| 105 | 5-pyrazole | 4-CF₃OPh |
| 106 | 3-(1-pyrazole) Ph | 4-CF₃OPh |
| 107 | 2,6-Pyrimidine | 4-CF₃OPh |
| 108 | 3,5-Pyrimidine | 4-CF₃OPh |
| 109 | 2-MeO, 5-Pyridyl | 4-CF₃OPh |
| 110 | 3-Indole | 4-CF₃OPh |
| 111 | 5-CF₃O, 3-Indole | 4-CF₃OPh |
| 112 | 5-CF₃, 3-Indole | 4-CF₃OPh |
| 113 | 4,6-Cl, 3-Indole | 4-CF₃OPh |
| 116 | cyclopropyl | 4-CF₃OPh |
| 118 | 4-CF₃OPh | 4-F Ph |
| 119 | 4-CF₃OPh | 4-tBu Ph |
| 119 | 4-CF₃OPh | 3-Cl, 4-F Ph |
| 120 | 4-CF₃OPh | 3-Cl, 4-nPrO Ph |
| 121 | 4-CF₃OPh | 3-Cl, 4-EtO Ph |
| 122 | 4-CF₃OPh | 3-Cl, 4-MeO Ph |
| 123 | 4-CF₃OPh | 3,5-Cl Ph |
| 124 | 4-CF₃OPh | 2,4-Cl Ph |
| 125 | 4-CF₃OPh | 2-EtO, 4-Cl Ph |
| 126 | 4-CF₃OPh | 3-F, 4-EtO Ph |
| 127 | 4-CF₃OPh | 2-CF₃ Ph |
| 128 | 4-CF₃OPh | 2,3,5-F Ph |
| 129 | 4-CF₃OPh | 2-EtO Ph |
| 130 | 4-CF₃OPh | 2-Cl Ph |
| 131 | 4-CF₃OPh | 3-Cl Ph |
| 132 | 4-CF₃OPh | 3-F, 4-MeO Ph |
| 133 | 4-CF₃OPh | 3,4-Cl Ph |
| 136 | OPh | 4-CF₃OPh |

-continued

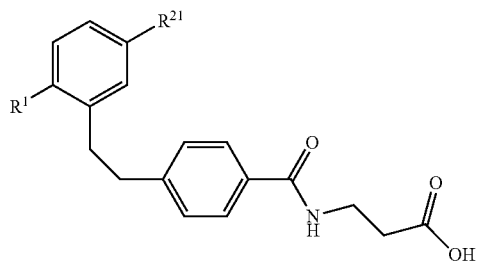

| COMPOUND | R¹ | R²¹ |
|---|---|---|
| 137 | OPh | 3,4-Cl Ph |
| 138 | O-(4-MeO Ph) | 3,4-Cl Ph |
| 139 | O-(3-CN Ph) | 3,4-Cl Ph |
| 140 | O-(3-F, 4-MeO Ph) | 3,4-Cl Ph |
| 141 | O-(3-MeO Ph) | 3,4-Cl Ph |
| 142 | O-(4 CF₃O Ph) | 3,4-Cl Ph |
| 143 | O-(4-F Ph) | 3,4-Cl Ph |
| 144 | O-(4-CN Ph) | 3,4-Cl Ph |
| 145 | O-(4-F Ph) | 4-CF₃OPh |

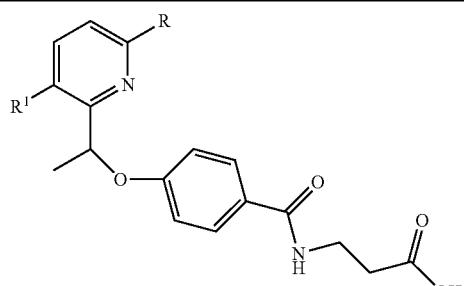

| COMPOUND | R | Isomer |
|---|---|---|
| 148 | 4-CF₃OPh | Enantiomer A (Faster Eluting) |
| 149 | 4-CF₃OPh | Enantiomer B (Slower Eluting) |
| 150 | 4-F Ph | Racemic |
| 152 | 4-CF₃OPh | 4-CF₃OPh |
| 153 | 4-nBuO Ph | 4-CF₃OPh |

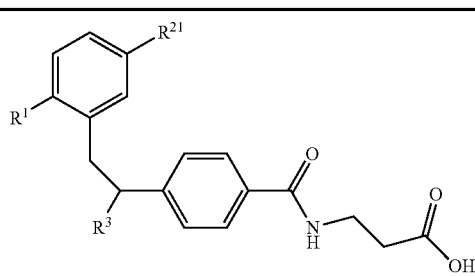

| COMPOUND | R¹ | R²¹ | R³ |
|---|---|---|---|
| 161 | 3-CN Ph | 4-CF₃OPh | Me Enantiomer A |
| 162 | 3-CN Ph | 4-CF₃OPh | Me Enantiomer B |
| 163 | 2-CF₃ Ph | 4-CF₃OPh | Me Racemic |

-continued

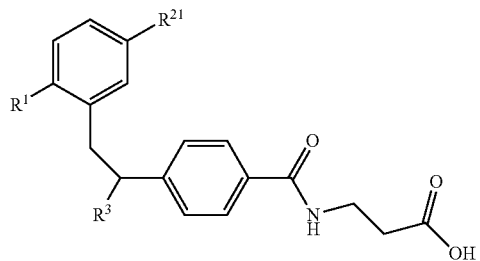

| COMPOUND | R¹ | R²¹ | R³ |
|---|---|---|---|
| 164 | 2-CF₃ Ph | 4-CF₃ Ph | Me Racemic |
| 165 | 2-CF₃ Ph | 3,4-Cl Ph | Me Racemic |
| 166 | 2-CF₃ Ph | 2-Naphthyl | Me Racemic |
| 167 | 2-CF₃ Ph | 6 MeO, 2-Naphthyl | Me Racemic |
| 168 | 2-CF₃ Ph | 3-Quinoline | Me Racemic |
| 169 | 3-Cl Ph | 3,4-Cl Ph | Me Racemic |

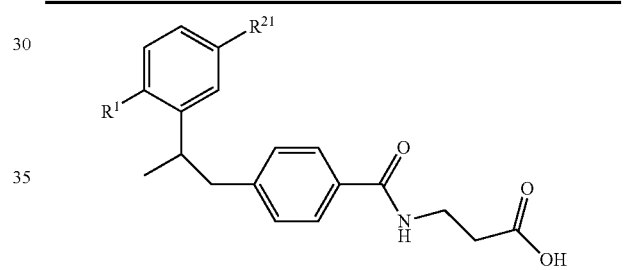

| COMPOUND | R¹ | R²¹ | Isomer |
|---|---|---|---|
| 178 | 4-CN Ph | 4-CN Ph | Racemic |
| 179 | O-(4-F Ph) | 4-CF₃OPh | Racemic |

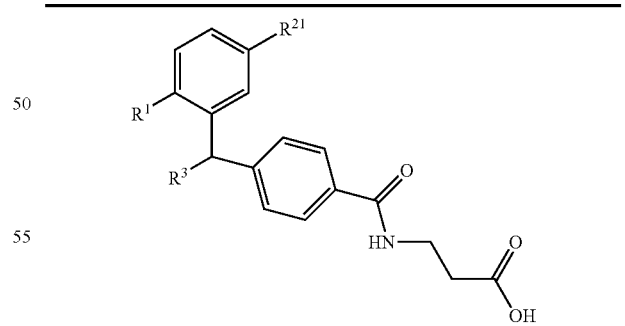

| COMPOUND | R¹ | R²¹ | R³ |
|---|---|---|---|
| 184 | 4-nBuO Ph | 4-nBuO Ph | H |
| 185 | 4-CF₃OPh | 4-CF₃O Ph | Et Enantiomer A |
| 186 | 4-CF₃OPh | 4-CF₃OPh | Et Enantiomer B |
| 187 | 3-CNPh | 4-CF₃OPh | Me Enantiomer A |

-continued

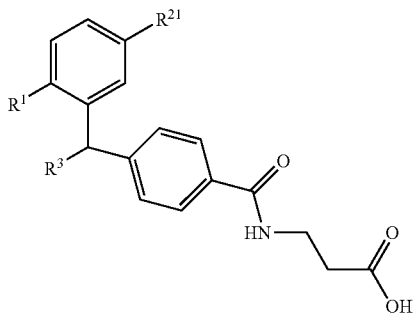

| COMPOUND | R$^1$ | R$^{21}$ | R$^3$ |
|---|---|---|---|
| 188 | 3-CNPh | 4-CF$_3$OPh | Me Enantiomer B |
| 189 | 3-CNPh | 4-CF$_3$OPh | H |
| 190 | Ph | 4-CF$_3$OPh | H |
| 191 | 6-MeO, 2-Naphthyl | 4-CF$_3$OPh | H |
| 192 | O(4-F Ph) | 4-CF$_3$OPh | Me Racemic |

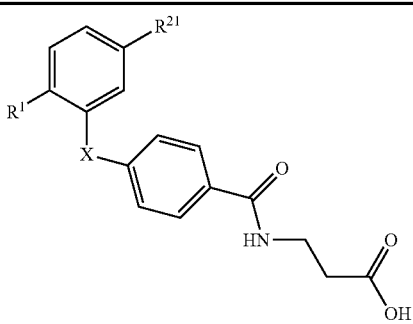

| COMPOUND | R$^1$ | R$^{21}$ | X |
|---|---|---|---|
| 199 | 4-Cl Ph | 4-CF$_3$OPh | O |
| 200 | 3,4-F Ph | 4-CF$_3$OPh | O |
| 201 | 3-CN Ph | 4-CF$_3$OPh | O |

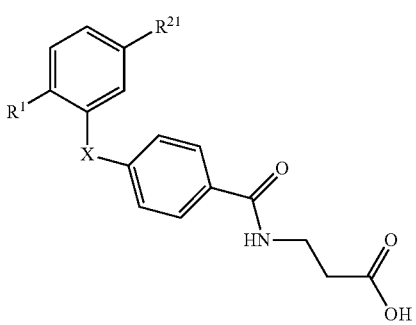

| COMPOUND | R$^1$ | R$^{21}$ | X |
|---|---|---|---|
| 202 | 2-CF$_3$ Ph | 4-CF$_3$OPh | O |
| 203 | 3,5-Cl Ph | 4-CF$_3$OPh | O |
| 204 | 6-MeO, 2-Naphthyl | 3,5-Cl Ph | O |
| 205 | 4-CF$_3$OPh | 4-CF$_3$OPh | S | or a pharmaceutically acceptable salt thereof.

13. A pharmaceutical composition comprising a compound in accordance with claim 1 in combination with a pharmaceutically acceptable carrier.

14. A method of treating type 2 diabetes mellitus in a mammalian patient in need of such treatment comprising administering to said patient a compound in accordance with claim 1 in an amount that is effective to treat said type 2 diabetes mellitus.

15. A method of treating atherosclerosis in a mammalian patient in need of such treatment, comprising administering to said patient a compound in accordance with claim 1 in an amount effective to treat atherosclerosis.

* * * * *